(12) United States Patent
Sonoki et al.

(10) Patent No.: US 11,845,972 B2
(45) Date of Patent: Dec. 19, 2023

(54) MUCONIC ACID-PRODUCING TRANSFORMED MICROORGANISM AND USE THEREOF

(71) Applicant: HIROSAKI UNIVERSITY, Hirosaki (JP)

(72) Inventors: Tomonori Sonoki, Hirosaki (JP); Eiji Masai, Nagaoka (JP); Naofumi Kamimura, Nagaoka (JP)

(73) Assignee: HIROSAKI UNIVERSITY, Hirosaki (JP)

( * ) Notice: Subject to any disclaimer, the term of this patent is extended or adjusted under 35 U.S.C. 154(b) by 241 days.

(21) Appl. No.: 17/285,911

(22) PCT Filed: Oct. 17, 2019

(86) PCT No.: PCT/JP2019/040908
§ 371 (c)(1),
(2) Date: Apr. 16, 2021

(87) PCT Pub. No.: WO2020/080467
PCT Pub. Date: Apr. 23, 2020

(65) Prior Publication Data
US 2021/0371885 A1 Dec. 2, 2021

(30) Foreign Application Priority Data

Oct. 17, 2018 (JP) .................................. 2018-196001

(51) Int. Cl.
*C12N 9/88* (2006.01)
*C12P 7/44* (2006.01)
*C12N 1/16* (2006.01)
*C12P 7/42* (2006.01)

(52) U.S. Cl.
CPC .................. *C12P 7/44* (2013.01); *C12N 1/16* (2013.01); *C12P 7/42* (2013.01)

(58) Field of Classification Search
CPC .................. C12N 9/88; C12P 7/42; C12P 1/20
See application file for complete search history.

(56) References Cited

U.S. PATENT DOCUMENTS

| 2016/0017381 A1 | 1/2016 | Beckham et al. | |
| 2021/0277429 A1* | 9/2021 | Sillers | ............ C12Y 401/01063 |

OTHER PUBLICATIONS

Shinoda et al "Isolation of a novel platform bacterium for lignin valorization and its application in glucose-free cis, cis-muconate production", J Ind Microbiol Biotechnol 46, 1071-1080 (2019). https://doi.org/10.1007/s10295-019-02190-6.
Mar. 2019, lecture No. 3D7a11, entire text, non-official translation (Abe, Nanase et al., "Muconic acid prdocution (I) using *Pseudomonas* sp.NGC7 strain which can cope with a variety of lignin composition: Production of muconic acid-producing strain using newly isolation microbe", lecture abstracts of conference of japan society of bioscience, biotechnology,and agrochemistry).
Mar. 2019, lecture No. 3D7a12, entire text, non-official translation (akitsu,miho et al.,"Muconic acid prdocution (II) using *Pseudomonas* sp.NGC7 strain which can cope with a variety of lignin composition: Production from conifer lignin",strain using newly isolation microbe, lecture abstracts of conference of japan society of bioscience, biotechnology,and agrochemistry).
Sonoki et al"glucose free cis, cis-muconic acid production via new metabolic designs corresponding to the heteogeneity of lignin",ACS Sustainable Chem. Eng. 2018, 6, 1, 1256-1264 Publication Date:Dec. 4, 2017 https://doi.org/10.1021/acssuschemeng.7b03597.
Zouari et al."cloning and sequencing of a phenol hydroxylase gene of pseudomonas pseudoalcligenes strain MH1", Appl Biochem Biotechnol. Jul.-Dec. 2002;102-103(1-6):261-76. doi: 10.1385/abab:102-103:1-6:261.
Bandounas et al "isolation and characterizion of novel bacterial strains exhibiting ligninolytic potential", BMC Biotechnol 11, 94 (2011). https://doi.org/10.1186/1472-6750-11-94.
Arunakumari et al "utilization of aromaticsubstances by pseudomonas solanacearum", indian journal of experimental biology, vvol 22, Jan. 1984, pp. 32-36, received Dec. 7, 1982.
Omori et al"protocatechuic acid production from trans-ferulic acid by *Pseudomonas* sp. HF-1 mutants defective in protocatechuic acid catabolism", Appl Microbiol Biotechnol 29, 497-500 (1988). https://doi.org/10.1007/BF00269075.
Johnson et al., "Enhancing muconic acid production from glucose and lignin-derived aromatic compounds via increased protocatechuate decarboxylase activity," Metabol. Eng. Comm. 3: 111-119, 2016.
International Search Report of International Patent Application No. PCT/JP2019/040908.
Notification of transmittal of translation of the International Preliminary Report on Patentability (Form PCT/IB/338) of International Patent Application No. PCT/JP2019/040908.
Translation of International Preliminary Report on Patentability of International Patent Application No. PCT/JP2019/040908.

(Continued)

*Primary Examiner* — Tekchand Saidha
(74) *Attorney, Agent, or Firm* — JMB Davis Ben-David

(57) ABSTRACT

The objective of the present invention is to provide a microorganism that makes it possible to produce muconic acid from a lignin-derived aromatic compound with sufficient economic efficiency and without depending on the type of lignin, and a method of producing muconic acid using the microorganism. The objective can be achieved by a transformed microorganism wherein the host microorganism is a microorganism of the genus *Pseudomonas* that has pcaH gene, pcaG gene, catA gene, and catB gene on its chromosome, and that can assimilate an aromatic compound derived from syringyl lignin; and wherein the transformed microorganism lacks at least one gene selected from the group consisting of pcaH gene and pcaG gene on its chromosome, lacks catB gene on its chromosome, and expresses aroY gene inserted; and a method of producing muconic acid using the transformed microorganism and the like.

5 Claims, No Drawings
Specification includes a Sequence Listing.

(56) References Cited

OTHER PUBLICATIONS

Extended European Search Report of corresponding EP patent application Patent Application No. 19874401.3, dated Nov. 4, 2022.
Christopher W. Johnson et al "enhancing muconic acid production from glucose and lignin-derived aromatic compounds via increased protocatechuate decarboxylase activity" Metabolic Engineering Communications, vol. 3, Dec. 2016, pp. 111-119.
Wang Songwei et al "development of a plasmid-free biosynthetic pathway for enhanced muconic acid production in pseudomonas clororaphis ht66" ACS Synth. Biol. 2018, 7, 4, 1131-1142 Publication Date:Apr. 2, 2018 https://doi.org/10.1021/acssynbio.8b00047.
Sonoki Tomonori et al "Enhancement of protocatechuate decarboxylase activity for the effective production of muconate from lignin-related aromatic compounds", J Biotechnol. Dec. 20, 2014; 192 Pt A:71-7. doi: 10.1016/j.biotec.2014.10.027, DOI: 10.1016/j.jbiotec.2014.10.027.
Office Action from JPO for JP Patent Application No. JP2020-553289, dated Jul. 4, 2023.

\* cited by examiner

MUCONIC ACID-PRODUCING TRANSFORMED MICROORGANISM AND USE THEREOF

This is the U.S. National Stage of International Patent Application No. PCT/JP2019/040908, filed on Oct. 17, 2019, which claims the benefit of priority to Japanese Patent Application No. 2018-196001, filed on Oct. 17, 2018, the disclosure of which is incorporated herein by reference in its entirety.

TECHNICAL FIELD

This invention relates to a transformed microorganism capable of producing muconic acid, and a method of producing muconic acid using the transformed microorganism. In particular, the present invention relates to a transformed microorganism capable of having growth and producing muconic acid using a lignin-derived aromatic compound as a carbon source.

BACKGROUND ART

Lignin is an amorphous polymeric substance existing in plants as a component of vascular bundle cell wall. Lignin is formed as a result of complex condensation reactions of phenyl propane-based constituent units, and show a remarkable chemical structural characteristic of containing methoxy groups. Lignin takes a role of causing lignified plant cells to mutually agglutinate, thereby strengthening plant tissues. Lignin is contained by about 18% to 36% in woods and by about 15% to 25% in herbaceous plants. Thus, various attempts to degrade lignin and obtain useful compounds from that for the purpose of effectively exploiting wood resources have been and being made. It has been known that there are three types of lignin derived from biomass such as woods: p-hydroxyphenyl lignin, guaiacyl lignin and syringyl lignin.

On the other hand, cis,cis-muconic acid (hereinafter referred to simply as muconic acid) is a highly reactive compound due to the presence of two double bonds and two carboxy groups in its molecule. Various muconic acid derivatives starting from muconic acid are known, including lactones, sulfones, polyamides, polyesters, thioesters, and addition polymers. Such muconic acid derivatives are known to have a variety of applications, and can be used, for example, as surfactants, flame retardants, UV light stabilizers, thermosetting plastics, and coating agents.

Thus, muconic acid can be used for various applications in the form of muconic acid derivatives. If muconic acid can be produced from lignin, it would be very useful in achieving resource recycling. Some methods of producing muconic acid from lignin or lignin-derived substances have been attempted so far, and in particular, bioconversions using certain types of microorganisms have been studied.

For example, the following Non-Patent Document 1 (which is incorporated by reference herein in its entirety) discloses the production of the transformed microorganism wherein the host microorganism is *Pseudomonas putida*, and the transformed microorganism lacks pcaH and pcaG genes on its chromosome (hereinafter, in combination, referred to as pcaHG gene) as well as catR gene, catB gene, catC gene, and catA gene on its chromosome, and expresses catA and aroY genes inserted or catA, aroY, and ecdB genes inserted. Non-Patent Document 1 also discloses producing muconic acid from p-coumaric acid by the transformed microorganism grown on glucose.

CITATION LIST

Non-Patent Literature

Non-Patent Document 1: C. W. Johnson et al, Metabolic Engineering Communications, 3, 111-119, 2016.

SUMMARY OF THE INVENTION

Problems to be Solved by the Invention

Indeed, muconic acid can be produced from p-coumaric acid by using the transformed microorganism disclosed in Non-Patent Document 1. However, the transformed microorganism disclosed in Non-Patent Document 1 requires glucose which is an expensive carbon source for growth, and thus there is a problem that the method of producing muconic acid using the transformed microorganism disclosed in Non-Patent Document 1 is not economical.

On the other hand, the present inventors have prepared a transformed microorganism wherein the host organism was *Pseudomonas putida*, and the transformed microorganism lacked pcaHG and catB genes on its chromosome, and expressed pcaHG and aroY genes inserted, and have invented a method of producing muconic acid using the transformed microorganism without consuming glucose, while proliferating using aromatic compounds derived from lignin. The international application claiming the transformed microorganism and method was filed on Apr. 24, 2018 (PCT/JP2018/16674).

However, the host microorganism disclosed in the description of the International Application PCT/JP2018/16674 cannot assimilate aromatic compounds derived from syringyl lignin. As such, there is a problem that the method using the transformed microorganism disclosed in the description of the International Application PCT/JP2018/16674 cannot utilize as biomass broad leaf trees containing syringyl lignin in large amount.

In view of the above circumstances, it is an objective of the present invention to provide a microorganism that makes it possible to produce muconic acid from a lignin-derived aromatic compound with sufficient economic efficiency and without depending on the type of lignin, and a method of producing muconic acid using the microorganism.

Means for Solving the Problems

In order to find a way to solve the aforementioned problems, the present inventors made extensive efforts to isolate a microorganism of the genus *Pseudomonas* that can be assimilate an aromatic compound derived from syringyl lignin.

As a result, the present inventors succeeded in obtaining several *Pseudomonas* microorganism strains that can grow using a lignin-derived compound contained in nitrobenzene degradation products of birch that is one of broad leaf trees as a sole source of carbon. The present inventors selected a strain with a high proliferative ability among them, and succeeded in constructing a transformed microorganism wherein pcaHG and catB genes on its chromosome are disrupted according to the method described in the International Application PCT/JP2018/16674, and then aroY gene is inserted as a foreign gene and overexpressed.

Surprisingly, the present inventors found that the resulting transformed microorganism could produce muconic acid from aromatic compounds derived from p-hydroxyphenyl lignin and/or guaiacyl lignin, while growing using an aromatic compound derived from syringyl lignin but not glucose.

More surprisingly, when the present inventors created a transformed microorganism that overexpressed pcaHG gene in addition to aroY gene as foreign genes, they found that aromatic compounds derived from p-hydroxyphenyl lignin and/or guaiacyl lignin enabled the transformed microorganism to grow and produce muconic acid.

In addition, the present inventors had prepared a transformed microorganism wherein the host organism was *Sphingobium* species, and the transformed microorganism lacked a protocatechuic acid-degrading enzyme gene, ligAB gene on its chromosome, and expressed catA gene and aroY gene inserted, and had invented a method of producing muconic acid using the transformed microorganism in which the transformed microorganism can grow and producing muconic acid with the use of aromatic compounds derived from syringyl lignin. The international application claiming the transformed microorganism and method was filed on Apr. 24, 2018 (PCT/JP2018/16675).

The transformed microorganism disclosed in the International Application PCT/JP2018/16675 shows a nutrient requirement. Specifically, when using the transformed microorganism in the absence of tryptone, the proliferation rate and the rate of producing muconic acid decreased.

In contrast, when using the above transformed microorganism prepared by the present inventors, it does not require tryptone and the proliferation rate is unchanged, and then muconic acid can be efficiently.

On the basis of the above facts and findings, the present inventors have successfully invented a transformed microorganism that makes it possible to produce muconic acid from a lignin-derived aromatic compound without depending on the type of lignin, and a method of producing muconic acid using the transformed microorganism.

Needless to mention, lignin-derived aromatic compounds can be obtained from biomass, such as waste materials, and thus are very inexpensive when compared to glucose. Therefore, the method of producing muconic acid using the transformed microorganism provided by the present inventors is more economically advantageous than the method using the transformed microorganism disclosed in Non-Patent Document 1. The present invention has been completed based on these findings and successful examples.

According to one embodiment of the present invention, the transformed microorganisms of [1] to [5] below are provided.

(1) A transformed microorganism wherein the host microorganism is a microorganism of the genus *Pseudomonas* that has pcaH gene, pcaG gene, catA gene, and catB gene on its chromosome, and that can assimilate an aromatic compound derived from syringyl lignin; and wherein the transformed microorganism lacks at least one gene selected from the group consisting of pcaH gene and pcaG gene on its chromosome, and lacks catB gene on its chromosome, and expresses aroY gene inserted.

(2) A transformed microorganism wherein the host microorganism is a microorganism of the genus *Pseudomonas* that has pcaH gene, pcaG gene, catA gene, and catB gene on its chromosome, and that can assimilate an aromatic compound derived from syringyl lignin; and wherein the transformed microorganism lacks at least one gene selected from the group consisting of pcaH gene and pcaG gene on its chromosome, and lacks catB gene on its chromosome, expresses pcaH gene inserted and pcaG gene inserted, and expresses aroY gene inserted.

(3) The transformed microorganism according to (2) above, wherein the aroY gene inserted, the pcaH gene inserted and the pcaG gene inserted are under the control of the identical promoter.

(4) The transformed microorganism according to any one of (1) to (3) above, wherein further expresses at least one gene selected from the group consisting of catA gene inserted, vanA gene inserted, vanB gene inserted, and kpdB gene inserted.

(5) The transformed microorganism according to any one of (1) to (4) above, wherein the microorganism of the genus *Pseudomonas* is selected from the group consisting of *P. putida*, *P. plecoglossicida*, *P. taiwanensis*, *P. monteilii*, *P. fulva*, and *Pseudomonas* species which is a related species to them.

According to one embodiment of the present invention, the production method of (6) to (8) below are provided.

(6) A method of producing muconic acid, including a step of applying an aromatic compound derived from p-hydroxyphenyl lignin and/or an aromatic compound derived from guaiacyl lignin, and an aromatic compound derived from syringyl lignin to the transformed microorganism according to any one of (1) to (5) above to obtain muconic acid.

(7) A method of producing muconic acid, including a step of applying an aromatic compound derived from p-hydroxyphenyl lignin and/or an aromatic compound derived from guaiacyl lignin to the transformed microorganism according to any one of (2) to (5) above to obtain muconic acid.

(8) The method according to (7) above, wherein the step is conducted under a condition in which the dissolved oxygen concentration is in the range between 1% and 13%.

According to one embodiment of the present invention, the transformed microorganism of (9) below is provided.

(9) A transformed microorganism wherein the host microorganism is a microorganism of the genus *Pseudomonas* that has pcaH gene, pcaG gene, catA gene, and catB gene on its chromosome, and that can assimilate an aromatic compound derived from syringyl lignin; and wherein the transformed microorganism lacks at least one gene selected from the group consisting of pcaH gene and pcaG gene on its chromosome.

According to one embodiment of the present invention, the production method of (10) below is provided.

(10) A method of producing protocatechuic acid, including a step of applying an aromatic compound derived from p-hydroxyphenyl lignin and/or an aromatic compound derived from guaiacyl lignin, and an aromatic compound derived from syringyl lignin to the transformed microorganism according to (9) above to obtain protocatechuic acid.

Effect of the Invention

According to the transformed microorganism and the production method of one embodiment of the present invention, muconic acid and protocatechuic acid can be produced from a lignin-derived aromatic compound at a lower cost and without depending on the type of lignin, as compared to the methods using known microorganisms. Therefore, according to the transformed microorganism and the production method of one embodiment of the present invention, it is expected to produce muconic acid and protocatechuic acid on an industrial scale as part of the effective utilization of biomass containing lignin.

DESCRIPTION OF EMBODIMENTS

While the transformed microorganism and production method of an aspect of the present invention will be now described in detail, the technical scope of the present invention is not limited only by the description in this section, and the present invention may be modified insofar as it can achieve its purpose.

Unless otherwise specified, each term used herein is used in the meaning commonly used by those skilled in the art and should not be construed to have any meaning that is unduly limiting.

For example, the term "and/or" means any one, or an arbitrary combination of two or more, or a combination of all of a plurality of related items listed.

(Outline of Transformed Microorganism)

The transformed microorganism according to one embodiment of the present invention relates to a microorganism obtained by transforming a host organism in a way to disrupt specific genes on the chromosome of the host organism. The transformed microorganism according to one embodiment of the present invention can be broadly classified into three types depending on whether or not the host microorganism has been transformed to express specific genes which are involved in the pathway for muconic acid synthesis from protocatechuic acid and, are inserted as foreign genes.

The term "lack of gene" means that a gene does not function properly and the expression of the gene is hindered so that the gene cannot be transcribed properly or a protein to be produced by the expression of the gene cannot be translated properly. The lack of gene can occur, for example, when all or part of a gene is disrupted, deleted, replaced, or inserted, resulting in a change in the structure of the gene. However, the lack of gene can also occur, for example, when the expression of a gene is suppressed by blocking the regulatory region of the gene, without causing any change in the structure of the gene.

The term "expression of gene" means production of a protein encoded by a gene via transcription, translation, and the like, in a form having an original conformation or activity. The term "overexpression of gene" means that a gene is inserted in a host organism, and a protein encoded by the inserted gene is produced at a level exceeding the normal expression level of the protein in the host organism.

(Genes to be Deleted or Inserted)

For the transformed microorganism, the host microorganism has pcaH gene, pcaG gene, catA gene, and catB gene on its chromosome. Among the genes, the transformed microorganism lacks pcaH gene, pcaG gene, and catB gene on the chromosome of the host organism. The transformed microorganism preferably lacks both pcaH gene and pcaG gene the host microorganism originally has on its chromosome, but any one of pcaH gene and pcaG gene may be lacked in the transformed microorganism.

pcaH and pcaG genes are not particularly limited so long as the genes are those expressing beta and alpha subunits of protocatechuate 3,4-dioxygenase, respectively. Specific examples of pcaH and pcaG genes include genes having the nucleotide sequences of SEQ ID NOs: 37 and 38, respectively.

Protocatechuate 3,4-dioxygenase is possessed, for example, by *Pseudomonas putida* KT2440 strain. Protocatechuate 3,4-dioxygenase is generally known to have the activity in catalyzing the reaction to synthesize 3-carboxymuconic acid from protocatechuic acid and to require $Fe^{3+}$ as a cofactor. As used herein, any one or both of pcaH gene and pcaG gene may be collectively referred to as pcaHG gene.

catB gene is not particularly limited so long as the gene is a gene expressing cis, cis-muconic acid cycloisomerase. Specific examples of catB gene include a gene having the nucleotide sequence of SEQ ID NO: 40.

catA gene is not particularly limited so long as the gene is a gene expressing catechol 1,2-dioxygenase. Specific examples of catA gene include a gene having the nucleotide sequence of SEQ ID NO: 39. Catechol 1,2-dioxygenase (EC 1.13.11.1) is also referred to as 1,2-dihydroxybenzene 1,2-dioxygenase and so on. Catechol 1,2-dioxygenase is possessed, for example, by *Pseudomonas putida* KT2440 strain. Catechol 1,2-dioxygenase is generally known as an enzyme having the activity in catalyzing the reaction to synthesize cis, cis-muconic acid from catechol and requiring $Fe^{3+}$ as a cofactor.

Catechol 1,2-dioxygenase has an Intradiol dioxygenase domain in its amino acid sequence (Accession no. Q88I35). This domain is composed of [LIVMF]-x-G-x-[LIVM]-x(4)-[GS]-x(2)-[LIVMA]-x(4)-[LIVM]-[DE]-[LIVMFYC]-x(6)-G-x-[FY] (Prosite entry no. P00083), where Y in the sequence is involved in the binding of the cofactor $Fe^{3+}$. L137 to Y165 in the amino acid sequence of catechol 1,2-dioxygenase correspond to the above domain.

The transformed microorganism according to one aspect of the present invention (hereinafter referred to as transformed microorganism (1)) expresses at least aroY gene inserted. The transformed microorganism according to another aspect of the present invention (hereinafter referred to as transformed microorganism (2)) expresses at least aroY gene inserted and pcaHG gene inserted. In addition, when the transformed microorganism (2) lacks any one of pcaH gene and pcaG gene the host microorganism originally has on its chromosome, the lacking gene may be inserted and expressed, or both of pcaH gene and pcaG gene may be inserted and expressed in the transformed microorganism (2). On the other hand, the transformed microorganism of another aspect of the present invention (hereinafter referred to as transformed microorganism (3)) has neither aroY gene nor pcaHG gene inserted. In other words, the transformed microorganism (3) is not substantially able to produce muconic acid from protocatechuic acid. As used herein, when referring to the transformed microorganisms (1) to (3) collectively, they are simply referred to as "transformed microorganism". The transformed microorganism referred to in the part regarding a gene insertion refers to the transformed microorganism (1) and/or the transformed microorganism (2).

aroY gene is not particularly limited so long as the gene is a gene expressing protocatechuate decarboxylase. Specific examples of aroY gene include a gene having the nucleotide sequence of SEQ ID NO: 41. Protocatechuate decarboxylase (EC 4.1.1.63) is also known as 3,4-dihydroxybenzoate carboxy-lyase. Protocatechuate decarboxylase is not particularly limited so long as the enzyme catalyzes the reaction to synthesize catechol from protocatechuic acid. In addition, any enzymes that have the activity to catalyze the reaction to synthesize 3-methoxycatechol from 3-O-methylgallic acid or the reaction to synthesize pyrogallol from gallic acid may also be used as protocatechuate decarboxylase. Vanillic acid decarboxylase and decarboxylase of 4-hydroxybenzoic acid may be also used as protocatechuate decarboxylase, since they have the potential to decarboxylate protocatechuic acid. Protocatechuate decarboxylase is structurally classified into a group of proteins (UbiD superfamily) that contain the UbiD domain (Domain architecture ID 10487953).

Specific examples of protocatechuate decarboxylase include proteins (accession no. AB479384; AB479384 protein) derived from *Klebsiella pneumoniae* subsp. *pneumoniae* A170-40 strain (ATCC 25597 strain). Specific examples of proteins having an amino acid sequence with high sequence identity to the amino acid sequence of AB479384 protein include protocatechuate decarboxylase (accession no. AMJ70686; sequence identity 87.2%) from *Enterobacter cloacae* MBRL1077 strain and protocatechuate decarboxylase (accession no. CZU76022; sequence identity 85.7%) from *E. cloacae* e1026 strain, and other proteins registered as protocatechuate decarboxylase, but are not particularly limited to them. These enzymes are characterized as a group of enzymes that require $Mn^{2+}$ and prenylated flavin mononucleotide (prenyl-FMN) as cofactors.

The transformed microorganism may be one having kpdB gene inserted. kpdB gene is a gene expressing a protein that is assumed to synthesize prenyl-FMN, which is a cofactor of protocatechuate decarboxylase. It is probable that the expression of the protein together with protocatechuate decarboxylase in a cell enhances the supply of prenyl-FMN, resulting in improving the activity of protocatechuate decarboxylase. Therefore, it is assumed that if kpdB gene can be expressed along with aroY gene to improve the decarboxylation activity, the yield of muconic acid would increase.

kpdB gene is not particularly limited so long as the gene is a gene expressing 4-hydroxybenzoate decarboxylase subunit B having the enzymatic activity as flavin prenyltransferase. Specific examples of kpdB gene include a gene having the nucleotide sequence of SEQ ID NO: 42. There is phenolic acid (hydroxyarylic acid) decarboxylase subunit B in the UbiX family, and one of them is 4-hydroxybenzoate decarboxylase subunit B. The group of phenolic acid decarboxylases includes homo-oligomeric enzymes, such as AroY and Fdc (Ferulic acid decarboxylase from yeast) as well as hetero-oligomeric enzymes composed of BCD subunit, such as 4-hydroxybenzoate decarboxylase and vanillate decarboxylase.

Flavin prenyltransferase catalyzes the reaction to link the dimethylallyl moiety from dimethylallyl monophosphate (DMAP) to the flavin backbone of flavin mononucleotide (FMN) to synthesize prenyl-FMN.

Since 4-hydroxybenzoate decarboxylase subunit B is classified into the flavoprotein UbiX/Pad1 family, its amino acid sequence has, for example, 50% sequence identity to the amino acid sequence of Flavin prenyltransferase (UbiX) from *E. coli* K-12 strain (accession no. P0AG03); 39.8% sequence identity to the amino acid sequence of Flavin prenyltransferase (Pad1) from *S. cerevisiae* S288c strain (accession no. P33751); and 54.5% sequence identity to the amino acid sequence of phenolic acid decarboxylase subunit B (BcdB) from *B. subtilis* 168 strain (accession no. P94404). According to White MD et al. (Nature, 522:502-506, 2015; the entire description is incorporated by reference herein), S37 and R123, which are involved in the binding of FMN, and Y153 and R169, which are involved in the binding of DMAP, have been identified in the amino acid sequence of UbiX. The amino acid residues which are involved in the bindings of FMN and DMAP are conserved in the amino acid sequences of UbiX/Pad1 family proteins such as KpdB.

For the transformed microorganism, the host microorganism preferably has one, two, three or all of pcaH gene, pcaG gene, catA gene, and catB gene on its chromosome. As used herein, any one or both of vanA gene and vanB gene may be collectively referred to as vanAB gene. If the host microorganism does not have pobA gene, vanA gene and/or vanB gene on its chromosome, it is preferable to insert these genes into the transformed microorganism so as to express them. In addition, for the transformed microorganism, the host microorganism preferably has on its chromosome vanillin dehydrogenase (vdh) gene, p-hydroxybenzaldehyde dehydrogenase (PP 1948) gene and/or aldehyde dehydrogenase (ligV) gene from *Sphingobium* sp. SYK-6 strain. If the host microorganism does not have vdh gene, PP 1948 gene and/or ligV gene on its chromosome, it is preferable to insert these genes into the transformed microorganism so as to express them.

For the transformed microorganism, the host microorganism has the ability to grow (assimilate) using an aromatic compound derived from syringyl lignin such as syringic acid and syringaldehyde as a sole source of carbon. In order that the host microorganism has the ability to grow using an aromatic compound having a syringyl unit such as syringic acid and syringaldehyde as a sole carbon source, the host microorganism preferably has a gene that produces an enzyme for metabolizing syringic acid to pyruvic acid on its chromosome, including syringate O-demethylase gene (e.g., desA), 3-O-methylgallate 3,4-dioxygenase gene (e.g., desZ), 3-O-methylgallate O-demethylase gene (e.g., vanAB, ligM), 2-pyron-4,6-dicarboxylate hydrolase gene (e.g., ligI), gallate dioxygenase gene (e.g., desB), 4-oxalomethaconate tautomerase gene (e.g., ligU), 4-oxalomethaconate hydratase gene (e.g., ligJ), 4-carboxy-4-hydroxy-2-oxoadipate aldolase gene (e.g., ligK), and oxaloacetate decarboxylase gene (e.g., ligK). The gene that produces the enzyme for metabolizing syringic acid to pyruvic acid may be either individually or in combination of two or more of such genes. For example, if the host microorganism has the vanAB gene, it may not have to have desA gene or ligM gene.

pobA gene is not particularly limited so long as the gene is a gene expressing p-hydroxybenzoate monooxygenase. Specific examples of pobA gene include a gene having the nucleotide sequence of SEQ ID NO: 43. Examples of p-hydroxybenzoate monooxygenase (EC 1.14.13.2 or EC 1.14.13.33) include PobA (accession no. Q88H28) derived from *Pseudomonas putida* KT2440 strain.

vanA gene is not particularly limited so long as the gene is a gene expressing vanillate O-demethylase oxygenase component. Specific examples of vanA gene include a gene having the nucleotide sequence of SEQ ID NO: 44.

Examples of vanillate O-demethylase oxygenase component (EC 1.14.13.82) include VanA (accession no. Q88G16) derived from *Pseudomonas putida* KT2440 strain. The vanillate demethylase oxygenase component uses electrons derived from NADH or NADPH supplied via the oxidoreductase component, and oxygen atoms supplied by molecular oxygen to cleave a methyl ether bond of vanillic acid, resulting in protocatechuic acid, formaldehyde and water.

The vanillate O-demethylase oxygenase component has a Rieske [2Fe-2S] iron-sulfur domain (W7-V107, PROSITE entry no. PS51296) in its amino acid sequence, and the amino acids of C and H (C47, H49, C66, H69) in the domain are involved in the binding of Fe—S.

vanB gene is not particularly limited so long as the gene is a gene expressing vanillate O-demethylase oxidoreductase component. Specific examples of vanB gene include a gene having the nucleotide sequence of SEQ ID NO: 45.

Examples of vanillate O-demethylase oxidoreductase component (EC 1.14.13.82) include VanB (accession no. Q88GI5) derived from *Pseudomonas putida* KT2440 strain. The vanillate O-demethylase oxidoreductase component is known as one of the oxidoreductases that extract electrons from NADH or NADPH, and transfer them to an oxygenating enzyme (oxygenase). The vanillate O-demethylase oxidoreductase component transfers electrons derived from NADH or NADPH to VanA which is a vanillate O-demethylase oxygenase component.

The vanillate O-demethylase oxidoreductase component has 2Fe-2S Ferredoxin type iron-sulfur binding domain (G229-I316, PROSITE entry no. PS51085) in its amino acid sequence, and the amino acids of C (C265, C270, C273, and C303) in the amino acid sequence are involved in the binding of Fe—S. The vanillate O-demethylase oxidoreductase component has NAD-binding domain (L109-D201, Pfam entry no. PF00175) and Ferredoxin reductase type FAD-binding domain (M1-A101, PROSITE entry no. PS51384) in its amino acid sequence.

The expression products of vanA gene and vanB gene, VanAB, function as vanillate O-demethylases, but they may also be used as syringate O-demethylase and 3-O-methylgallate O-demethylase because they can convert syringic acid to 3-O-methylgallic acid and convert 3-O-methylgallic acid to gallic acid.

vdh gene is not particularly limited so long as the gene is a gene expressing vanillin dehydrogenase. Specific examples of vdh gene include a gene having the nucleotide sequence of SEQ ID NO: 51. Examples of vanillin dehydrogenase (EC 1.2.1.67) include Vdh (accession no. Q88HJ9) derived from *Pseudomonas* putida KT2440 strain.

PP 1948 gene is not particularly limited so long as the gene is a gene expressing p-hydroxybenzaldehyde dehydrogenase. Specific examples of PP 1948 gene include a gene having the nucleotide sequence of SEQ ID NO: 52. Examples of p-hydroxybenzaldehyde dehydrogenase (EC 1.2.1.64) include p-hydroxybenzaldehyde dehydrogenase (accession no. Q88LI4) from *Pseudomonas putida* KT2440 strain, and p-hydroxybenzaldehyde dehydrogenase (XylC, accession no. P43503) from *Pseudomonas putida* mt-2 strain.

ligV gene is not particularly limited so long as the gene is a gene expressing aldehyde dehydrogenase for which the substrate is any one of aromatic aldehydes such as vanillin, p-hydroxybenzaldehyde, syringaldehyde, protocatechuic aldehyde and benzaldehyde. Specific examples of ligV gene include a gene having the nucleotide sequence of SEQ ID NO: 53. Examples of aldehyde dehydrogenase (EC 1.2.1.-) include aldehyde dehydrogenase (accession no. AB287332) from *Sphingobium* sp. SYK-6 strain.

desA gene is not particularly limited so long as the gene is a gene expressing syringate O-demethylase. Specific examples of desA gene include a gene having the nucleotide sequence of SEQ ID NO: 54. Syringate O-demethylase is, for example, possessed by *Sphingobium* sp. SYK-6 strain, and has the activity to catalyze the reaction to synthesize 3-O-methylgallic acid from syringic acid.

ligM gene is not particularly limited so long as the gene is a gene expressing tetrahydrofolate-dependent vanillate/3-O-methylgallate O-demethylase. Specific examples of ligM gene include a gene having the nucleotide sequence of SEQ ID NO: 55.

For the transformed microorganism, the host microorganism preferably has vanA gene and vanB gene on its chromosome. If the host microorganism does not have vanA gene and vanB gene on its chromosome, it is preferable to insert these genes into the transformed microorganism so as to express them.

The genes to be inserted may not be completely identical to a gene that is originally retained by a source organism (i.e., wild-type gene). The gene to be inserted may be DNA that has a nucleotide sequence that hybridizes, under stringent condition, with a nucleotide sequence complementary to the nucleotide sequence of wild-type gene so long as the gene expresses a protein with the enzymatic property that is identical or very similar to that of the protein expressed by the wild-type gene (i.e., the wild-type protein).

The term "nucleotide sequence that hybridizes under stringent condition" as used herein means a nucleotide sequence of DNA obtained by hybridization system such as colony hybridization, plaque hybridization and Southern blot hybridization, using DNA having the nucleotide sequences of wild-type gene as a probe.

The term "stringent condition" as used herein refers to a condition in which a specific hybrid signal is clearly distinguished from a non-specific hybrid signal although the condition may vary depending on the hybridization system and the types, sequence, and length of probe to be used. Such condition may be determined by altering hybridization temperature, washing temperature, and salt concentration. For example, if a non-specific hybrid is disadvantageously detected as an intense signal, a hybridization specificity can be increased by elevating hybridization and washing temperatures and optionally lowering salt concentration during washing steps. If even any specific hybrids cannot be detected as a signal, the hybrids can be stabilized by lowering hybridization and washing temperatures and optionally increasing salt concentration during washing steps.

Specific examples of stringent condition include, for example, hybridization performed overnight (for about 8 hours to 16 hours) using a DNA probe as a probe and 5×SSC, 1.0% (w/v) blocking reagent for nucleic acid hybridization (Roche Diagnostics), 0.1% (w/v) N-lauroylsarcosine, and 0.02% (w/v) SDS. Washing is performed twice with 0.1× to 0.5×SSC and 0.1% (w/v) SDS, preferably 0.1×SSC and 0.1% (w/v) SDS for 15 minutes. The hybridization and washing temperatures are 65° C. or more, and preferably 68° C. or more.

DNA having a nucleotide sequence that hybridizes under stringent condition includes, for example, a DNA identified by performing hybridization under stringent conditions as described above using a filter on which a DNA or fragments of the DNA having the nucleotide sequence of wild-type gene derived from a colony or plaque are immobilized; and a DNA that can be identified by performing hybridization at a temperature from 40° C. to 75° C. in the presence of 0.5 M to 2.0 M NaCl, preferably at 65° C. in the presence of 0.7 M to 1.0 M NaCl followed by washing the filter with 0.1× to 1×SSC solution (1×SSC solution contains 150 mM sodium chloride and 15 mM sodium citrate) at 65° C. Probe preparation and hybridization techniques can be performed according to the methods as described in Molecular Cloning, A Laboratory Manual, 2nd-Ed., Cold Spring Harbor Laboratory, Cold Spring Harbor, NY., 1989; Current Protocols in Molecular Biology, Supplement 1-38, John Wiley & Sons, 1987-1997 (these literatures are also referred to as "technical literatures" hereinafter and are incorporated herein by reference in their entirety). It is understood that those skilled in the art would appropriately determine conditions for obtaining a DNA that has a nucleotide sequence hybridizing with a nucleotide sequence complementary to a nucleotide sequence of wild-type gene under stringent condition by taking account of conditions such as salt concentrations and temperatures of buffers as well as various other conditions including probe concentration, probe length and reaction time.

DNA having a nucleotide sequence that hybridizes under stringent condition includes a DNA having a particular percentage or higher sequence identity to the nucleotide sequences of a DNA having a nucleotide sequence of wild-type gene used as a probe, for example, DNA having 80% or more, preferably 85% or more, more preferably 90% or more, 91% or more, 92% or more, 93% or more, 94% or more, 95% or more, 96% or more, 97% or more, 98% or more, 99% or more, still more preferably 99.5% or more sequence identity to the nucleotide sequence of wild-type gene. The upper limit is not particularly limited, but is typically 100%.

Nucleotide sequences of DNA that hybridize, under stringent condition, with DNA consisting of a nucleotide sequence complementary to a nucleotide sequence of wild-type gene include, for example, nucleotide sequences having one to several, preferably 1 to 20, more preferably 1 to 15, still more preferably 1, 2, 3, 4, 5, 6, 7, 8, 9, or 10 nucleotides deleted, substituted, and/or added per unit in the nucleotide sequence of wild-type gene when 100 nucleotides in a nucleotide sequence are considered as one unit. The term "nucleotide deleted" means a loss or disappearance of a nucleotide in a sequence; the term "nucleotide substituted" means replacement of a nucleotide with another nucleotide in a sequence; the term "nucleotide added" means addition of a new nucleotide inserted into a sequence.

While a protein encoded by a nucleotide sequence that hybridizes with a nucleotide sequence complementary to the nucleotide sequence of the wild-type gene under stringent condition may be a protein having an amino acid sequence resulting from deletion, substitution, addition or other modification of one to several amino acids in the amino acid sequence of the protein encoded by the nucleotide sequence of the wild-type gene, it has the same activities and/or functions as the protein encoded by the nucleotide sequence of the wild-type gene.

The protein having the enzymatic property identical or similar to that of the wild-type protein may be a protein that consists of an amino acid sequence having one or several amino acids deleted, substituted, and/or added in the amino acid sequence of the wild-type protein. The range of "one or several amino acids" in the phrase "having one or several amino acids deleted, substituted, and/or added" in the amino acid sequences is not particularly limited, but means for example 1, 2, 3, 4, 5, 6, 7, 8, 9, 10, 11, 12, 13, 14, 15, 16, 17, 18, 19, or 20, preferably about 1, 2, 3, 4, 5, 6, 7, 8, 9, or 10, and more preferably about 1, 2, 3, 4, or 5 amino acids per unit when 100 amino acids in an amino acid sequence are considered as one unit. As used herein, the term "amino acid deleted" means a loss or disappearance of an amino acid residue in a sequence; the term "amino acid substituted" means replacement of an amino acid residue with another amino acid residue in a sequence; the term "amino acid added" means addition of a new amino acid residue inserted into a sequence.

Embodiments of the "one or several amino acids deleted, substituted, and/or added" include an aspect in which one or several amino acids have been substituted with other chemically similar amino acids. For example, a hydrophobic amino acid may be substituted with another hydrophobic amino acid, or a polar amino acid may be substituted with another polar amino acid having the same charge. Such chemically similar amino acids are known in the art for each amino acid. Specific examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of positively charged basic amino acids include arginine, histidine, and lysine. Examples of negatively charged acidic amino acids include aspartic acid, and glutamic acid.

Examples of amino acid sequences resulting from deletion, substitution, addition or other modification of one or several amino acids in the amino acid sequence of the wild-type protein include amino acid sequences having a particular percentage or higher sequence identity to the amino acid sequence of the wild-type protein, such as amino acid sequences having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the amino acid sequence of the wild-type protein. The upper limit is not particularly limited, but is typically 100%.

(Means for Calculating Sequence Identity)

While methods for determining sequence identity of nucleotide and amino acid sequences are not particularly limited, the sequence identity can be determined by aligning a nucleotide sequence of a wild-type gene or an amino acid sequence of a protein encoded by a wild-type gene with a nucleotide or amino acid sequence of interest, and using programs that calculate the match rate between the sequences, for example, using generally known methods.

The programs that calculate the match rate between two amino acid sequences or nucleotide sequences include, for example, the algorithm of Karlin and Altschul (Proc. Natl. Acad. Sci. USA 87, 2264-2268, 1990; Proc. Natl. Acad. Sci. USA 90, 5873-5877, 1993, incorporated herein by reference in their entirety) known in the art. BLAST program using this algorithm was developed by Altschul et al. (J. Mol. Biol. 215, 403-410, 1990, incorporated herein by reference in its entirety). Gapped BLAST which determines sequence identity more sensitively than BLAST is also known (Nucleic Acids Res. 25, 3389-3402, 1997, incorporated herein by reference in its entirety). Thus, those skilled in the art can search for sequences having high sequence identity to a given sequence in the database using, for example, the programs as described above. These programs are available, for example, on the website of The National Center for Biotechnology Information (http://blast.ncbi.nlm.nih.gov/Blast.cgi) on the Internet.

While each of the methods as described above can be generally used to search for sequences having sequence identity in the database, Genetyx network version 12.0.1 (Genetyx) can be also used for homology analysis as a means for determining sequence identity of an individual sequence. This method is based on the Lipman-Pearson method (Science 227, 1435-1441, 1985, incorporated herein by reference in its entirety). Upon analysis of sequence identity of nucleotide sequences, regions encoding a protein (CDS or ORF) are used if possible.

(Origin of Gene to be Inserted)

The gene to be inserted is derived from a microorganism that possesses the gene to be inserted and a microorganism closely related to the microorganism. Examples of microorganisms from which the gene to be inserted is derived include microorganisms that can produce muconic acid from protocatechuic acid and microorganisms that can grow by assimilating protocatechuic acid.

Specific examples of microorganisms from which the gene to be inserted originate include, but not limited to, for pcaH gene and pcaG gene, microorganisms of the genus *Pseudomonas* such as *Pseudomonas putida, Pseudomonas plecoglossicida, Pseudomonas taiwanensis, Pseudomonas monteilii, Pseudomonas fulva, Pseudomonas fluorescens, Pseudomonas alcaligenes, Pseudomonas pseudoalcaligenes, Pseudomonas mendocina, Pseudomonas aeruginosa,* and *Pseudomonas cepacia,* and microorganisms of the genus *Acinetobacter* such as *Acinetobacter bailey* and *Acinetobacter calcoaceticus*; for catA gene, microorganisms of the genus *Pseudomonas* such as *Pseudomonas putida, Pseudomonas plecoglossicida, Pseudomonas taiwanensis, Pseudomonas monteilii, Pseudomonas fulva, Pseudomonas aeruginosa, Pseudomonas fluorescens,* and *Pseudomonas reinekei,* microorganisms of the genus *Acinetobacter* such as *Acinetobacter calcoaceticus* and *Acinetobacter radioresistens,* microorganisms of the genus *Rhodococcus* such as *Rhodococcus opacus, Rhodococcus pyridinivorans* and *Rhodococcus rhodochrous*; for aroY gene, microorganisms of the genus *Klebsiella* such as *Klebsiella pneumoniae, Klebsiella oxytoca, Klebsiella quassin pneumoniae,* microorganisms of the genus *Enterobacter* such as *Enterobacter cloacae* and *Enterobacter aerogenes,* and *Sedimentobacter hydroxybenzoicus*; for pobA gene, microorganisms of the genus *Pseudomonas* such as *Pseudomonas putida, Pseudomonas plecoglossicida, Pseudomonas taiwanensis, Pseudomonas monteilii, Pseudomonas fulva, Pseudomonas fluorescens,* and *Pseudomonas aeruginosa,* microorganisms of the genus *Acinetobacter* such as *Acinetobacter bailey, Acinetobacter calcoaceticus* and *Acinetobacter baumannii,* and microorganisms of the genus *Klebsiella* such as *Klebsiella pneumoniae* and *Klebsiella variicola*; for catA gene and catB gene, microorganisms of the genus *Pseudomonas* such as *Pseudomonas putida, Pseudomonas plecoglossicida, Pseudomonas taiwanensis, Pseudomonas monteilii, Pseudomonas fulva, Pseudomonas fluorescens, Pseudomonas resinovorans,* and *Pseudomonas aeruginosa,* microorganisms of the genus *Comamonas* such as *Comamonas testosteroni* and *Comamonas thiooxidans* and microorganisms of the genus *Acetobacter* such as *Acetobacter pasteurianus, Acetobacter aceti* and *Acetobacter tropicalis*; for vdh gene, microorganisms of the genus *Pseudomonas* such as *Pseudomonas putida, Pseudomonas plecoglossicida, Pseudomonas taiwanensis, Pseudomonas monteilii, Pseudomonas fulva, Pseudomonas fluorescens,* and *Pseudomonas syringae,* microorganisms of the genus *Rhodococcus* such as *Rhodococcus jostii* and *Rhodococcus erythropolis,* microorganisms of the genus *Burkholderia* such as *Burkholderia cepacia* and *Burkholderia cenocepacia,* and microorganisms of the genus *Sphingobium* such as *Sphingobium* species; for PP 1948 gene, microorganisms of the genus *Pseudomonas* such as *Pseudomonas putida, Pseudomonas plecoglossicida, Pseudomonas taiwanensis, Pseudomonas monteilii, Pseudomonas fulva, Pseudomonas mendocina, Pseudomonas fluorescens,* and *Pseudomonas syringae,* microorganisms of the genus *Sphingobium* such as *Sphingobium yanoikuyae* and *Sphingobium* species, microorganisms of the genus *Rhodococcus* such as *Rhodococcus jostii* and *Rhodococcus erythropolis,* microorganisms of the genus *Burkholderia* such as *Burkholderia cepacia* and *Burkholderia cenocepacia*; for ligM gene and desA gene, microorganisms of the family Sphingomonadaceae such as *Sphingobium* species, *Sphingomonas* species, *Novosphingobium aromaticivorans, Altererythrobacter* species and *Erythrobacter* species, microorganisms of the genus *Arthrobacter* such as *Arthrobacter castelli* and *Arthrobacter* species, and microorganism of the family Microbacteriaceae such as *Leifsonia* species, microorganism of the family Micrococcaceae such as *Kocuria polaris, Kocuria* species, *Neomicrococcus aestuarii, Paeniglutamicibacter gangotriensis, Citrococcus* species, and *Tersicoccus* species, and microorganisms of the family Microbacteriaceae such as *Microbacterium* species.

As described above, while the organism of origin from which the inserted gene is derived are not particularly limited, it is required that the inserted genes expressed in the transformant are not be inactivated by the growth conditions of the host organism or the genes show its activity. For this reason, it is desirable that the organism of origin from which the inserted gene is derived is a host organism to be transformed by the insertion of the gene or a microorganism that grows under conditions similar to the growth conditions of the host organism. In other words, the organism of origin from which the inserted gene is derived is preferably a microorganism of the genus *Pseudomonas, Sphingobium, Klebsiella, Acinetobacter, Rhodococcus, Enterobacter, Acetobacter* or *Burkholderia*.

(Cloning of Gene to be Inserted with the use of Genetic Engineering Techniques)

The gene to be deleted or inserted can be inserted into various suitable known vectors. The resulting vector can then be introduced into a suitable known host organism to create a transformant (transformed microorganism) in which the gene has been deleted or inserted. The gene to be deleted is preferably a gene which is disrupted, deleted, replaced, or inserted within the whole or part of the gene, resulting in a change in the structure of the gene. The gene to be inserted is preferably a gene that expresses a protein that is identical or similar to the wild-type gene.

A person skilled in the art can appropriately select a suitable method for obtaining the gene to be deleted or inserted, a method for obtaining the information on the nucleotide sequence of the gene and the amino acid sequence of the protein encoded by the gene, as well as a method for creating different vectors and a method for creating a transformed microorganism. As used herein, examples of transformation and transformant include transduction and transductant, respectively. One non-limiting example of cloning of the genes to be deleted and inserted will be described below.

For example, using a standard technique such as the technique described in the reference literature, the chromosomal DNA and mRNA can be extracted from an organism of origin or any one of various microorganisms, which has a wild-type gene involved in a gene to be deleted or inserted. By using the extracted mRNA as a template, cDNA can be synthesized. The chromosomal DNA and cDNA thus obtained can be used to produce a library of chromosomal DNA and cDNA.

For example, a gene to be inserted can be obtained by cloning from the chromosomal DNA or cDNA derived from an organism of origin having a wild-type gene involved in the gene, which serves as a template. The organisms of origin from which the wild-type gene is derived are as described above. Specific examples of the organisms include, but are not limited to, *Pseudomonas putida* KT2440 strain, *Klebsiella pneumoniae* subsp. *pneumoniae* A170-40 strain, and *Pseudomonas* sp. NGC7 strain, depending on the type of the gene. For example, *Pseudomonas putida* KT2440 strain is cultured and the resulting cells are dehydrated and physically ground to fine powder in a mortar or the like while cooling in liquid nitrogen. Subsequently, a chromosomal DNA fraction is extracted from the fine powder of the cells using typical techniques. A commercially available chromosomal DNA extraction kit such as DNeasy Blood & Tissue Kit (Qiagen) may be used to extract the chromosomal DNA. As used herein, chromosomal DNA and genomic DNA are synonymous.

The chromosomal DNA is then used as a template to amplify DNA by a polymerase chain reaction (hereinafter denoted as "PCR") using synthetic primers complementary to 5'- and 3'-terminal sequences. The primers are not particularly limited so long as they can amplify a DNA fragment containing the gene to be inserted. Examples of the primers for pcaH gene and pcaG gene include primers shown in SEQ ID Nos: 1 and 2 designed in reference to the genome sequence of Pseudomonas putida KT2440 strain. These primers can amplify the full length of the target gene. In other methods, a target gene clone from a shotgun library can be screened, or DNA containing gene fragments of interest are amplified by suitable PCR such as Inverse PCR, Nested PCR, 5' RACE and 3' RACE, and these amplified DNA fragments are then ligated to obtain a DNA containing a full-length gene of interest.

While the methods for obtaining the gene to be deleted or inserted are not particularly limited, examples of the methods include not only methods using genetic engineering techniques but also methods using chemical synthesis techniques with which the gene can be constructed.

Nucleotide sequences of products amplified by PCR and chemically synthesized genes can be confirmed, for example, as follows. First, the DNA fragment to be sequenced is inserted into a suitable vector according to the standard technique to prepare a recombinant DNA. For cloning into a vector, the following kits and vectors may be used: known or commercially available kits, such as In-Fusion HD Cloning Kit (Takara Bio), TA Cloning Kit (Invitrogen); known or commercially available plasmid vectors, such as pUC4K (see Gene,vol. 19, p259-268, 1982; the entire description is incorporated by reference herein), pEX18Amp (see Gene,vol. 212,p77-86,1998; the entire description is incorporated by reference herein), pPS858 (see Gene,vol.212,p77-86,1998; the entire description is incorporated by reference herein), pUC118 (Takara Bio), pJB866 (see Plasmid,vol.38,p35-51,1997; the entire description is incorporated by reference herein), pMCL200 (see Gene,vol.162,p157-158,1995; the entire description is incorporated by reference herein), pQE30 (Qiagen), pUC119 (Takara Bio), pUC18 (Takara Bio), and pBR322 (Takara Bio); known or commercially available bacteriophage vectors, such as AEMBL3 (Stratagene), and pAK405 (Andreas Kaczmarczyk et al., Applied and Environmental Microbiology, 2012, 78 (10) 3774-3777; the entire description is incorporated by reference herein).

If a large number of the constructed recombinant DNA is required, for example, Escherichia coli, preferably Escherichia coli JM109 strain (Takara Bio) or Escherichia coli DH5a strain (Takara Bio) may be transformed with the recombinant DNA. Then, the recombinant DNA present in the resulting transformant may be purified using QIAGEN Plasmid Mini Kit (QIAGEN) or other suitable kits.

The nucleotide sequence of each gene inserted into the recombinant DNA is determined by the dideoxy method (Methods in Enzymology, 101, 20-78, 1983, incorporated herein by reference in its entirety) or the like. While sequencers used to determine the nucleotide sequence are not particularly limited, examples of sequencers include Li-COR MODEL 4200L sequencer (Aloka), 370DNA sequencing system (Perkin Elmer), CEQ2000XL DNA analysis system (Beckman), and the like. The determined nucleotide sequence may then be used to estimate the amino acid sequence of the translated protein.

(Construction of Recombinant Vector Containing Gene)

A recombinant vector containing a gene to be deleted or inserted (recombinant DNA) can be constructed by ligating a PCR amplification product containing a gene to be deleted or inserted with any of various vectors in such a way that the gene can be deleted or expressed. In the case of the gene to be deleted, the recombinant vector preferably contains the upstream and downstream regions of the gene to be deleted since the recombinant vector is introduced into the host microorganism and a gene in the recombinant vector is replaced with the gene in the host microorganism by homologous recombination.

In a non-limiting example of the method of preparing a recombinant vector containing a gene to be inserted, the recombinant vector can be constructed by excising a DNA fragment containing any one of genes to be inserted with a suitable restriction enzyme, and then ligating the DNA fragment with a plasmid vector excised with a suitable restriction enzyme, using a commercially available recombinant vector preparation kit such as In-Fusion HD Cloning Kit (Takara Bio). Alternatively, the recombinant vector may also be obtained by ligating a DNA fragment, which contains the gene and has sequences homologous to a plasmid vector attached to the both ends of the DNA fragment, to another DNA fragment derived from the plasmid amplified by inverse PCR with the use of a commercially available recombinant vector preparation kit such as In-Fusion HD Cloning Kit (Takara Bio).

The recombinant vector containing a gene to be deleted or inserted contains at least the gene to be deleted or inserted and the gene (nucleotide sequence) derived from a plasmid vector. Examples of such recombinant vectors include a recombinant vector containing aroY gene; and a recombinant vector containing aroY gene and pcaH gene and/or pcaG gene. In addition to aroY gene and pcaHG gene, the recombinant vector may contain at least one, two, three, or four genes selected from the group consisting of pobA gene, vanAB gene, vdh gene, and PP_1948 gene. The recombinant vector may also contain genes other than those mentioned above, so long as the problem of the present invention can be solved.

The recombinant vector preferably contains a heterologous gene or a heterologous nucleotide sequence. The heterologous gene is not particularly limited, so long as the gene is not naturally occurring in the host microorganism. Examples of such heterologous genes include a synthetic gene which is not based on the nucleotide sequence derived from the host microorganism, a gene derived from another organism different from the organism of origin from which the gene to be inserted is derived, and a gene derived from another organism, e.g., a plant, an animal, a virus, or another microorganism, which is different from the host microorganism. When the host microorganism is a Pseudomonas microorganism, specific examples of such heterologous genes include, but are not limited to, a DNA fragment derived from pUC118, e.g., the lactose promoter region (Plac).

Specific examples of such recombinant vectors include, but are not limited to, pTS110 plasmid vector, pTS119 plasmid vector, and pTS084 plasmid vector, which are described in Examples below.

(Method of Producing Transformed Microorganism)

While the methods of producing a transformed microorganism are not particularly limited, examples of the methods include a method including introducing a gene into a host microorganism according to known methods in such a way that the deletion or insertion of gene is achieved. Specifically, constructed is a DNA construct having a gene inserted between an expression-inducing promoter and a terminator. Subsequently, a host organism is transformed with the DNA construct to obtain a transformed microorganism expressing the gene inserted. Alternatively, constructed is a DNA construct having a gene to be deleted and the upstream and downstream regions of the gene. Subsequently, a host organism is transformed with the DNA construct to obtain a transformed microorganism lacking the gene. As used herein, recombinant vectors which are prepared to transform a host microorganism are collectively referred to as DNA construct.

The methods of introducing the DNA construct into a host microorganism are not particularly limited. Examples of the methods include known methods to those skilled in the art; such as a method in which the DNA construct is introduced to autonomously replicate, and to express the gene; and a method of introducing the DNA construct directly into the chromosome of the host organism due to homologous recombination.

In the method using homologous recombination for introducing the DNA construct containing the gene to be inserted into a host microorganism, the DNA construct that has been ligated between regions homologous to upstream and downstream regions from a recombination site on its chromosome can be inserted into the genome of the host organism.

The vector-host systems used to prepare the transformed microorganism are not particularly limited so long as the gene to be inserted can be expressed in the host microorganism, or the gene on the chromosome of the host microorganism can be deleted. Examples of the systems include pJB866-*Pseudomonas* microorganism system, and pKT239 (Gene, vol. 16, p237-247, 1981; incorporated herein by reference in its entirety)-*Pseudomonas* microorganism system.

The DNA construct containing the gene inserted may autonomously replicate and express the gene in the form that the DNA construct is not introduced into the chromosome of the host organism, or may express the gene in the form that the DNA construct is introduced into the chromosome of the host microorganism.

The DNA construct may contain a marker gene that allows the selection of transformed cells. While the marker gene is not particularly limited, examples of such marker genes include antibiotic resistance genes that correspond to antibiotics such as gentamicin, kanamycin, tetracycline, ampicillin, and carbenicillin. The marker gene may be contained in the middle of the gene to be deleted or to be replaced with the gene to be deleted.

Depending on the type of gene, the DNA construct containing the gene to be inserted may contain a promoter, a terminator, and other regulatory sequences (such as a cis-sequence involved in transcriptional regulation like an operator), which enable the expression of the gene in the host microorganism.

Specific examples of such DNA constructs include, but are not particularly limited to, pTS108 plasmid vector, pTS110 plasmid vector, and pTS084 plasmid vector, which are described in Examples below.

The methods of transforming a microorganism of the genus *Pseudomonas* may be properly selected from any methods known to those skilled in the art. Examples of the methods include electroporation method and conjugational transfer method.

The medium for selecting and culturing the transformed microorganism is appropriately selected depending on the host microorganism and the marker gene to be used. For example, when *Pseudomonas putida, Pseudomonas plecoglossicida, Pseudomonas taiwanensis, Pseudomonas monteilii, Pseudomonas fulva* or their closely related species *Pseudomonas* species is used as a host microorganism, and an antibiotic resistance gene to kanamycin, gentamicin or tetracycline is used as a marker gene, the selection and growth of the transformed microorganism can be carried out, for example, by culturing the transformed microorganism in LB medium containing the above drug. The term "closely related species" herein refers to a microorganism of the genus *Pseudomonas* (*Pseudomonas* species) having the 16S rRNA gene sequence with 99.0% to 99.9% sequence identity to that of at least one species among *Pseudomonas putida, Pseudomonas plecoglossicida, Pseudomonas taiwanensis, Pseudomonas monteilii* and *Pseudomonas fulva*.

The successful production of the transformed microorganism may be confirmed, for example, by culturing the transformed microorganism under conditions where only the transformed microorganism lacking the gene can grow or only the transformed microorganism expressing the gene inserted can grow. Alternatively, the successful production of the transformed microorganism may be confirmed, for example, by culturing the transformed microorganism, and then confirming that the amount of muconic acid in the resulting broth is larger than that in the broth obtained by culturing the host microorganism under the same condition.

The production of the transformed microorganism may be also confirmed by the following procedure: the chromosomal DNA is extracted from the transformed microorganism, and PCR is performed using the chromosomal DNA as a template to detect the presence of any PCR products that can be amplified if the transformation has occurred and to confirm the property and nucleotide sequence of the PCR product.

For example, PCR can be performed using a pair of a forward primer for the nucleotide sequence of the promoter of gene to be deleted or inserted and a reverse primer for the nucleotide sequence of the marker gene, and whether the product having an expected length is produced is determined.

When the transformation is carried out by homologous recombination, it is preferred to perform PCR using a pair of a forward primer located upstream from the upstream homologous region used and a reverse primer located downstream from the downstream homologous region used, and then to determine whether the product having a length expected when the homologous recombination has occurred is produced.

(Host Microorganism)

The host microorganism is not particularly limited, so long as it is any *Pseudomonas* microorganism that has pcaH gene, pcaG gene, catA gene and catB gene on its chromosome, and can assimilate an aromatic compound derived from syringyl lignin. Preferred examples of such host microorganisms include microorganisms of the genus *Pseudomonas* that has pcaH gene, pcaG gene, catA gene, catB gene, pobA gene, vanA gene, vanB gene, vdh gene and PP 1948 gene on its chromosome, and is capable of assimilating an aromatic compound derived from syringyl lignin, such as *Pseudomonas putida, Pseudomonas fluorescens, Pseudomonas aeruginosa, Pseudomonas plecoglossicida, Pseudomo-* nas taiwanensis, Pseudomonas monteilii, Pseudomonas fulva and their closely related species (Pseudomonas species). More preferred examples of the host microorganisms include Pseudomonas putida and its closely related species Pseudomonas species, which have the above genes on its chromosome, and can assimilate an aromatic compound derived from syringyl lignin and producing muconic acid from protocatechuic acid.

The methods of obtaining the host microorganism are not particularly limited. Examples of the methods include a method including, as described in Examples below, obtaining microorganisms in natural samples such as soil, preferably soil obtained by getting dug up about 5 cm to 10 cm from the surface near the root of broad leaf trees and then isolating the microorganism using a medium for Pseudomonas microorganisms that contains syringic acid as a sole carbon source, a method purchasing and using commercially available collection strains, and a method receiving individually managed strains.

Whether or not the host microorganism can assimilate an aromatic compound derived from syringyl lignin may be confirmed by the following procedures as described in Examples below: for example, evaluating the presence or absence of the host microorganism grown in the case where the host microorganism is cultured using a medium for Pseudomonas microorganisms containing an aromatic compound derived from syringyl lignin as a sole carbon source.

With reference to Examples described below, a person skilled in the art with experience in isolating a Pseudomonas microorganism can isolate Pseudomonas microorganisms from nature samples, and further obtain from them a Pseudomonas microorganism that can assimilate an aromatic compound derived from syringyl lignin.

For example, populations of Pseudomonas microorganisms are obtained from soil obtained by getting dug up about 5 cm to 10 cm from the surface near the root of broad leaf trees. The microorganisms in the soil are cultured using Wx liquid medium containing 5 mM syringic acid as a sole carbon source. The resulting culture broth is subcultured in fresh Wx liquid medium containing 5 mM syringic acid as a sole carbon source. After repeating this procedure several more times, the resulting culture broth is streaked onto Wx agar medium containing 5 mM syringic acid as a sole carbon source, and incubated statically. Colonies formed onto the agar medium are isolated, and the strains that are sensitive to antibiotics are selected. The selected strains are then cultured in Wx liquid medium containing 10 mM syringic acid as a sole carbon source, and among them, a Pseudomonas microorganism that shows excellent growth is used as the host microorganism. As used herein, the term "excellent growth" means, for example, that the absorbance (660 nm) of the culture broth obtained when the microorganism is cultured at 30° C. for 48 hours becomes two times or more (e.g., 0.1 or more) as compared to the absorbance before culture (e.g., 0.05).

(Specific Examples of Gene to be Deleted or Inserted)

As for the gene to be deleted or inserted, specific examples of pcaH gene, pcaG gene, catA gene, catB gene, pobA gene, vanA gene and vanB gene include pcaH gene, pcaG gene, catA gene, catB gene, pobA gene, vanA gene, and vanB gene possessed by Pseudomonas putida KT2440 strain, and the nucleotide sequences of the genes correspond to those described in SEQ ID NOs: 37 to 40, and 43 to 45, respectively. Similarly, specific examples of aroY gene include aroY gene possessed by Klebsiella pneumoniae subsp. pneumoniae A170-40 strain, and the nucleotide sequence which is shown in SEQ ID NO: 41. Specific examples of kpdB gene include kpdB gene possessed by Klebsiella pneumoniae subsp. pneumoniae NBRC14940 strain, and the nucleotide sequence which is shown in SEQ ID NO: 42. The amino acid sequences of the proteins expressed by these genes are listed in SEQ ID NOs: 33 to 36, and 46 to 50, respectively.

The methods of obtaining genes to be deleted or inserted from microorganisms other than those mentioned above are not particularly limited. For example, BLAST homology search may be conducted on the genomic DNA of a target organism using the nucleotide sequences of pcaH gene, pcaG gene, catA gene, catB gene, pobA gene, vanA gene, and vanB gene possessed by Pseudomonas putida KT2440 strain (SEQ ID NOs: 37 to 40, and 43 to 45); and the nucleotide sequence of aroY gene possessed by Klebsiella pneumoniae subsp. pneumoniae A170-40 strain (SEQ ID NO: 41) to identify a gene having a nucleotide sequence with a high sequence identity to any one of the above sequences. Alternatively, the gene to be deleted or inserted may be obtained by identifying a protein having an amino acid sequence having a high sequence identity to any one of the amino acid sequences (SEQ ID NOs: 33 to 36, and 46 to 50) of proteins expressed by the genes from the total proteins in another microorganism, and identifying the gene encoding the identified protein. Whether the resulting gene corresponds to the gene to be deleted or isolated may be confirmed by transforming the microorganism originally having the gene as the host microorganism and evaluating the enhanced productivity of muconic acid of the transformed microorganism as compared to that of the host microorganism.

Since Pseudomonas putida, Pseudomonas plecoglossicida, Pseudomonas taiwanensis, Pseudomonas monteilii, Pseudomonas fulva, Pseudomonas fluorescens and Pseudomonas aeruginosa have similar growth conditions, there is a probability that they can be mutually transformed by inserting the gene possessed by each of them. For example, the transformed microorganism may be obtained by introducing the gene obtained from Pseudomonas putida into Pseudomonas plecoglossicida, Pseudomonas taiwanensis, Pseudomonas monteilii, Pseudomonas fulva, Pseudomonas fluorescens or Pseudomonas aeruginosa as the host microorganism. It may be able to introduce and express the gene obtained from Pseudomonas putida into the microorganism of the genus Klebsiella, Enterobacter, Escherichia or Sphingobium as the host microorganism. The gene to be inserted may be a gene optimized for its codons, secondary structure and GC contents in order to get expressed in the host microorganism.

(Specific Aspects of Transformed Microorganism)

One specific aspect of the transformed microorganism (1) is a transformed Pseudomonas microorganism wherein the host microorganism is Pseudomonas microorganism selected from the group consisting of Pseudomonas putida, Pseudomonas plecoglossicida, Pseudomonas taiwanensis, Pseudomonas monteilii, Pseudomonas fulva and their closely related Pseudomonas species, which are capable of assimilating an aromatic compound derived from syringyl lignin; and the transformed Pseudomonas microorganism lacks both pcaH gene or pcaG gene and catB gene on its chromosome and expresses aroY gene inserted. Another specific aspect of the transformed microorganism (1) is a transformed Pseudomonas microorganism wherein the host microorganism is Pseudomonas putida or Pseudomonas species, which can assimilate an aromatic compound derived from syringyl lignin; and the transformed

*Pseudomonas* microorganism lacks all pcaH gene, pcaG gene and catB gene on its chromosome and expresses aroY gene inserted.

One specific aspect of the transformed microorganism (2) is a transformed *Pseudomonas* microorganism wherein the host microorganism is *Pseudomonas* microorganism selected from the group consisting of *Pseudomonas putida, Pseudomonas plecoglossicida, Pseudomonas taiwanensis, Pseudomonas monteilii, Pseudomonas fulva*, and their closely related *Pseudomonas* species, which are capable of assimilating an aromatic compound derived from syringyl lignin; and the transformed *Pseudomonas* microorganism lacks both pcaH gene or pcaG gene and catB gene on its chromosome, expresses aroY gene inserted, and expresses pcaH gene or pcaG gene inserted corresponding to pcaH gene or pcaG gene deleted. Another specific aspect of the transformed microorganism (2) is a transformed *Pseudomonas* microorganism wherein the host microorganism is *Pseudomonas putida* or *Pseudomonas* species, which can assimilate an aromatic compound derived from syringyl lignin; and the transformed *Pseudomonas* microorganism lacks all pcaH gene, pcaG gene, and catB gene on its chromosome, and expresses pcaH gene, pcaG gene, and aroY gene inserted.

Another specific aspect of transformed microorganisms (1) and (2) is a transformed *Pseudomonas* microorganism that expresses at least one gene selected from the group consisting of pobA gene, catA gene, vanA gene, and vanB gene inserted with respect to the above transformed *Pseudomonas* microorganism.

Each of the transformed microorganisms (1) and (2) lacks pcaH gene and/or pcaG gene and catB gene on its chromosome, and expresses aroY gene inserted so that the transformed microorganism can grow and produce muconic acid by using as carbon sources aromatic compounds derived from guaiacyl lignin such as vanillic acid and/or derived from p-hydroxyphenyl lignin such as p-hydroxybenzoic acid, and an aromatic compound derived from syringyl lignin such as syringic acid. The transformed microorganism of Non-patent document 1 cannot grow and produce muconic acid by using the above aromatic compounds. The transformed microorganism (2) lacks pcaH gene and/or pcaG gene and catB gene on its chromosome, expresses aroY gene inserted, and expresses pcaH gene and/or pcaG gene inserted corresponding to pcaH gene and/or pcaG gene deleted so that the transformed microorganism can grow and produce muconic acid by using an aromatic compound derived from guaiacyl lignin or derived from p-hydroxyphenyl lignin as a source of carbon. As described in Examples below, each preferred aspect of the transformed microorganisms (1) and (2) is a transformed microorganism that overexpresses catA gene, vanA gene, and vanB gene inserted in view of the ability of assimilating aromatic compounds derived from lignin.

Specific examples of the transformed microorganisms (1) and (2) include, but are not limited to, NGC7ΔpcaHGΔcatB/pTS110 strain, NGC7ΔpcaHGΔcatB/pTS119 strain, and NGC7ΔpcaHGΔcatB/pTS084 strain, as described in Examples below.

One specific aspect of the transformed microorganism (3) is a transformed *Pseudomonas* microorganism wherein the host microorganism is *Pseudomonas* microorganism selected from the group consisting of *Pseudomonas putida, Pseudomonas plecoglossicida, Pseudomonas taiwanensis, Pseudomonas monteilii, Pseudomonas fulva* and their closely related *Pseudomonas* species, which are capable of assimilating an aromatic compound derived from syringyl lignin; and the transformed *Pseudomonas* microorganism lacks pcaH gene or pcaG gene on its chromosome. Another specific aspect of the transformed microorganism (3) is a transformed *Pseudomonas* microorganism wherein the host microorganism is *Pseudomonas putida* or *Pseudomonas* species, which can assimilate an aromatic compound derived from syringyl lignin; and the transformed *Pseudomonas* microorganism lacks all pcaH gene and pcaG gene on its chromosome.

The transformed microorganism (3) lacks pcaH gene and/or pcaG gene on its chromosome so that the transformed microorganism can grow by using an aromatic compound derived from syringyl lignin and produce protocatechuic acid from aromatic compounds derived from guaiacyl lignin and/or derived from p-hydroxyphenyl lignin.

Specific examples of the transformed microorganism (3) include, but are not limited to, NGC7ΔpcaHGΔcatB strain, as described in Examples below.

In addition, JP 2010-207094 A discloses the preparation of the transformed microorganism wherein the host microorganism is *Pseudomonas putida*, and pcaHG gene and the protocatechuate 5-position oxidase gene on its chromosome were disrupted or mutated, and tpaK gene, tpaAa gene, tpaAb gene, tpaB gene, and tpaC gene inserted were expressed; the growth of the transformed microorganism using glucose; and the subsequent production of protocatechuic acid using terephthalic acid. However, in JP 2010-207094 A, protocatechuic acid has not been produced from lignin or an aromatic compound derived from lignin.

(Production Method)

One aspect of the production method according to the present invention (hereinafter referred to as production method (1)) is a method of producing muconic acid, including at least applying aromatic compounds derived from guaiacyl lignin such as vanillic acid and/or p-hydroxyphenyl lignin such as p-hydroxybenzoic acid, and an aromatic compound derived from syringyl lignin such as syringic acid to the transformed microorganisms (1) and/or (2), thereby obtaining muconic acid.

Another aspect of the production method according to the present invention (hereinafter referred to as production method (2)) is a method of producing muconic acid, including at least applying aromatic compounds derived from guaiacyl lignin and/or p-hydroxyphenyl lignin to the transformed microorganism (2), thereby obtaining muconic acid.

Another aspect of the production method according to the present invention (hereinafter referred to as production method (3)) is a method of producing protocatechuic acid, including at least applying aromatic compounds derived from guaiacyl lignin and/or p-hydroxyphenyl lignin, and an aromatic compound derived from syringyl lignin to the transformed microorganism (3), thereby obtaining protocatechuic acid.

As used herein, when referring to the production methods (1) to (3) collectively, they are simply referred to as "production method".

The means of applying aromatic compounds derived from lignin to the transformed microorganism is not particularly limited so long as the means can bring aromatic compounds derived from lignin into contact with the transformed microorganism to obtain muconic acid or protocatechuic acid by the enzymes contained in the transformed microorganism. Examples of the means include the means of culturing the transformed microorganism in a medium containing aromatic compounds derived from lignin and suitable for the growth of the transformed microorganism under a culture condition suitable for the growth of the transformed microorganism to produce muconic acid or protocatechuic acid. The culture technique is not particularly limited, but includes, for example, the solid or liquid culture technique performed under an aerated condition.

The order of the aromatic compound derived from guaiacyl lignin, the aromatic compound derived from p-hydroxyphenyl lignin, and the aromatic compound derived from syringyl lignin applied to the transformed microorganism is not particularly limited. The preferred order is to bring the aromatic compound derived from syringyl lignin into contact with the transformed microorganism followed by bringing the aromatic compound derived from guaiacyl lignin and/or the aromatic compound derived from p-hydroxyphenyl lignin into contact with the transformed microorganism, or to simultaneously bring the aromatic compound derived from syringyl lignin, and the aromatic compound derived from guaiacyl lignin and/or the aromatic compound derived from p-hydroxyphenyl lignin into contact with the transformed microorganism.

The medium may be any standard medium composed of for culturing the host microorganism, and may be either a synthetic or natural medium that contains a carbon source, a nitrogen source, inorganic materials, and other nutrients at an appropriate ratio. Since the host microorganism is a microorganism of the genus *Pseudomonas*, examples of the mediums include, are not particularly limited to, Wx minimal medium and MM medium as described in Examples below. The carbon source may be any one of aromatic compounds derived from lignin and other carbon sources such as sugars and organic acids, or a combination of these. In addition, medium components necessary for the activation of enzymes involved in the production of muconic acid or protocatechuic acid, e.g., $Fe^{2+}$, may be preferably used. While the medium may contain chemical substances such as iron ion and magnesium ion added, the medium may contain them added in the form of mineral-containing material.

The aromatic compounds derived from lignin are not particularly limited, so long as the aromatic compounds are derived from syringyl lignin, guaiacyl lignin and p-hydroxyphenyl lignin, as well as aromatic compounds that are derivable from lignin. Examples of the aromatic compounds include substances corresponding to the degradants of syringyl lignin, p-hydroxyphenyl lignin, and guaiacyl lignin. Specific examples of the aromatic compounds include syringic acid, syringaldehyde, p-coumaric acid, ferulic acid, p-hydroxybenzoic acid, vanillic acid, protocatechuic acid, vanillin and p-hydroxybenzaldehyde, and may also be catechol from phenol, benzoic acid and guaiacol. Examples of the aromatic compounds derived from lignin include compounds that are considered to be model compounds for lignin, e.g., guaiacylglycerol-beta-guaiacyl ether. The aromatic compounds derived from lignin are preferably biomass containing lignin and those extracted by pretreating the biomass. The aromatic compounds may also be chemically synthesized and purified regardless of the biomass. The aromatic compounds derived from lignin may be used either individually or in combination of two or more of such aromatic compounds.

The biomass containing lignin (hereinafter also referred to as lignocellulose) is not particularly limited. Examples of the biomass include natural products such as grasses and trees, those obtained by treating the natural products, and agricultural waste. Specific examples of the biomass include woody biomass such as broad leaf trees and coniferous trees. For example, broad leaf trees are known to contain syringyl lignin highly, while the coniferous trees are known to contain a guaiacyl lignin mainly.

Lignocellulose may be in a solid, suspended, or liquid form, for example, due to the presence or absence of pretreatment. For example, lignocellulose may be a suspension obtained by adding milled lignocellulose to a liquid solution.

Lignocellulose may also be a lignin extract. Examples of lignin extract include suspensions obtained by suspending milled lignocellulose in a solvent suitable for extracting lignin to reach a concentration of 0.1% W/V to 50% W/V, preferably 1% W/V to 20% W/V. The lignin extract may also be a liquid lignin extract obtained by subjecting the suspension to extraction treatment at 10° C. to 150° C., preferably 20° C. to 130° C., more preferably 20° C. to 80° C., for several hours to several days, preferably 1 hour to 6 days, and then removing solid substances from the extracted solution, or a solid lignin extract obtained by evaporating the solvent from the liquid lignin extract and getting dried.

The method of producing the lignin extract is not particularly limited, but includes, for example, the following methods: To a stainless steel vessel of a small autoclave device (Portable Reactor TVS-1, manufactured by Taiatsu Co., Ltd.), 50 ml of 2 M NaOH, 1.5 g of defatted cedar wood powder, and 3 ml of nitrobenzene are added and treated at 170° C. for 2.5 hours while stirring at 500 rpm. The resultant is left until cool to 60° C. or less, and is subjected to centrifugation (6,000 g, 10 min) to collect the supernatant. The supernatant obtained is subjected to diethyl ether extraction and the aqueous layer is collected. This procedure is repeated three times. The aqueous layer is acidified with hydrochloric acid followed by being subjected to diethyl ether extraction and collecting the ether layer. This procedure is repeated three times. Sodium sulfate is added to the ether layer, and the resultant is dehydrated overnight in a refrigerator. The ether layer is collected, and the extract is dried under reduced pressure to obtain a dried solid. The ether extract is dissolved in ion-exchanged water while adding sodium hydroxide (pH≈9), thereby obtaining a solution of aromatic compounds derived from cedar lignin. By using defatted birch wood powder instead of defatted cedar wood powder, a solution of aromatic compounds derived from birch lignin can be obtained.

Solvents suitable for extraction and treatment of lignin are not particularly limited. Examples of such solvents include water, dioxane, low-molecular-weight alcohols such as methanol and isopropanol, diethyl ether, and dimethylformamide.

The culture condition of the transformed microorganism may be any culture condition of *Pseudomonas* microorganism commonly known to those skilled in the art. For example, the initial pH of the medium may be properly conditioned in the range between 5 and 10; the culture temperature may be properly conditioned in the range between 20° C. and 40° C.; and the culture time may be properly conditioned in the range between several hours and several days, preferably 1 day and 7 days, and more preferably 2 days and 5 days. The culture means is not particularly limited. Examples of the culture means include an aerated and agitated deep culture, a shake culture and a static culture. The culture is carried out, preferably provided that the amount of dissolved oxygen is sufficiently present by aeration or other techniques, more preferably provided that the amount of dissolved oxygen is 0.1% to 15%, still more preferably provided that the amount of dissolved oxygen is 1% to 13%, still even more preferably provided that the amount of dissolved oxygen is 2% to 10%. The culture means may be a fed-batch culture carried out by feeding carbon sources depending on the culture states such as the decrease in carbon source and the increase in muconic acid or protocatechuic acid.

One example of the medium and the culture condition may be a shake culture or an agitated culture for 1 day to 5 days at 30° C. and 180 rpm, using Wx minimal medium containing syringic acid, syringaldehyde, and/or an aqueous solution of aromatic compounds derived from birch lignin as carbon sources, as described in Examples below. One example of the medium and the culture condition may be a shake culture or an agitated culture for 1 day to 5 days at 30° C. and 180 rpm and a dissolved oxygen concentration of 5% to 10%, using MM medium containing vanillic acid, p-hydroxybenzoic acid, and/or an aqueous solution of aromatic compounds derived from cedar lignin as carbon sources, as described in Examples below. The carbon source and other components may be properly added after the start of culture.

The method of extracting muconic acid or protocatechuic acid from the culture broth after completion of the culture is not particularly limited. Since muconic acid or protocatechuic acid accumulates in the culture broth, muconic acid or protocatechuic acid is extracted by separating the supernatant from the microorganisms by subjecting the culture broth to known solid-liquid separation treatments such as filtration and centrifugation; and then subjecting the resulting supernatant to extraction treatment such as solid-phase extraction using a column, and solvent extraction using a solvent in which muconic acid or protocatechuic acid is soluble.

The solvent used for extraction is not particularly limited, so long as the solvent can dissolve muconic acid or protocatechuic acid. Examples of the solvent include organic solvents, such as methanol, ethanol, isopropanol, and acetone; and water-containing organic solvents composed of these organic solvents and water mixed together. The extraction temperature is not particularly limited, while examples of the extraction temperature include from room temperature to 100° C.

One specific embodiment of method of extracting muconic acid includes the method according to Vardon et al. (Green chemistry, vol. 18, pp.3397-3413, 2016, incorporated herein by reference in their entirety) and the method partially modified in the above method. Specifically, activated charcoal (12.5% (w/v), 100 mesh) is added to the culture supernatant, and the resultant is stirred for 1 hour. The activated charcoal is removed by suction filtration and the filtrate is collected. Hydrochloric acid is added to the collected filtrate, and the resultant is adjusted to pH≈2 followed by being left overnight at 4° C. The resulting precipitate is collected by suction filtration, washed with ion-exchange water, collected by suction filtration, and then dried under reduced pressure. The dried solid is suspended in ethanol, and the resultant is subjected to suction filtration to remove the ethanol-insoluble unwanted material and to collect the filtrate. The filtrate is dried under reduced pressure in an evaporator to obtain purified muconic acid.

One embodiment of method of extracting protocatechuic acid includes, for example, a method in which hydrochloric acid is added to the culture supernatant such that pH reaches ≈2, and then protocatechuic acid can be extracted using any organic solvents such as ethyl acetate. Protocatechuic acid may be obtained by subjecting the resulting extract to recrystallization or ion-exchange resin treatment.

While qualitative or quantitative analysis of muconic acid or protocatechuic acid is not particularly limited, the analysis may be, for example, performed by HPLC. Those skilled in the art can be able to properly select any HPLC separation conditions, for example, the analysis may be performed using the conditions described in Examples below.

The transformed microorganism can be used to obtain muconic acid or protocatechuic acid with a high yield. For example, by using the transformed microorganism (1), muconic acid can be obtained with a yield of 15 wt % or more during the culture period of 48 hours when the mixture of 5 mM vanillic acid and 10 mM syringic acid is used as a carbon source; muconic acid can be obtained with a yield of 20 wt % or more during the culture period of 24 hours when the mixture of 5 mM p-hydroxybenzoic acid and 10 mM syringic acid is used as a carbon source; and muconic acid can be obtained with a yield of 20 wt % or more during the culture period of 24 hours when the mixture of 5 mM vanillic acid, 5 mM p-hydroxybenzoic acid and 10 mM syringic acid is used as a carbon source. The upper limit of yield is not particularly limited but is typically a yield calculated from the theoretical yield of muconic acid relative to the amount of total carbon sources consumed [the theoretical yield of muconic acid obtained from the consumed phenolic compounds derived from guaiacyl lignin (e.g., vanillic acid) and p-hydroxyphenyl lignin (e.g., p-hydroxybenzoic acid)]. If the transformed microorganism (1) is used, about 100 mg/L to 1,000 mg/L muconic acid can be obtained during the culture period of 60 hours when an aqueous solution of aromatic compounds derived from birch lignin is used as a carbon source.

For example, by using the transformed microorganism (2), muconic acid can be obtained with a yield of 3 wt % or more during the culture period of 24 hours when 25 mM vanillic acid is used as a carbon source; muconic acid can be obtained with a yield of 3 wt % or more during the culture period of 24 hours when 25 mM p-hydroxybenzoic acid is used as a carbon source; and muconic acid can be obtained with a yield of 10 wt % or more during the culture period of 30 hours when the mixture of 25 mM vanillic acid and 25 mM p-hydroxybenzoic acid is used as a carbon source. The upper limit of yield is not particularly limited but is typically a yield calculated from the theoretical yield of muconic acid relative to the amount of total carbon sources consumed [the theoretical yield of muconic acid obtained from the consumed phenolic compounds derived from guaiacyl lignin (e.g., vanillic acid) and p-hydroxyphenyl lignin (e.g., p-hydroxybenzoic acid)]. If the transformed microorganism (2) is used, about 5 mg/L to 1,000 mg/L muconic acid can be obtained during the culture period of 48 hours when an aqueous solution of aromatic compounds derived from cedar lignin is used as a carbon source.

For example, by using the transformed microorganism (3), protocatechuic acid can be obtained with a yield of 5 wt % or more during the culture period of 24 hours when the mixture of 5 mM vanillic acid and 10 mM syringic acid is used as a carbon source; protocatechuic acid can be obtained with a yield of 15 wt % or more during the culture period of 12 hours when the mixture of 5 mM p-hydroxybenzoic acid and 10 mM syringic acid are used as a carbon source; and protocatechuic acid can be obtained with a yield of 15 wt % or more during the culture period of 24 hours when the mixture of 5 mM vanillic acid, 5 mM p-hydroxybenzoic acid and 10 mM syringic acid is used as a carbon source. The upper limit of yield is not particularly limited but is typically a yield calculated from the theoretical yield of protocatechuic acid relative to the amount of total carbon sources consumed [the theoretical yield of protocatechuic acid obtained from the consumed phenolic compounds derived from guaiacyl lignin (e.g., vanillic acid) and p-hydroxyphenyl lignin (e.g., p-hydroxybenzoic acid)].

The production method according to one embodiment of the present invention may include various steps and manipulations before, after, or during the above steps so long as it can achieve the objectives of the present invention.

(Applications of Muconic Acid and Protocatechuic Acid)

Muconic acid and protocatechuic acid obtained by using the transformed microorganism and production method according to one embodiment of the present invention can be converted into various industrially useful compounds. Muconic acid can be used, for example, as raw materials of muconic acid derivatives expected to be used as surfactants, flame retardants, UV light stabilizers, thermosetting plastics, and coating agents. Specifically, adipic acid, one of the muconic acid derivatives, is currently used as a synthetic raw material of nylon 66 (one of polyamides).

Protocatechuic acid is a precursor of muconic acid and also a precursor of protocatechuate 2,3-, 3,4-, and 4,5-ring cleavage metabolites. Some of the metabolites have applications as raw materials for synthetic resins, such as 2-pyrone 4,6-dicarboxylic acid (e.g., Japan Patent No. 4658244). Protocatechuic acid is also used as a synthetic raw material for pharmaceuticals, agrochemicals, and fragrances.

The present invention will now be described in further detail with reference to the following Examples, which are not intended to limit the present invention. The present invention may take various forms to the extent that the objectives of the present invention are achieved.

EXAMPLES

[1. Isolation of *Pseudomonas* sp. NGC7 Strain]

Soils were sampled at 40 sites in Japan, including Hokkaido, Iwate, Niigata, Tochigi, Gunma, Nagano, Aichi, and Shizuoka prefectures. Soil sampling was carried out by collecting a portion of soil near the root of broad leaf trees containing syringyl lignin, that was dug up about 5 cm to 10 cm from the surface. Soil sampling was conducted between May and September 2017 under temperatures in the range between 15° C. and 30° C.

Each soil sample (100 g) was added to 10 mL of Wx liquid medium ($KH_2PO_4$ 1.7 g/L, $Na_2HPO_4 \cdot 12H_2O$ 9.8 g/L, $(NH_4)_2SO_4$ 1 g/L, $MgSO_4 \cdot 7H_2O$ 0.1 g/L, $FeSO_4 \cdot 7H_2O$ 9.5 mg/L, MgO 10.75 mg/L, $CaCO_3$ 2 mg/L, $ZnSO_4 \cdot 7H_2O$ 1.44 mg/L, $MnSO_4 \cdot 4H_2O$ 1.12 mg/L, $CuSO_4 \cdot 5H_2O$ 0.25 mg/L, $CoSO_4 \cdot 7H_2O$ 0.28 mg/L, $H_3BO_3$ 0.06 mg/L and 12N HCl 51.3 µL/L) containing 5 mM syringic acid, and the resultant was subjected to shake culture at 30° C. Twenty-four hours after the start of culture, 100 µL of the culture broth was inoculated into 10 mL of Wx liquid medium containing 5 mM syringic acid, and the resultant was subjected to shake culture at 30° C. for 24 hours. After repeating this procedure four times, the resulting culture broth was streaked onto Wx agar medium containing 5 mM syringic acid as a sole carbon source, and the agar plate was incubated statically. The colonies formed were isolated, and strains that were sensitive to tetracycline and kanamycin were selected. The selected strains were then cultured in Wx liquid medium containing 10 mM syringic acid as a sole carbon source. Among them, nine strains showed excellent growth and selected.

According to known methods, birch wood powder was subjected to alcohol-benzene extraction treatment, and then 1.5 g of the treated birch wood powder was subjected to alkaline nitrobenzene oxidative decomposition treatment and diethyl ether extraction treatment (see "MOKUSHITSU KAGAKU JIKKEN MANUAL", edited by the Japan Wood Research Society, Buneido Co., Ltd., which is incorporated herein by reference in their entirety). The alkaline solution after nitrobenzene oxidative decomposition was subjected to diethyl ether extraction, and the resulting aqueous layer was subjected to acidification treatment and further diethyl ether extraction. The diethyl ether extract obtained as the ether layer was used as aromatic compounds derived from birch lignin, and the aromatic compounds derived from birch lignin were dissolved in water to obtain an aqueous solution of aromatic compounds derived from birch lignin (pH≈9). Nine strains of the above selected microorganisms were cultured at 30° C. for 50 hours in Wx liquid medium containing the aqueous solution of aromatic compounds derived from birch lignin in 5 vol %.

Of the nine strains cultured, four strains were found to grow using an aromatic compound derived from birch lignin as a carbon source by monitoring the absorbance (600 nm) during the cultures. The four strains obtained were named NGC5, NGC6, NGC7, and NGC8 strains, respectively. NGC5, NGC6 NGC7, and NGC8 strains were found to grow by assimilating aromatic compounds derived from p-hydroxyphenyl lignin and guaiacyl lignin.

Among them, NGC7 strain showed to have the best growing ability up to 30 hours after incubation. The nucleotide sequence of 16S rRNA gene of NGC7 strain was determined, and homology searches with the nucleotide sequence were conducted used BLAST program of NCBI (http://www.ncbi.nlm.nih.gov/), Sequence Match program of RDP (https://rdp.cme.msu.edu/), and Clustal Omega and EMBOSS programs of EMBL-EBI (http://ebi.ac.uk/). As a result, the nucleotide sequence of 16S rRNA gene of NGC7 strain had 99.5%, 99.4%, 99.2%, 99.0%, and 96.1% sequence identity to the nucleotide sequence of 16S rRNA gene of *P. putida* NBRC14164, *P. plecoglossicida* ATCC700383, *P. taiwanensis* DSM21245, *P. monteilii* ATCC700476, and *P. fulva* NBRC16637, respectively. Thus, according to the nucleotide sequence analysis targeting 16S rRNA gene, NGC7 strain was classified as *Pseudomonas* sp. NGC7 strain. With respect to NGC5, NGC6, and NGC8 strains, the nucleotide sequence of 16S rRNA gene was also determined. As a result, as with the nucleotide sequence of NGC7 strain, the nucleotide sequences of NGC5 and 6 strains had 99% or more sequence identity to those of the several standard strains. Thus, NGC 5 and NGC 6 strains were classified as *Pseudomonas* sp. NGC5 and NGC6 strains, respectively. Since the nucleotide sequence of NGC8 strain had 99.9% sequence identity to that of *P. putida* NBRC14164, NGC8 strain was classified as *P. putida* NGC8.

Each growing ability of NGC 7 as well as NGC 5, NGC6, and NGC8 was evaluated in Wx liquid medium with syringic acid, syringaldehyde, vanillic acid, vanillin, ferulic acid, 4-hydroxybenzoic acid, 4-hydroxybenzaldehyde, or protocatechuic acid as a sole carbon source. As a result, NGC 7 as well as NGC 5, NGC6, and NGC8 vigorously grew with all carbon sources. [2a. Preparation of *Pseudomonas* sp. NGC7ApcaHGAcatB Strain]

*Pseudomonas* sp. NGC7ApcaHGAcatB strain, which is a mutated strain of *Pseudomonas* sp. NGC7 with disruptions of protocatechuate 3,4-dioxygenase gene (pcaHG gene) and cis, cis-muconic acid cycloisomerase gene (catB gene), was prepared from NGC7 strain by the following procedure. *Pseudomonas* sp. NGC7 strain has been deposited internationally under the following conditions.

(1) Name of depositary: NITE Patent Microorganisms Depositary (NPMD), National Institute of Technology and Evaluation, (2) Address: #122, 2-5-8 KazusaKamatari, Kisarazu-shi, Chiba 292-0818, Japan
(3) Accession number: NITE BP-03043
(4) Identification reference: NGC7
(5) Date of original deposit: Oct. 4, 2019
(6) Proposed taxonomic designation: *Pseudomonas* sp.
(7) Scientific description:

Rod-shaped bacterium, gram-negative, no spore, motile.
Colony morphology on LB agar medium (30° C., 48 hours): 3 mm to 4 mm in diameter, pale yellow, round, lenticular, all edges, smooth, opaque, butter-like.
Catalase and oxidase reactions are positive, and glucose oxidation capacity is present.
Not reducing nitrate, and having arginine dihydrolase activity.
Not having gelatin hydrolysis activity. Assimilating glucose, potassium gluconate, and n-capric acid.
Not assimilating L-arabinose or adipic acid.
Producing fluorescent dye on Kigs'B agar plate.
Growing at 4° C. and in the presence of 6% NaCl, but not at 41° C. and in the presence of 7% NaCl.
Not having lecithinase and lipase activities.
Being assumed to belong *Pseudomonas putida* based on the results of physiological tests.

Using the genomic DNA of *Pseudomonas* sp. NGC7 strain isolated in the item 1 above to serve as a template, PCR with the primer set consisting of primers 1 and 2 indicated in SEQ ID Nos: 1 and was carried out to amplify about 1.2 kbp of DNA fragment containing protocatechuate 3,4-dioxygenase beta subunit (pcaH) gene and protocatechuate 3,4-dioxygenase alpha subunit (pcaG) gene.

The amplified DNA fragment was digested with EcoRI and HindIII, and then ligated with pK19mobsacB digested with EcoRI and HindIII in advance (see Gene, Vol. 145, pp.69-73, 1994, incorporated herein by reference in their entirety) to obtain pPcaHG plasmid DNA. About 6.4 kbp of DNA fragment obtained by digesting pPcaHG plasmid with ApaI and DraIII was subjected to DNA blunting treatment followed by ligation reaction to obtain pPcaHGdel plasmid DNA in which pcaH and pcaG genes were deleted in part.

A transformant was obtained by introducing pPcaHGdel plasmid DNA into *Pseudomonas* sp. NGC7 strain using triparental mating conjugating method. The transformant could grow on LB agar medium containing 50 mg/L kanamycin (Km), and was selected as Km-resistant strain. The selected Km-resistant strain was inoculated into Wx liquid medium containing 5 mM syringic acid and 10% (w/v) sucrose and grown at 30° C. until stationary phase.

Part of the culture broth was inoculated into fresh Wx liquid medium containing 5 mM syringic acid and 10% (w/v) sucrose, and incubated at 30° C. until stationary phase. This procedure was repeated four more times. The resulting culture broth was streaked onto fresh Wx agar plate containing 5 mM syringic acid and 10% (w/v) sucrose, and the plate was statically incubated at 30° C. The transformant in which the partial deletion of pcaH and pcaG genes on the genomic DNA was confirmed by colony direct PCR was designated as protocatechuate 3,4-dioxygenase gene-disrupted strain (NGC7ΔpcaHG strain).

Using the genomic DNA of *Pseudomonas* sp. NGC7 strain to serve as a template, PCR with the primer set consisting of primers 3 and 4 indicated in SEQ ID NOs: 3 and 4 was carried out to amplify about 2.2 kbp of DNA fragment containing cis, cis-muconate cycloisomerase (catB) gene, muconolactone delta-isomerase (catC) gene, and catechol 1,2-dioxygenase (catA) gene.

The amplified DNA fragment was digested with EcoRI and HindIII, and then ligated with pK19mobsacB digested with EcoRI and HindIII in advance to obtain pCatBCA plasmid DNA. About 7.7 kbp of DNA fragment obtained by digesting pCatBCA plasmid with EcoRV and ScaI was circularized by carrying out ligation reaction to obtain pCatBCAdel plasmid DNA in which part of catB gene was deleted.

A transformant was obtained by introducing pCatBCAdel plasmid DNA into *Pseudomonas* sp. NGC7ΔpcaHG strain using triparental mating conjugating method. The transformant could grow on LB agar medium containing 50 mg/L Km, and was selected as Km-resistant strain. The selected Km-resistant strain was inoculated into Wx liquid medium containing 5 mM syringic acid and 10% (w/v) sucrose, and grown at 30° C. until stationary phase.

Part of the culture broth was inoculated into fresh Wx liquid medium containing 5 mM syringic acid and 10% (w/v) sucrose, and incubated at 30° C. until stationary phase. This procedure was repeated four more times. The resulting culture broth was streaked onto fresh Wx agar plate containing 5 mM syringic acid and 10% (w/v) sucrose, and the plate was incubated at 30° C. by leaving to stand. The transformant in which the partial deletion of catB gene on the genomic DNA was confirmed by colony direct PCR was designated as *Pseudomonas* sp. NGC7ΔpcaHGΔcatB strain in which both protocatechuate 3,4-dioxygenase gene and cis, cis-muconate cycloisomerase were disrupted.

[2b. Preparation of NGC7ΔpcaHGΔcatB/pTS110 strain]

The following procedures were conducted to prepare NGC7ΔpcaHGΔcatB/pTS110 strain by transforming *Pseudomonas* sp. NGC7ΔpcaHGΔcatB strain with pTS110 plasmid DNA that can express pcaH gene, pcaG gene and aroY gene.

Using pUC118 plasmid DNA (Gene, vol. 28, p351-359) to serve as a template, PCR with the primer set consisting of primers 5 and 6 indicated in SEQ ID NOs: 5 and 6 was carried out to amplify about 200 bp of DNA fragment containing lactose promoter region (Plac). The obtained DNA fragment was cloned into pJB866 plasmid DNA at NotI site by using In-Fusion HD Cloning Kit (Takara Bio) to obtain pTS093 plasmid DNA.

Using the genomic DNA of *Pseudomonas putida* KT2440 strain (*P. putida* NBRC100650 strain, purchased from National Institute of Technology and Evaluation, Biological Resource Center (NBRC)) to serve as a template, PCR with the primer set consisting of primers 7 and 8 indicated in SEQ ID NOs: 7 and 8 was carried out to amplify about 1.3 kbp of DNA fragment containing pcaG gene and pcaH gene. The amplified DNA fragment was digested with SacI and BamHI, and then cloned into pUC118 plasmid DNA digested with SacI and BamHI in advance, thereby obtaining pTS107 plasmid DNA.

DNA fragment (about 1.3 kbp) containing pcaG gene and pcaH gene, which was obtained by digesting pTS107 plasmid DNA with SacI and BamHI, was ligated with pTS093 plasmid DNA at SacI-BamHI site to obtain pTS108 plasmid DNA.

Using partial fragment of the genomic DNA of *Klebsiella pneumoniae* subsp. *pneumoniae* A170-40 strain (pKD136; ATCC69875, purchased from American Type Culture Collection (ATCC)) to serve as a template, PCR with the primer set consisting of primers 9 and 10 indicated in SEQ ID NOs: 9 and 10 was carried out to amplify about 1.5 kbp of DNA fragment containing protocatechuate decarboxylase (aroY) gene. The amplified DNA fragment was digested with KpnI, and then cloned to pMCL200 plasmid DNA digested with KpnI in advance to obtain pTS036 plasmid DNA.

Using pTS036 plasmid DNA to serve as a template, PCR with the primer set consisting of primers 11 and 12 indicated in SEQ ID NOs: 11 and 12 was carried out to amplify about 1.5 kbp of DNA fragment containing aroY gene. The obtained DNA fragment was cloned into pTS093 plasmid DNA at NotI site by using In-Fusion HD Cloning Kit to obtain pTS109 plasmid DNA. DNA fragment (about 1.3 kbp) obtained by digesting pTS107 plasmid DNA with SacI and HindIII was ligated with pTS109 plasmid DNA at SacI-HindIII site to obtain pTS110 plasmid DNA.

The obtained pTS110 plasmid DNA was used to transform *Pseudomonas* sp. NGC7ΔpcaHGΔcatB strain to prepare NGC7ΔpcaHGΔcatB/pTS110 strain.

[2c. Preparation of NGC7ΔpcaHGΔcatB/pTS119 Strain]

The following procedures were conducted to prepare NGC7ΔpcaHGΔcatB/pTS119 strain by transforming NGC7ΔpcaHGΔcatB strain with pTS119 plasmid DNA that can express pcaH gene, pcaG gene, aroY gene, catA gene, vanA gene, and vanB gene.

Using the genomic DNA of *Pseudomonas putida* KT2440 strain to serve as a template, PCR with the primer set consisting of primers 13 and 14 indicated in SEQ ID NOs: 13 and 14 was carried out to amplify about 1 kbp of DNA fragment containing catechol 1,2-dioxygenase (catA) gene. The amplified DNA fragment was digested with KpnI and SmaI, and then cloned into pUC118 plasmid DNA digested with KpnI and SmaI in advance to obtain pNI001 plasmid DNA.

Using pNI001 plasmid DNA to serve as a template, PCR with the primer set consisting of primers 15 and 16 indicated in SEQ ID NOs: 15 and 16 was carried out to amplify about 1 kbp of DNA fragment containing catA gene. The obtained DNA fragment was ligated with pTS109 plasmid DNA digested with NotI in advance by using In-Fusion HD Cloning Kit to obtain pTS115 plasmid DNA.

Using the genomic DNA of *P. putida* KT2440 strain to serve as a template, PCR with the primer set consisting of primers 17 and 18 indicated in SEQ ID NOs: 17 and 18 was carried out to amplify about 2.0 kbp of DNA fragment containing vanillate O-demethylase oxygenase component (vanA) gene and vanillate O-demethylase oxidoreductase component (vanB) gene. The amplified DNA fragment was digested with SacI and SmaI, and then ligated with pQE30 plasmid DNA digested with SacI and SmaI in advance to obtain pKY001 plasmid DNA.

Using pKY001 plasmid DNA to serve as a template, PCR with the primer set consisting of primers 19 and 20 indicated in SEQ ID NOs: 19 and 20 was carried out to amplify about 2.0 kbp of DNA fragment containing vanA gene and vanB gene. The obtained DNA fragment was ligated with pTS115 plasmid DNA digested with NotI in advance by using In-Fusion HD Cloning Kit to obtain pTS116 plasmid DNA.

Using pTS107 plasmid DNA to serve as a template, PCR with the primer set consisting of primers 21 and 22 indicated in SEQ ID Nos. 21 and 22 was carried out to amplify about 1.3 kbp of DNA fragment containing pcaG gene and pcaH gene. The obtained DNA fragment was ligated with pTS116 plasmid DNA digested with HindIII in advance by using In-Fusion HD Cloning Kit to obtain pTS119 plasmid DNA.

The obtained pTS119 plasmid DNA was used to transform NGC7ApcaHGAcatB strain to prepare NGC7ApcaHGAcatB/pTS119 strain.

[2d. Preparation of NGC7ΔpcaHGΔcatB/pTS084 Strain]

Using the genomic DNA of *Klebsiella pneumoniae* subsp. *pneumoniae* NBRC14190 strain (NBRC14190G, purchased from NBRC) to serve as a template, PCR with the primer set consisting of primers 23 and 24 indicated in SEQ ID NOs: 23 and 24 was carried out to amplify about 0.6 kbp of DNA fragment containing 4-hydroxybenzoate decarboxylase subunit B (kpdB) gene. The amplified DNA fragment was subjected to DNA blunting treatment at both ends, digested with XbaI, and then ligated with pTS036 plasmid DNA subjected to DNA blunting treatment in advance to obtain pTS052 plasmid DNA. pTS052 plasmid DNA was selected and obtained as a clone in which kpdB gene was ligated in the forward direction into aroY gene in pTS036 plasmid DNA.

Using pTS052 plasmid DNA to serve as a template, PCR with the primer set consisting of primers 25 and 26 indicated in SEQ ID NOs: 25 and 26 was carried out to amplify about 2.2 kbp of DNA fragment containing aroY gene and kpdB gene. The amplified DNA fragment was ligated with pJB866 plasmid DNA (Plasmid, vol. 38, pp. 35-51, 1997) digested with BamHI and EcoRI in advance by using In-Fusion HD Cloning Kit to obtain pTS074 plasmid DNA.

Using the genomic DNA of *Pseudomonas putida* KT2440 strain to serve as a template, PCR with the primer set consisting of primers 27 and 28 indicated in SEQ ID NOs: 27 and 28 was carried out to amplify about 1.0 kbp of DNA fragment containing catechol 1,2-dioxygenase (catA) gene. The obtained DNA fragment was ligated with pTS074 plasmid DNA digested with SacI in advance by using In-Fusion HD Cloning Kit to obtain pTS079 plasmid DNA.

Using pUC118 plasmid DNA to serve as a template, PCR with the primer set consisting of primers 29 and 30 indicated in SEQ ID NOs: 29 and 30 was carried out to amplify about 200 bp of DNA fragment containing lactose promoter region (Plac). The obtained DNA fragment was cloned into pTS079 plasmid DNA at NotI site by using In-Fusion HD Cloning Kit to obtain pTS082 plasmid DNA.

Using pKY001 plasmid DNA to serve as a template, PCR with the primer set consisting of primers 31 and 32 indicated in SEQ ID NOs: 31 and 32 was carried out to amplify about 2.0 kbp of DNA fragment containing vanA gene and vanB gene. The amplified DNA fragment was ligated with pTS082 plasmid DNA digested with NotI in advance by using In-Fusion HD Cloning Kit to obtain pTS084 plasmid DNA.

The obtained pTS084 plasmid DNA was used to transform *Pseudomonas* sp. NGC7ApcaHGAcatB strain to prepare NGC7ΔpcaHGΔcatB/pTS084 strain.

[3. Production of cis, cis-muconic Acid (ccMA) using Vanillic Acid (VA) as a Carbon Source]

NGC7ApcaHGAcatB/pTS110 strain was inoculated into 5 mL of LB liquid medium containing 15 mg/L tetracycline (Tc), and shake-cultured at 30° C. for 16 hours. The resulting culture was washed with MM medium containing no carbon source ($Na_2HPO_4$ 13.56 g/L, $KH_2PO_4$ 6 g/L, NaCl 1 g/L, $NH_4Cl2$ g/L, 2 mM $MgSO_4$, 100 μM $CaCl_2$, and 18 μM $FeSO_4$), and then inoculated into 5 mL of MM liquid medium containing 15 mg/L Tc and 25 mM VA. The inoculated medium was subjected to shake culture at 30° C.

The optical density (OD) of the culture broth was measured at regular intervals after the start of culture, and the concentrations of VA and ccMA in the culture supernatant obtained by centrifugation of the culture broth were measured.

A wavelength of 600 nm was used for OD measurement, and OD600 value was measured using "miniphoto 518R" (Taitec Corporation).

The concentrations of VA and ccMA were measured using a high-performance liquid chromatograph ("Agilent 1200 series"; Agilent Technologies). The column used was "ZOR- BAX Eclipse Plus C18 column" (diameter: 4.6 mm, length: 150 mm, particle size: 0.5 μm), and the temperature was maintained at 40° C. The gradient elution mode (Solvent A: 5% (v/v) CH₃OH, 1% (v/v) CH₃COOH, Solvent B: 50% (v/v) CH₃OH, 1% (v/v) CH₃COOH) was used. After equilibrating with Solvent A, the percentage of Solvent B was increased to 20% over 8 minutes from the start of analysis, and then increased to 100% over 5 minutes. The flow rate of the mobile phase was set at 1.0 mL/min, and the measurement wavelength was set at 280 nm.

Table 1 summarizes the measurement results of OD600 value, VA concentration, and ccMA concentration for NGC7ΔpcaHGΔcatB/pTS110 strain at 0 hour and 24 hours after the start of culture.

TABLE 1

| Culture time (h) | 0 | 24 |
|---|---|---|
| OD600 | 0.25 | 1.40 |
| VA (g/L) | 3.7 | 0 |
| ccMA (mg/L) | 0 | 190 |

As shown in Table 1, NGC7ΔpcaHGΔcatB/pTS110 strain grew by assimilating VA and produced ccMA (the yield was 5.1 wt %). In addition, the yield was determined by the amount of ccMA relative to the amount of substrate (VA) consumed.

[4. ccMA Production using p-hydroxybenzoic Acid (HBA) as a Carbon Source]

NGC7ΔpcaHGΔcatB/pTS110 strain was inoculated into 5 mL of LB liquid medium containing 15 mg/L Tc, and shake-cultured at 30° C. for 16 hours. The obtained culture was washed with MM medium without containing any carbon sources, and then inoculated into 5 mL of MM liquid medium containing 15 mg/L Tc and 25 mM HBA. The inoculated medium was subjected to shake culture at 30° C.

At regular intervals after the start of culture, the optical density (OD) of the culture broth as well as the concentrations of HBA and ccMA in the culture broth were measured. The OD600 value and the concentrations of HBA and ccMA were measured in the same way as described in the item 3 above.

Table 2 summarizes the measurement results of OD600 value, HBA concentration, and ccMA concentration for NGC7ΔpcaHGΔcatB/pTS110 strain at 0 hour and 24 hours after the start of culture.

TABLE 2

| Culture time (h) | 0 | 24 |
|---|---|---|
| OD600 | 0.17 | 1.2 |
| HBA (g/L) | 3.3 | 0 |
| ccMA (mg/L) | 0 | 207 |

As shown in Table 2, NGC7ΔpcaHGΔcatB/pTS110 strain grew by assimilating HBA and produced ccMA (the yield was 6.3 wt %). In addition, the yield was determined by the amount of ccMA relative to the amount of substrate (HBA) consumed.

[5. ccMA Production Using a Mixture of VA and HBA as a Carbon Source]

NGC7ΔpcaHGΔcatB/pTS110 strain was inoculated into 5 mL of LB liquid medium containing 15 mg/L Tc, and shake-cultured at 30° C. for 16 hours. The obtained culture was washed with MM medium without containing any carbon sources, and then inoculated into 5 mL of MM liquid medium containing 15 mg/L Tc, 25 mM VA and 25 mM HBA. The inoculated medium was subjected to shake culture at 30° C.

At regular intervals after the start of culture, the optical density (OD) of the culture broth as well as the concentrations of VA, HBA, and ccMA in the culture broth were measured. The OD600 value and the concentrations of VA, HBA, and ccMA were measured in the same way as described in the item 3 above.

Table 3 summarizes the measurement results of OD600 value, VA concentration, HBA concentration, and ccMA concentration at 0 hour, 24 hours, and 30 hours after the start of culture.

TABLE 3

| Culture time (h) | 0 | 24 | 30 |
|---|---|---|---|
| OD600 | 0.19 | 1.52 | 1.61 |
| VA (g/L) | 3.7 | 0.09 | 0 |
| HBA (g/L) | 2.9 | 0 | 0 |
| ccMA (mg/L) | 0 | 1.0 | 1.1 |

As shown in Table 3, NGC7ΔpcaHGΔcatB/pTS110 strain grew by assimilating VA and HBA, and produced ccMA over time (the yield was 16.7 wt %). In addition, the yield was determined by the amount of ccMA relative to the amounts of substrates (VA and HBA) consumed.

[6. ccMA Production using a Mixture of Vanillin (VN) and 4-hydroxybenzaldehyde (HBN) as a Carbon Source]

NGC7ΔpcaHGΔcatB/pTS110 strain was inoculated into 5 mL of LB liquid medium containing 15 mg/L Tc, and shake-cultured at 30° C. for 16 hours. The obtained culture was washed with MM medium without any carbon sources, and then inoculated into 5 mL of MM liquid medium containing 15 mg/L Tc, 5 mM VN and 5 mM HBN. The inoculated medium was subjected to shake culture at 30° C.

At regular intervals after the start of culture, the optical density (OD) of the culture broth as well as the concentrations of VN, HBN and ccMA in the culture broth were measured. The OD600 value and the concentrations of VN, HBN, and ccMA were measured in the same way as described in the item 3 above.

Table 4 summarizes the measurement results of OD600 value, VN concentration, HBN concentration, and ccMA concentration at 0 hour, 24 hours, 30 hours, and 48 hours after the start of culture.

TABLE 4

| Culture time (h) | 0 | 24 | 30 | 48 |
|---|---|---|---|---|
| OD600 | 0.04 | 0.07 | 0.10 | 0.87 |
| VN (g/L) | 0.75 | 0.61 | 0.49 | 0 |
| HBA (g/L) | 0.62 | 0.49 | 0.35 | 0 |
| ccMA (mg/L) | 0 | 0 | 0 | 22 |

As shown in Table 4, NGC7ΔpcaHGΔcatB/pTS110 strain grew by assimilating VN and HBN, and produced ccMA (the yield was 1.6 wt %). In addition, the yield was determined by the amount of ccMA relative to the amounts of substrates (VN and HBN) consumed.

[7. ccMA Production using a Mixture of VN, HBN, VA and HBA as a Carbon Source]

NGC7ΔpcaHGΔcatB/pTS110 strain was inoculated into 5 mL of LB liquid medium containing 15 mg/L Tc, and shake-cultured at 30° C. for 16 hours. The obtained culture was washed with MM medium without containing any carbon sources, and then inoculated into 5 mL of MM liquid medium containing 15 mg/L Tc, 5 mM VN, 5 mM HBN, 10 mM VA, and 10 mM HBA. The inoculated medium was subjected to shake culture at 30° C.

At regular intervals after the start of culture, the optical density (OD) of the culture broth as well as the concentrations of VN, HBN, VA, HBA, and ccMA in the culture broth were measured. The OD600 value and the concentrations of VN, HBN, VA, HBA, and ccMA were measured in the same way as described in the item 3 above.

Table 5 summarizes the measurement results of OD600 value, VN concentration, HBN concentration, VA concentration, HBA concentration, and ccMA concentration at 0 hour, 24 hours, 30 hours, and 48 hours after the start of culture.

TABLE 5

| Culture time (h) | 0 | 24 | 30 | 48 |
|---|---|---|---|---|
| OD600 | 0.08 | 0.26 | 1.0 | 1.5 |
| VN (g/L) | 0.75 | 0.23 | 0 | 0 |
| HBN (g/L) | 0.61 | 0.07 | 0 | 0 |
| VA (g/L) | 1.7 | 2.0 | 1.8 | 0 |
| HBA (g/L) | 1.4 | 1.8 | 0.40 | 0 |
| ccMA (mg/L) | 0 | 6 | 145 | 283 |

As shown in Table 5, NGC7ΔpcaHGΔcatB/pTS110 strain grew by assimilating VN, HBN, VA, and HBA, and produced ccMA over time (the yield was 6.3 wt %). In addition, the yield was determined by the amount of ccMA relative to the amounts of substrates (VN, HBN, VA and HBA) consumed.

[8. ccMA Production (1) Using Cedar Lignin-Derived Phenols as a Carbon Source]

According to known methods, cedar wood powder was subjected to alcohol-benzene extraction treatment, and then 1.5 g of the treated cedar wood powder was subjected to alkaline nitrobenzene oxidative decomposition treatment and further diethyl ether extraction treatment (see "MOKUSHITSU KAGAKU JIKKEN MANUAL", edited by the Japan Wood Research Society, Buneido Co., Ltd., which is incorporated herein by reference in their entirety). The alkaline solution after nitrobenzene oxidative decomposition was subjected to diethyl ether extraction, and the resulting aqueous layer was subjected to acidification treatment and further diethyl ether extraction. The diethyl ether extract obtained as the ether layer was designated as aromatic compounds (phenols) derived from cedar lignin, and the ccMA productivity was evaluated in MM medium containing an aqueous solution (pH≈9) of the aromatic compounds derived from cedar lignin as a sole carbon source.

NGC7ΔpcaHGΔcatB/pTS110 strain was inoculated into 5 mL of LB liquid medium containing 15 mg/L Tc, and shake-cultured at 30° C. for 16 hours. The obtained culture was washed with MM medium without containing any carbon sources, and then inoculated into 5 mL of MM liquid medium containing 15 mg/L Tc. After adding 0.5 mL of the aqueous solution of phenols derived from cedar lignin as a carbon source, the inoculated medium was subjected to shake culture at 30° C. Twenty-four hours after the start of culture, 0.5 mL of the aqueous solution of aromatic compounds derived from cedar lignin was further added to the culture broth, and the culture broth was shake-cultured at 30° C.

At regular intervals after the start of culture, the optical density (OD) of the culture broth as well as the concentration of ccMA in the culture broth were measured. The OD600 value and the concentration of ccMA were measured in the same way as described in the item 3 above.

Table 6 summarizes the measurement results of OD600 value and ccMA concentration at 0 hour, 24 hours, and 48 hours after the start of culture.

TABLE 6

| Culture time (h) | 0 | 24 | 48 |
|---|---|---|---|
| OD600 | 0.25 | 0.71 | 1.26 |
| ccMA (mg/L) | 0 | 5.0 | 10.0 |

As shown in Table 6, NGC7ΔpcaHGΔcatB/pTS110 strain grew by assimilating an aromatic compound derived from lignin of cedar, an actual biomass, and produced ccMA over time.

[9. ccMA Production (2) Using Cedar Lignin-Derived Phenols as a Carbon Source]

NGC7ΔpcaHGΔcatB/pTS119 strain was inoculated into 5 mL of LB liquid medium containing 15 mg/L Tc, and shake-cultured at 30° C. for 16 hours. A portion (50 μL) of the obtained culture broth was inoculated into 5 mL of MM liquid medium containing 15 mg/L Tc. After adding 0.5 mL of the aqueous solution of cedar lignin-derived phenols as a source, the inoculated medium was shake-cultured at 30° C. Twenty-four hours after the start of culture, 0.5 mL of the aqueous solution of cedar lignin-derived phenols was further added to the culture broth, and the culture broth was shake-cultured at 30° C.

At regular intervals after the start of culture, the optical density (OD) of the culture broth as well as the concentration of ccMA in the culture broth were measured. The OD600 value and the concentration of ccMA were measured in the same way as described in the item 3 above.

Table 7 summarizes the measurement results of OD600 value and ccMA concentration at 0 hour, 24 hours, and 48 hours after the start of culture.

TABLE 7

| Culture time (h) | 0 | 24 | 48 |
|---|---|---|---|
| OD600 | 0.24 | 0.71 | 1.44 |
| ccMA (mg/L) | 0 | 15.0 | 30.0 |

As shown in Table 7, NGC7ΔpcaHGΔcatB/pTS119 strain grew by assimilating an aromatic compound derived from lignin of cedar, an actual biomass, and produced ccMA over time.

[10. ccMA Production (2) using a Mixture of VA and HBA as a Carbon Source]

NGC7ΔpcaHGΔcatB/pTS110 strain was inoculated into 10 mL of LB liquid medium containing 20 mg/L Tc, and shake-cultured at 30° C. overnight. The obtained culture medium (1 mL) was inoculated into 0.1 L of MM liquid medium containing 20 mg/L Tc, 25 mM VA, and 25 mM HBA, and subjected to stirred aerated culture at 30° C., pH 7, for 12 hours to 48 hours while keeping the dissolved oxygen concentration (DO) within a certain range during the culture period. The DO sensor used was calibrated with air-saturated MM medium (DO=100%) and 5% sodium sulfite solution (DO=0%) before the start of culture.

The concentrations of VA, HBA, and ccMA after the culture were measured in the same way as described in item 3 above. Based on the measurement results obtained, the yield of ccMA was determined by the amount of ccMA relative to the amounts of substrates (VA and HBA) consumed. Table 8 summarizes the measurement results of ccMA yield and the DO value kept.

TABLE 8

| DO (%) | 1.0 | 2.5 | 5 | 10 | 15 | 20 |
|---|---|---|---|---|---|---|
| ccMA yield (wt %) | 20.5 | 17.9 | 20.3 | 16.8 | 11.5 | 9.3 |

As shown in Table 8, the yield of ccMA produced was excellent under the conditions where the dissolved oxygen concentration in the culture broth was in the range between 1.0% and 10% (the yield was about 17 wt % or higher).

[11. ccMA Production (1) using a Mixture of SA and VA as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 10 mL of Wx minimal medium containing 12.5 mg/L Tc, 10 mM SA and 5 mM VA. The inoculated medium was subjected to shake culture at 30° C.

The OD600 value of the culture broth was measured at regular intervals after the start of culture, and the concentrations of SA, VA, and ccMA were measured in the culture supernatant obtained by centrifugation of the culture broth.

The OD600 value was measured with "GeneQuant 100" (GE Healthcare Japan).

The concentrations of SA, VA, and ccMA were measured using a high-performance liquid chromatograph ("Acquity ultraperformance liquid chromatography system"; Waters Corporation). The column used was "TSKgel ODS-140HTP column" (diameter: 2.1 mm, length: 100 mm, particle size: 2.3 μm; TOSOH Corporation), and the temperature was maintained at 30° C. The gradient elution mode (Solvent A: 99.9% (v/v) $H_2O$, 0.1% (v/v) HCOOH, Solvent B: 99.9% (v/v) $CH_3CN$, 0.1% (v/v) HCOOH) was used. After equilibrating with a mixture of 99% Solvent A and 1% Solvent B, the percentage of Solvent B was increased to 25% over three minutes to 6 minutes from the start of analysis, and then decreased to 1% over 1 minutes. The flow rate of the mobile phase was set at 0.5 mL/min, and the measurement wavelength was set at 270 nm for SA, and 260 nm for VA and ccMA.

Table 9 summarizes the measurement results of OD600 value, SA concentration, VA concentration, and ccMA concentration at 0 hour, 12 hours, 24 hours, 36 hours, and 48 hours after the start of culture.

TABLE 9

| Culture time (h) | 0 | 12 | 24 | 36 | 48 |
|---|---|---|---|---|---|
| OD600 | 0.24 | 1.14 | 1.67 | 1.60 | 1.42 |
| SA (g/L) | 1.77 | 0.39 | 0 | 0 | 0 |
| VA (g/L) | 0.75 | 0.18 | 0 | 0 | 0 |
| ccMA (g/L) | 0 | 0.20 | 0.56 | 0.54 | 0.55 |

As shown in Table 9, NGC7ΔpcaHGΔcatB/pTS084 strain grew by assimilating SA, and produced ccMA from VA over time (the yield was 21.8 wt %). In addition, the yield was determined by the amount of ccMA relative to the amounts of substrates (SA and VA) consumed.

[12. ccMA Production (2) using a Mixture of SA and VA as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 10 mL of Wx minimal medium containing 12.5 mg/L Tc as well as a mixture of SA and VA at the amounts as indicated in Table 10. The inoculated medium was subjected to shake culture at 30° C. for 48 hours.

TABLE 10

| | Condition 1 | Condition 2 | Condition 3 | Condition 4 | Condition 5 |
|---|---|---|---|---|---|
| SA (g/L) | 1.86 | 2.85 | 3.90 | 4.44 | 5.19 |
| VA (g/L) | 0.77 | 1.15 | 1.57 | 2.00 | 2.43 |

The concentrations of SA, VA, and ccMA were measured in the culture supernatant obtained by centrifugation of the culture broth 48 hours after the start of culture. The results are shown in Table 11. The concentrations of SA, VA, and ccMA were measured in the same way as described in the item 11 above.

TABLE 11

| | Condition 1 | Condition 2 | Condition 3 | Condition 4 | Condition 5 |
|---|---|---|---|---|---|
| ccMA (g/L) | 0.59 | 0.83 | 0.95 | 1.20 | 1.38 |
| Yield (wt %) | 22.4 | 20.8 | 17.4 | 18.6 | 18.1 |

As shown in Table 11, even if SA and VA were set at high concentrations at the start of culture, NGC7ΔpcaHGΔcatB/pTS084 strain grew, and produced ccMA (the yield was 17 wt % or more). In addition, the yield was determined by the amount of ccMA relative to the amounts of substrates (SA and VA) consumed.

[13. ccMA Production (3) using a Mixture of SA and VA as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc as well as a mixture of SA and VA at the amounts as indicated in Table 12 (in this case, a 500 mL baffled flask was used as the culture vessel). The inoculated medium was subjected to rotational culture at 30° C.

TABLE 12

| | Condition 1 | Condition 2 | Condition 3 |
|---|---|---|---|
| SA (g/L) | 1.85 | 3.60 | 5.05 |
| VA (g/L) | 0.85 | 1.50 | 2.18 |

The OD600 value of the culture broth was measured at regular intervals after the start of culture, and the concentrations of SA, VA, and ccMA in the culture supernatant obtained by centrifugation of the culture broth were measured. The OD600 value and the concentrations of SA, VA, and ccMA were measured in the same way as described in the item 11 above.

Table 13 (for Condition 1), Table 14 (for Condition 2), and Table 15 (for Condition 3) summarize the measurement results of OD600 value, SA concentration, VA concentration, and ccMA concentration at 0 hour, 12 hours, 24 hours, 36 hours, and 48 hours after the start of culture.

TABLE 13

| Culture time (h) | 0 | 12 | 24 | 36 | 48 |
|---|---|---|---|---|---|
| OD600 | 0.24 | 1.23 | 1.44 | 1.73 | 1.66 |
| SA (g/L) | 1.85 | 0.51 | 0 | 0 | 0 |
| VA (g/L) | 0.85 | 0.29 | 0 | 0 | 0 |
| ccMA (g/L) | 0 | 0.14 | 0.55 | 0.57 | 0.57 |

TABLE 14

| Culture time (h) | 0 | 12 | 24 | 36 | 48 |
|---|---|---|---|---|---|
| OD600 | 0.23 | 0.69 | 2.24 | 2.50 | 2.14 |
| SA (g/L) | 3.60 | 2.95 | 0.10 | 0 | 0 |
| VA (g/L) | 1.50 | 1.29 | 0.04 | 0 | 0 |
| ccMA (g/L) | 0 | 0.06 | 0.67 | 0.88 | 0.94 |

TABLE 15

| Culture time (h) | 0 | 12 | 24 | 36 | 48 |
|---|---|---|---|---|---|
| OD600 | 0.24 | 0.49 | 1.50 | 2.71 | 2.68 |
| SA (g/L) | 5.05 | 4.57 | 2.50 | 0.03 | 0 |
| VA (g/L) | 2.18 | 2.02 | 1.34 | 0.02 | 0 |
| ccMA (g/L) | 0 | 0.04 | 0.32 | 1.02 | 1.25 |

As shown in Tables 13 to 15, even if SA and VA were set at high concentrations at the start of culture, NGC7ΔpcaHGΔcatB/pTS084 strain grew by assimilating SA, and produced ccMA from VA over time (the yield was 17 wt % or more). In addition, the yield was determined by the amount of ccMA relative to the amounts of substrates (SA and VA) consumed.

[14. ccMA Production (4) Using a Mixture of SA and VA as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA and 5 mM VA (in this case, a 500 mL baffled flask was used as the culture vessel). The inoculated medium was subjected to rotational culture at 30° C. The addition of 10 mM SA and 5 mM VA was repeated six times every 12 hours from the start of culture.

The OD600 value of the culture broth was measured at regular intervals after the start of culture, and the concentrations of SA, VA, and ccMA in the culture supernatant obtained by centrifugation of the culture broth were measured. The OD600 value and the concentrations of SA, VA, and ccMA were measured in the same way as described in the item 11 above.

Table 16 summarizes the measurement results of OD600 value, SA concentration, VA concentration, and ccMA concentration at 0 hour, 12 hours, 24 hours, 36 hours, 48 hours, 60 hours, and 72 hours after the start of culture.

TABLE 16

| Culture time (h) | 0 | 12 | 24 | 36 | 48 | 60 | 72 |
|---|---|---|---|---|---|---|---|
| OD600 | 0.22 | 1.23 | 2.13 | 3.30 | 4.53 | 4.59 | 4.58 |
| SA (g/L) | 1.93 | 2.34 | 1.89 | 1.82 | 1.78 | 1.76 | 0.41 |
| VA (g/L) | 0.81 | 0.98 | 0.82 | 0.82 | 0.81 | 0.57 | 0.14 |
| ccMA (g/L) | 0 | 0.18 | 1.08 | 1.65 | 2.26 | 2.80 | 3.18 |

As shown in Table 16, even if the addition of SA and VA was repeated at regular intervals, NGC7ΔpcaHGΔcatB/pTS084 strain grew by assimilating SA, and produced ccMA from VA over time.

[15. ccMA Production of using a Mixture of Syringaldehyde (SN) and VN as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 10 mL of Wx minimal medium containing 12.5 mg/L Tc, 10 mM SN and 5 mM VN. The inoculated medium was subjected to shake culture at 30° C.

The concentrations of SN, SA, VN, VA, and ccMA in the culture supernatant obtained by centrifugation of the culture broth were measured at regular intervals after the start of culture. The results are shown in Table 17. The concentrations of SN, SA, VN, VA, and ccMA were measured in the same way as described in the item 11 above. The measurement wavelength was set at 270 nm for SN, and 260 nm for VN.

TABLE 17

| Culture time (h) | 0 | 12 | 24 | 36 |
|---|---|---|---|---|
| OD600 | 0.24 | 0.31 | 1.50 | 1.64 |
| SN (g/L) | 1.59 | 1.03 | 0 | 0 |
| SA (g/L) | 0 | 0.58 | 0.11 | 0 |
| VN (g/L) | 0.65 | 0.16 | 0 | 0 |
| VA (g/L) | 0 | 0.59 | 0.09 | 0.03 |
| ccMA (g/L) | 0 | 0.02 | 0.31 | 0.54 |

As shown in Table 17, NGC7ΔpcaHGΔcatB/pTS084 strain grew by assimilating SN, and produced ccMA from VN over time (the yield was 24.1 wt %). In addition, the yield was determined by the amount of ccMA relative to the amounts of substrates (SN and VN) consumed.

[16. ccMA Production (1) using Birch Lignin-Derived Phenols as a Carbon Source]

According to known methods, birch wood powder was subjected to alcohol-benzene extraction treatment, and then 1.5 g of the treated birch wood powder was subjected to alkaline nitrobenzene oxidative decomposition treatment and further diethyl ether extraction treatment (see "MOKUSHITSU KAGAKU JIKKEN MANUAL", edited by the Japan Wood Research Society, Buneido Co., Ltd., which is incorporated herein by reference in their entirety). The alkaline solution after nitrobenzene oxidative decomposition was subjected to diethyl ether extraction, and the resulting aqueous layer was subjected to acidification treatment and further diethyl ether extraction. The diethyl ether extract obtained as the ether layer was designated as aromatic compounds (phenols) derived from birch lignin, and the ccMA productivity was evaluated in MM medium containing an aqueous solution (pH≈9) of the aromatic compounds derived from birch lignin as a sole carbon source.

NGC7ΔpcaHGΔcatB/pTS084 strain was inoculated into 10 mL of LB liquid medium containing 12.5 mg/L Tc, and shake-cultured at 30° C. for 16 hours. The obtained culture broth was washed with Wx buffer, and then inoculated into 10 mL of Wx minimal medium containing 12.5 mg/L Tc. After adding 60 μL of the aqueous solution of birch lignin-derived phenols as a sole carbon source, the inoculated medium was subjected to shake culture at 30° C. The addition of 60 μL of the aqueous solution of birch lignin-derived phenols was repeated five times every 12 hours after the star of culture.

The OD600 value of the culture broth was measured at regular intervals after the start of culture, and the concentration of ccMA in the culture supernatant obtained by centrifugation of the culture broth was measured. The results are shown in Table 18. The OD600 value and the concentration of ccMA were measured in the same way as described in the item 11 above.

TABLE 18

| Culture time (h) | 0 | 12 | 24 | 36 | 48 | 60 |
|---|---|---|---|---|---|---|
| OD600 | 0.07 | 0.19 | 0.28 | 0.37 | 0.42 | 0.44 |
| ccMA (mg/L) | 0 | 21 | 54 | 85 | 111 | 144 |

As shown in Table 18, NGC7ΔpcaHGΔcatB/pTS084 strain grew by assimilating an aromatic compound derived from birch lignin, and produced ccMA over time.

[17. PCA Production (1) using a Mixture of SA and VA as a Carbon Source]

NGC7ΔpcaHGΔcatB strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA and 5 mM VA (in this case, a 500 mL baffled flask was used as the culture vessel). The inoculated medium was subjected to rotational culture at 30° C.

The OD600 value of the culture broth was measured at regular intervals after the start of culture, and the concentrations of SA, VA and PCA in the culture supernatant obtained by centrifugation of the culture broth were measured. The results are shown in Table 19. The OD600 value and the concentrations of SA, VA, and PCA were measured in the same way as described in the item 11 above. The measurement wavelength was set at 260 nm for PCA.

TABLE 19

| Culture time (h) | 0 | 6 | 12 | 24 |
|---|---|---|---|---|
| SA (g/L) | 1.98 | 1.57 | 0 | 0 |
| VA (g/L) | 1.21 | 0.99 | 0.57 | 0.46 |
| PCA (g/L) | 0 | 0.03 | 0.31 | 0.35 |

As shown in Table 19, NGC7ΔpcaHGΔcatB strain grew by assimilating SA, and produced PCA from VA over time (the yield was 12.8 wt %). In addition, the yield was determined by the amount of PCA relative to the amounts of substrates (SA and VA) consumed.

[18. PCA Production Using a Mixture of SA and HBA as a Carbon Source]

NGC7ΔpcaHGΔcatB strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA and 5 mM HBA (in this case, a 500 mL baffled flask was used as the culture vessel). The inoculated medium was subjected to rotational culture at 30° C.

The OD600 value of the culture broth was measured at regular intervals after the start of culture, and the concentrations of SA, HBA, and PCA in the culture supernatant obtained by centrifugation of the culture broth were measured. The OD600 value and the concentrations of SA, VA, and PCA were measured in the same way as described in the item 11 above. The results are shown in Table 20.

TABLE 20

| Culture time (h) | 0 | 6 | 12 |
|---|---|---|---|
| SA (g/L) | 1.94 | 1.54 | 0 |
| HBA (g/L) | 0.67 | 0.52 | 0 |
| PCA (g/L) | 0 | 0.11 | 0.67 |

As shown in Table 20, NGC7ΔpcaHGΔcatB strain grew by assimilating SA, and produced PCA from HBA over time (the yield was 25.7 wt %). In addition, the yield was determined by the amount of PCA relative to the amounts of substrates (SA and HBA) consumed.

[19. PCA Production Using a Mixture of SA, VA, and HBA as a Carbon Source]

NGC7ΔpcaHGΔcatB strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA, 5 mM VA and 5 mM HBA (in this case, a 500 mL baffled flask was used as the culture vessel). The inoculated medium was subjected to rotational culture at 30° C.

The OD600 value of the culture broth was measured at regular intervals after the start of culture, and the concentrations of SA, VA, HBA, and PCA in the culture supernatant obtained by centrifugation of the culture broth were measured. The OD600 value and the concentrations of SA, VA, and PCA were measured in the same way as described in the item 11 above. The results are shown in Table 21.

TABLE 21

| Culture time (h) | 0 | 6 | 12 | 24 |
|---|---|---|---|---|
| SA (g/L) | 2.00 | 1.81 | 0.71 | 0 |
| VA (g/L) | 1.02 | 1.01 | 0.94 | 0.62 |
| HBA (g/L) | 0.63 | 0.56 | 0.24 | 0 |
| PCA (g/L) | 0 | 0.05 | 0.44 | 0.79 |

As shown in Table 21, NGC7ΔpcaHGΔcatB strain grew by assimilating SA, and produced PCA from VA and HBA over time (the yield was 26.1 wt %). In addition, the yield was determined by the amount of PCA relative to the amounts of substrates (SA, VA, and HBA) consumed.

[20. ccMA Production (5) Using a Mixture of SA and VA as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA and 5 mM VA (in this case, a 500 mL baffled flask was used as the culture vessel). The inoculated medium was subjected to rotational culture at 30° C.

The OD600 value of the culture broth was measured at regular intervals after the start of culture, and the concentrations of SA, VA, and ccMA in the culture supernatant obtained by centrifugation of the culture broth were measured. The results are shown in Table 22. The OD600 value and the concentrations of SA, VA, and ccMA were measured in the same way as described in the item 11 above.

TABLE 22

| Culture time (h) | 0 | 6 | 12 | 24 |
| --- | --- | --- | --- | --- |
| SA (g/L) | 2.09 | 1.78 | 0.05 | 0 |
| VA (g/L) | 1.12 | 0.96 | 0.03 | 0 |
| ccMA (g/L) | 0 | 0.04 | 0.47 | 0.86 |

As shown in Table 22, NGC7ΔpcaHGΔcatB/pTS084 strain grew by assimilating SA, and produced ccMA from VA over time (the yield was 26.8 wt %). In addition, the yield was determined by the amount of ccMA relative to the amounts of substrates (SA and VA) consumed.

[21. ccMA Production Using a Mixture of SA and HBA to Serve as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA and 5 mM HBA (in this case, a 500 mL baffled flask was used as the culture vessel). The inoculated medium was subjected to rotational culture at 30° C.

The OD600 value of the culture broth was measured at regular intervals after the start of culture, and the concentrations of SA, HBA, and ccMA in the culture supernatant obtained by centrifugation of the culture broth were measured. The results are shown in Table 23. The OD600 value and the concentrations of SA, HBA, and ccMA were measured in the same way as described in the item 11 above.

TABLE 23

| Culture time (h) | 0 | 6 | 12 | 24 |
| --- | --- | --- | --- | --- |
| SA (g/L) | 2.12 | 1.76 | 0 | 0 |
| HBA (g/L) | 0.70 | 0.57 | 0 | 0 |
| ccMA (g/L) | 0 | 0.03 | 0.60 | 0.82 |

As shown in Table 23, NGC7ΔpcaHGΔcatB/pTS084 strain grew by assimilating SA, and produced ccMA from HBA over time (the yield was 29.1 wt %). In addition, the yield was determined by the amount of ccMA relative to the amounts of substrates (SA and HBA) consumed.

[22. ccMA Production Using a Mixture of SA, VA, and HBA as a Carbon Source]

NGC7ΔpcaHGΔcatB/pTS084 strain was inoculated into 10 mL of LB liquid medium containing 12.5 mg/L Tc, and shake-cultured at 30° C. for 16 hours. The obtained culture was washed with Wx buffer, and then inoculated into 200 mL of Wx minimal medium containing 12.5 mg/L Tc, 10 mM SA, 5 mM VA, and 5 mM HBA (in this case, a 500 mL baffled flask was used as the culture vessel). The inoculated medium was subjected to rotational culture at 30° C.

The OD600 value of the culture broth was measured at regular intervals after the start of culture, and the concentrations of SA, HBA, and ccMA in the culture supernatant obtained by centrifugation of the culture broth were measured. The OD600 value and the concentrations of SA, HBA, and ccMA were measured in the same way as described in the item 11 above.

TABLE 24

| Culture time (h) | 0 | 6 | 12 | 24 |
| --- | --- | --- | --- | --- |
| SA (g/L) | 1.99 | 1.75 | 0.27 | 0 |
| VA (g/L) | 1.00 | 0.85 | 0.20 | 0 |
| HBA (g/L) | 0.63 | 0.52 | 0.04 | 0 |
| ccMA (g/L) | 0 | 0 | 0.46 | 1.00 |

As shown in Table 24, NGC7ΔpcaHGΔcatB/pTS084 strain grew by assimilating SA, and produced ccMA from VA and HBA over time (the yield was 27.6 wt %). In addition, the yield was determined by the amount of ccMA relative to the amounts of substrates (SA, VA, and HBA) consumed.

[23. ccMA Production (3) Using a Mixture of VA and HBA as a Carbon Source]

NGC7ΔpcaHGΔcatB/pTS119 strain was inoculated into 10 mL of LB liquid medium containing 25 mg/L of nalidixic acid (Nal), 25 mg/L of Km, 50 mg/L of gentamicin (Gm) and 20 mg/L Tc, and then shake-cultured at 30° C. overnight. The obtained culture medium (1 mL) was inoculated into 0.1 L of MM liquid medium containing 25 mg/L of Nal, 25 mg/L of Km, 50 mg/L of Gm, 20 mg/L Tc, 25 mM VA, and 25 mM HBA, and subjected to stirred aerated culture at 30° C., pH 7, for 32 hours to 52 hours while keeping the dissolved oxygen concentration (DO) within a certain range during the culture period. The DO sensor used was calibrated with air-saturated MM medium (DO=100%) and 5% sodium sulfite solution (DO=0%) before the start of culture.

The concentrations of VA, HBA, and ccMA after the culture were measured in the same way as described in the item 3 above. Based on the measurement results obtained, the yield of ccMA was determined by the amount of ccMA relative to the amounts of substrates (VA and HBA) consumed. Table 25 summarizes the measurement results of the yield of ccMA and the DO value kept.

TABLE 25

| DO (%) | 2.5 | 5 | 10 | 15 |
| --- | --- | --- | --- | --- |
| ccMA yield (wt %) | 25.6 | 23.3 | 24.4 | 17.8 |

As shown in Table 25, the yield of ccMA produced was excellent under the conditions where the dissolved oxygen concentration in the culture broth was in the range between 2.5% and 10% (the yield was about 23 wt % or higher).

[24. ccMA Production (4) Using a Mixture of VA and HBA as a Carbon Source]

NGC7ΔpcaHGΔcatB/pTS119 strain was inoculated into 10 mL of LB liquid medium containing 20 mg/L Tc, and shake-cultured at 30° C. overnight. The resulting cells were washed with saline, and then suspended in saline such that OD600 value becomes 50.

The resulting suspension (1 mL) was inoculated into 0.1 L of MMx-3 liquid medium (34.2 g/L Na2HPO4.12H$_2$O, 6.0 g/L KH$_2$PO$_4$, 2.5 g/L (NH$_4$)$_2$SO$_4$, 1 g/L NaCl, 0.49 g/L MgSO$_4$.7H$_2$O, 0.005 g/L FeSO$_4$.7H$_2$O, 0.015 g/L CaCl$_2$.2H$_2$O) containing 20 mg/L Tc, 25 mM VA and 25 mM HBA, and then subjected to stirred aerated culture at 30° C., pH 7 while keeping the dissolved oxygen concentration (DO) at 2.5%. The DO sensor used was calibrated with air-saturated MMx-3 liquid medium (DO=100%) and 5% sodium sulfite solution (DO=0%) before the start of culture.

Feeding solution (100 g/L VA, 82.1 g/L HBA, 148.8 g/L (NH$_4$)$_2$SO$_4$) was added every 2 hours in the range of 0.42 g to 2.52 g in accordance with the consumption rates of VA and HBA, starting when the concentration of VA decreased to equal to or less than 1 g/L.

At regular intervals after the start of culture, OD600 value of the culture broth as well as the concentrations of VA, HBA, and ccMA in the culture broth were measured. The OD600 value and the concentrations of VA, HBA, and ccMA were measured in the same way as described in the item 3 above. Table 26 summarizes the measurement results of OD600 value, VA concentration, HBA concentration, and ccMA concentration at 0 hour, 12 hours, 24 hours, 36 hours, 48 hours, and 52 hours after the start of culture.

TABLE 26

| Culture time (h) | 0 | 12 | 24 | 36 | 48 | 52 |
|---|---|---|---|---|---|---|
| OD600 | 0.6 | 1.1 | 1.7 | 6.5 | 15.3 | 16.8 |
| VA (g/L) | 1.68 | 1.29 | 1.50 | 1.02 | 1.5 | 2.63 |
| HBA (g/L) | 1.41 | 0.89 | 0.62 | 0.63 | 1.65 | 2.90 |
| ccMA (g/L) | 0 | 0.13 | 0.72 | 3.02 | 8.40 | 9.99 |

As shown in Table 26, NGC7ΔpcaHGΔcatB/pTS119 strain grew by assimilating VA and HBA, and produced ccMA over time at a high concentration.

INDUSTRIAL APPLICABILITY

Using the transformed microorganisms and production methods according to one embodiment of the present invention, muconic acid and protocatechuic acid can be obtained from biomass containing lignin and lignin-derived aromatic compounds. Muconic acid can be used, for example, as a raw material of muconic acid derivatives expected to be used as surfactants, flame retardants, UV light stabilizers, thermosetting plastics, and coating agents.

CROSS-REFERENCE TO RELATED APPLICATIONS

The present application claims the benefit of priority to Japanese Patent Application No. 2018-196001, filed on Oct. 17, 2018, the disclosure of which is incorporated herein by reference in its entirety.

Sequence Listing

19DF0933PCT_ST25.txt

The invention claimed is:

1. A transformed microorganism wherein the host microorganism is a microorganism of the genus *Pseudomonas* that has pcaH gene, pcaG gene, catA gene, and catB gene on its chromosome, and that can assimilate an aromatic compound derived from syringyl lignin; and wherein the transformed microorganism lacks at least one gene selected from the group consisting of pcaH gene and pcaG gene on its chromosome, and lacks catB gene on its chromosome, and expresses aroY gene inserted.

2. The transformed microorganism according to claim 1, wherein further expresses at least one gene selected from the group consisting of catA gene inserted, vanA gene inserted, vanB gene inserted, and kpdB gene inserted.

3. The transformed microorganism according to claim 1, wherein the microorganism of the genus *Pseudomonas* is selected from the group consisting of *P. putida, P. plecoglossicida, P. taiwanensis, P. monteilii, P. fulva*, and *Pseudomonas* species which is a related species to them.

4. A method of producing muconic acid, comprising a step of applying an aromatic compound derived from p-hydroxyphenyl lignin and/or an aromatic compound derived from guaiacyl lignin, and an aromatic compound derived from syringyl lignin to the transformed microorganism according to claim 1 to obtain muconic acid.

5. The transformed microorganism of claim 1, wherein the host microorganism is *Pseudomonas* sp. NGC7 strain.

* * * * *

SEQUENCE LISTING

<160> NUMBER OF SEQ ID NOS: 55

<210> SEQ ID NO 1
<211> LENGTH: 36
<212> TYPE: DNA
<213> ORGANISM: Artificial sequence
<220> FEATURE:
<223> OTHER INFORMATION: Primer

<400> SEQUENCE: 1
tgattacgcc aagcttcgtg atcgcacctg gcatcc                    36

<210> SEQ ID NO 2
<211> LENGTH: 38
<212> TYPE: DNA
<213> ORGANISM: Artificial sequence
<220> FEATURE:
<223> OTHER INFORMATION: Primer

<400> SEQUENCE: 2
gacggccagt gaattcagat gtcgaagaag accgtttc                  38

<210> SEQ ID NO 3
<211> LENGTH: 39
<212> TYPE: DNA
<213> ORGANISM: Artificial sequence
<220> FEATURE:
<223> OTHER INFORMATION: Primer

<400> SEQUENCE: 3
tgattacgcc aagcttacca tccgcccgca caagctggc                 39

<210> SEQ ID NO 4
<211> LENGTH: 39
<212> TYPE: DNA
<213> ORGANISM: Artificial sequence
<220> FEATURE:
<223> OTHER INFORMATION: Primer

<400> SEQUENCE: 4
gacggccagt gaattctcgc gggtggcgta ggcgaagtc                 39

<210> SEQ ID NO 5
<211> LENGTH: 34
<212> TYPE: DNA
<213> ORGANISM: Artificial sequence
<220> FEATURE:
<223> OTHER INFORMATION: Primer

<400> SEQUENCE: 5
atgtgaattg cggccagcgc ccaatacgca aacc                          34

<210> SEQ ID NO 6
<211> LENGTH: 40
<212> TYPE: DNA
<213> ORGANISM: Artificial sequence
<220> FEATURE:
<223> OTHER INFORMATION: Primer

<400> SEQUENCE: 6
tctggtaccg cggccgcgta atcatggtca tagctgtttc                    40

<210> SEQ ID NO 7
<211> LENGTH: 49
<212> TYPE: DNA
<213> ORGANISM: Artificial sequence
<220> FEATURE:
<223> OTHER INFORMATION: Primer

<400> SEQUENCE: 7
atgcgagctc attaaagagg agaaattaac tatgcccgcc caggacaac          49

<210> SEQ ID NO 8
<211> LENGTH: 30
<212> TYPE: DNA
<213> ORGANISM: Artificial sequence
<220> FEATURE:
<223> OTHER INFORMATION: Primer

<400> SEQUENCE: 8
atgcggatcc cccaagcttc acctcagaag                               30

<210> SEQ ID NO 9
<211> LENGTH: 49
<212> TYPE: DNA
<213> ORGANISM: Artificial sequence
<220> FEATURE:
<223> OTHER INFORMATION: Primer

<400> SEQUENCE: 9
agctggtacc attaaagagg agaaattaac tatgaccgca ccgattcag          49

<210> SEQ ID NO 10
<211> LENGTH: 31
<212> TYPE: DNA
<213> ORGANISM: Artificial sequence
<220> FEATURE:
<223> OTHER INFORMATION: Primer

<400> SEQUENCE: 10
agctggtacc ttattttgcg ctaccctggt t                             31

<210> SEQ ID NO 11
<211> LENGTH: 53
<212> TYPE: DNA
<213> ORGANISM: Artificial sequence
<220> FEATURE:

<223> OTHER INFORMATION: Primer

<400> SEQUENCE: 11
catgattacg cggccgcatt aaagaggaga aattaactat gaccgcaccg att         53

<210> SEQ ID NO 12
<211> LENGTH: 36
<212> TYPE: DNA
<213> ORGANISM: Artificial sequence
<220> FEATURE:
<223> OTHER INFORMATION: Primer

<400> SEQUENCE: 12
tctggtaccg cggccttatt ttgcgctacc ctggtt                            36

<210> SEQ ID NO 13
<211> LENGTH: 50
<212> TYPE: DNA
<213> ORGANISM: Artificial sequence
<220> FEATURE:
<223> OTHER INFORMATION: Primer

<400> SEQUENCE: 13
atgcggtacc ttaaagagga gaaattaact atgaccgtga aaatttccca             50

<210> SEQ ID NO 14
<211> LENGTH: 30
<212> TYPE: DNA
<213> ORGANISM: Artificial sequence
<220> FEATURE:
<223> OTHER INFORMATION: Primer

<400> SEQUENCE: 14
agctcccggg tcagccctcc tgcaacgccc                                   30

<210> SEQ ID NO 15
<211> LENGTH: 47
<212> TYPE: DNA
<213> ORGANISM: Artificial sequence
<220> FEATURE:
<223> OTHER INFORMATION: Primer

<400> SEQUENCE: 15
catgattacg cggccgctta aagaggagaa attaactatg accgtga                47

<210> SEQ ID NO 16
<211> LENGTH: 33
<212> TYPE: DNA
<213> ORGANISM: Artificial sequence
<220> FEATURE:
<223> OTHER INFORMATION: Primer

<400> SEQUENCE: 16
ctctttaatg cggcctcagc cctcctgcaa cgc                               33

<210> SEQ ID NO 17
<211> LENGTH: 29
<212> TYPE: DNA
<213> ORGANISM: Artificial sequence
<220> FEATURE:
<223> OTHER INFORMATION: Primer

<400> SEQUENCE: 17
atgcgagctc atgtacccca aaaacacct                                    29

```
<210> SEQ ID NO 18
<211> LENGTH: 29
<212> TYPE: DNA
<213> ORGANISM: Artificial sequence
<220> FEATURE:
<223> OTHER INFORMATION: Primer

<400> SEQUENCE: 18
atgcccgggt cagatgtcca gcaccagca                                    29

<210> SEQ ID NO 19
<211> LENGTH: 35
<212> TYPE: DNA
<213> ORGANISM: Artificial sequence
<220> FEATURE:
<223> OTHER INFORMATION: Primer

<400> SEQUENCE: 19
catgattacg cggccattaa agaggagaaa ttaac                             35

<210> SEQ ID NO 20
<211> LENGTH: 35
<212> TYPE: DNA
<213> ORGANISM: Artificial sequence
<220> FEATURE:
<223> OTHER INFORMATION: Primer

<400> SEQUENCE: 20
cctctttaag cggccgctca gatgtccagc accag                             35

<210> SEQ ID NO 21
<211> LENGTH: 38
<212> TYPE: DNA
<213> ORGANISM: Artificial sequence
<220> FEATURE:
<223> OTHER INFORMATION: Primer

<400> SEQUENCE: 21
tcaccatggg aagctattaa agaggagaaa ttaactat                          38

<210> SEQ ID NO 22
<211> LENGTH: 33
<212> TYPE: DNA
<213> ORGANISM: Artificial sequence
<220> FEATURE:
<223> OTHER INFORMATION: Primer

<400> SEQUENCE: 22
tggatccacg aagctcccaa gcttcacctc aga                               33

<210> SEQ ID NO 23
<211> LENGTH: 55
<212> TYPE: DNA
<213> ORGANISM: Artificial sequence
<220> FEATURE:
<223> OTHER INFORMATION: Primer

<400> SEQUENCE: 23
agctgaattc attaaagagg agaaattaac tatgaaactg attattggga tgacg       55

<210> SEQ ID NO 24
<211> LENGTH: 32
<212> TYPE: DNA
<213> ORGANISM: Artificial sequence
<220> FEATURE:
<223> OTHER INFORMATION: Primer
```

<400> SEQUENCE: 24
agcttctaga ttattcgatc tcctgtgcaa at                                        32

<210> SEQ ID NO 25
<211> LENGTH: 51
<212> TYPE: DNA
<213> ORGANISM: Artificial sequence
<220> FEATURE:
<223> OTHER INFORMATION: Primer

<400> SEQUENCE: 25
gaagcttcgt ggatcattaa agaggagaaa ttaactatga ccgcaccgat t                   51

<210> SEQ ID NO 26
<211> LENGTH: 38
<212> TYPE: DNA
<213> ORGANISM: Artificial sequence
<220> FEATURE:
<223> OTHER INFORMATION: Primer

<400> SEQUENCE: 26
acgtctcgag gaattcttat tcgatctcct gtgcaaat                                  38

<210> SEQ ID NO 27
<211> LENGTH: 45
<212> TYPE: DNA
<213> ORGANISM: Artificial sequence
<220> FEATURE:
<223> OTHER INFORMATION: Primer

<400> SEQUENCE: 27
cggccgcggt accagttaaa gaggagaaat taactatgac cgtga                          45

<210> SEQ ID NO 28
<211> LENGTH: 34
<212> TYPE: DNA
<213> ORGANISM: Artificial sequence
<220> FEATURE:
<223> OTHER INFORMATION: Primer

<400> SEQUENCE: 28
ctagatacct aggtgtcagc cctcctgcaa cgcc                                      34

<210> SEQ ID NO 29
<211> LENGTH: 34
<212> TYPE: DNA
<213> ORGANISM: Artificial sequence
<220> FEATURE:
<223> OTHER INFORMATION: Primer

<400> SEQUENCE: 29
atgtgaattg cggccagcgc ccaatacgca aacc                                      34

<210> SEQ ID NO 30
<211> LENGTH: 40
<212> TYPE: DNA
<213> ORGANISM: Artificial sequence
<220> FEATURE:
<223> OTHER INFORMATION: Primer

<400> SEQUENCE: 30
actggtaccg cggccgcgta atcatggtca tagctgtttc                                40

<210> SEQ ID NO 31
<211> LENGTH: 35

```
<212> TYPE: DNA
<213> ORGANISM: Artificial sequence
<220> FEATURE:
<223> OTHER INFORMATION: Primer

<400> SEQUENCE: 31
catgattacg cggccattaa agaggagaaa ttaac                               35

<210> SEQ ID NO 32
<211> LENGTH: 35
<212> TYPE: DNA
<213> ORGANISM: Artificial sequence
<220> FEATURE:
<223> OTHER INFORMATION: Primer

<400> SEQUENCE: 32
actggtaccg cggcctcaga tgtccagcac cagca                               35

<210> SEQ ID NO 33
<211> LENGTH: 197
<212> TYPE: PRT
<213> ORGANISM: Klebsiella pneumoniae subsp. pneumoniae

<400> SEQUENCE: 33
```

Met Lys Leu Ile Ile Gly Met Thr Gly Ala Thr Gly Ala Pro Leu Gly
1               5                   10                  15

Val Ala Leu Leu Gln Ala Leu Arg Asp Met Pro Glu Val Glu Thr His
            20                  25                  30

Leu Val Met Ser Lys Trp Ala Lys Thr Thr Ile Glu Leu Glu Thr Pro
        35                  40                  45

Trp Thr Ala Arg Glu Val Ala Ala Leu Ala Asp Phe Ser His Ser Pro
    50                  55                  60

Ala Asp Gln Ala Ala Thr Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Glu Gly Leu Val Gly Arg Ala Ala Asp Val Val Leu Lys
            100                 105                 110

Glu Gly Arg Lys Leu Val Leu Val Pro Arg Glu Met Pro Leu Ser Thr
        115                 120                 125

Ile His Leu Glu Asn Met Leu Ala Leu Ser Arg Met Gly Val Ala Met
    130                 135                 140

Val Pro Pro Met Pro Ala Tyr Tyr Asn His Pro Glu Thr Val Asp Asp
145                 150                 155                 160

Ile Thr Asn His Ile Val Thr Arg Val Leu Asp Gln Phe Gly Leu Asp
                165                 170                 175

Tyr His Lys Ala Arg Arg Trp Asn Gly Leu Arg Thr Ala Glu Gln Phe
            180                 185                 190

Ala Gln Glu Ile Glu
        195

```
<210> SEQ ID NO 34
<211> LENGTH: 395
<212> TYPE: PRT
<213> ORGANISM: Pseudomonas putida

<400> SEQUENCE: 34
```

Met Lys Thr Gln Val Ala Ile Ile Gly Ala Gly Pro Ser Gly Leu Leu
1               5                   10                  15

```
Leu Gly Gln Leu Leu His Lys Ala Gly Ile Asp Asn Ile Ile Val Glu
             20                  25                  30

Arg Gln Thr Ala Glu Tyr Val Leu Gly Arg Ile Arg Ala Gly Val Leu
         35                  40                  45

Glu Gln Gly Thr Val Asp Leu Leu Arg Glu Ala Gly Val Ala Glu Arg
     50                  55                  60

Met Asp Arg Glu Gly Leu Val His Glu Gly Val Glu Leu Leu Val Gly
 65                  70                  75                  80

Gly Arg Arg Gln Arg Leu Asp Leu Lys Ala Leu Thr Gly Gly Lys Thr
                 85                  90                  95

Val Met Val Tyr Gly Gln Thr Glu Val Thr Arg Asp Leu Met Gln Ala
            100                 105                 110

Arg Glu Ala Ser Gly Ala Pro Ile Ile Tyr Ser Ala Ala Asn Val Gln
        115                 120                 125

Pro His Glu Leu Lys Gly Glu Lys Pro Tyr Leu Thr Phe Glu Lys Asp
    130                 135                 140

Gly Arg Val Gln Arg Ile Asp Cys Asp Tyr Ile Ala Gly Cys Asp Gly
145                 150                 155                 160

Phe His Gly Ile Ser Arg Gln Ser Ile Pro Glu Gly Val Leu Lys Gln
                165                 170                 175

Tyr Glu Arg Val Tyr Pro Phe Gly Trp Leu Gly Leu Leu Ser Asp Thr
            180                 185                 190

Pro Pro Val Asn His Glu Leu Ile Tyr Ala His Glu Arg Gly Phe
        195                 200                 205

Ala Leu Cys Ser Gln Arg Ser Gln Thr Arg Ser Arg Tyr Tyr Leu Gln
    210                 215                 220

Val Pro Leu Gln Asp Arg Val Glu Glu Trp Ser Asp Glu Arg Phe Trp
225                 230                 235                 240

Asp Glu Leu Lys Ala Arg Leu Pro Ala Glu Val Ala Asp Leu Val
                245                 250                 255

Thr Gly Pro Ala Leu Glu Lys Ser Ile Ala Pro Leu Arg Ser Leu Val
            260                 265                 270

Val Glu Pro Met Gln Tyr Gly His Leu Phe Leu Val Gly Asp Ala Ala
    275                 280                 285

His Ile Val Pro Pro Thr Gly Ala Lys Gly Leu Asn Leu Ala Ala Ser
290                 295                 300

Asp Val Asn Tyr Leu Tyr Arg Ile Leu Val Lys Val Tyr His Glu Gly
305                 310                 315                 320

Arg Val Asp Leu Leu Ala Gln Tyr Ser Pro Leu Ala Leu Arg Arg Val
            325                 330                 335

Trp Lys Gly Glu Arg Phe Ser Trp Phe Met Thr Gln Leu Leu His Asp
        340                 345                 350

Phe Gly Ser His Lys Asp Ala Trp Asp Gln Lys Met Gln Glu Ala Asp
    355                 360                 365

Arg Glu Tyr Phe Leu Thr Ser Pro Ala Gly Leu Val Asn Ile Ala Glu
    370                 375                 380

Asn Tyr Val Gly Leu Pro Phe Glu Glu Val Ala
385                 390                 395

<210> SEQ ID NO 35
<211> LENGTH: 355
<212> TYPE: PRT
<213> ORGANISM: Pseudomonas putida

<400> SEQUENCE: 35
```

Met Tyr Pro Lys Asn Thr Trp Tyr Val Ala Cys Thr Pro Asp Glu Ile
1               5                   10                  15

Ala Thr Lys Pro Leu Gly Arg Gln Ile Cys Gly Glu Lys Ile Val Phe
            20                  25                  30

Tyr Arg Ala Arg Glu Asn Gln Val Ala Ala Val Glu Asp Phe Cys Pro
        35                  40                  45

His Arg Gly Ala Pro Leu Ser Leu Gly Tyr Val Glu Asp Gly Asn Leu
    50                  55                  60

Val Cys Gly Tyr His Gly Leu Val Met Gly Cys Asp Gly Lys Thr Val
65                  70                  75                  80

Ser Met Pro Gly Gln Arg Val Arg Gly Phe Pro Cys Asn Lys Thr Phe
                85                  90                  95

Ala Ala Val Glu Arg Tyr Gly Phe Ile Trp Val Trp Pro Gly Asp Gln
                100                 105                 110

Ala Gln Ala Asp Pro Ala Leu Ile Pro His Leu Glu Trp Ala Val Ser
        115                 120                 125

Asp Glu Trp Ala Tyr Gly Gly Leu Phe His Ile Gly Cys Asp Tyr
        130                 135                 140

Arg Leu Met Ile Asp Asn Leu Met Asp Leu Thr His Glu Thr Tyr Val
145                 150                 155                 160

His Ala Ser Ser Ile Gly Gln Lys Glu Ile Asp Glu Ala Pro Pro Val
                165                 170                 175

Thr Thr Val Thr Gly Asp Glu Val Val Thr Ala Arg His Met Glu Asn
                180                 185                 190

Ile Met Ala Pro Pro Phe Trp Arg Met Ala Leu Arg Gly Asn Gly Leu
                195                 200                 205

Ala Asp Asp Val Pro Val Asp Arg Trp Gln Ile Cys Arg Phe Thr Pro
210                 215                 220

Pro Ser His Val Leu Ile Glu Val Gly Val Ala His Ala Gly Lys Gly
225                 230                 235                 240

Gly Tyr His Ala Glu Ala Gln His Lys Ala Ser Ser Ile Val Val Asp
                245                 250                 255

Phe Ile Thr Pro Glu Ser Asp Thr Ser Ile Trp Tyr Phe Trp Gly Met
                260                 265                 270

Ala Arg Asn Phe Ala Ala His Asp Gln Thr Leu Thr Asp Asn Ile Arg
            275                 280                 285

Glu Gly Gln Gly Lys Ile Phe Ser Glu Asp Leu Glu Met Leu Glu Arg
            290                 295                 300

Gln Gln Gln Asn Leu Leu Ala His Pro Glu Arg Asn Leu Leu Lys Leu
305                 310                 315                 320

Asn Ile Asp Ala Gly Gly Val Gln Ser Arg Lys Val Leu Glu Arg Ile
                325                 330                 335

Ile Ala Gln Glu Arg Ala Pro Gln Pro Gln Leu Ile Ala Thr Ser Ala
            340                 345                 350

Asn Pro Ala
        355

<210> SEQ ID NO 36
<211> LENGTH: 316
<212> TYPE: PRT
<213> ORGANISM: Pseudomonas putida

<400> SEQUENCE: 36

Met Ile Asp Ala Val Val Val Ser Arg Asn Asp Glu Ala Gln Gly Ile

```
  1               5                  10                 15
Cys Ser Phe Glu Leu Ala Ala Ala Asp Gly Ser Leu Leu Pro Ala Phe
             20                 25                 30

Ser Ala Gly Ala His Ile Asp Val His Leu Pro Asp Gly Leu Val Arg
             35                 40                 45

Gln Tyr Ser Leu Cys Asn His Pro Glu Glu Arg His Arg Tyr Leu Ile
             50                 55                 60

Gly Val Leu Asn Asp Pro Ala Ser Arg Gly Ser Arg Ser Leu His
 65                 70                 75                 80

Glu Gln Val Gln Ala Gly Ala Arg Leu Arg Ile Ser Ala Pro Arg Asn
                 85                 90                 95

Leu Phe Pro Leu Ala Glu Gly Ala Gln Arg Ser Leu Leu Phe Ala Gly
            100                105                110

Gly Ile Gly Ile Thr Pro Ile Leu Cys Met Ala Glu Gln Leu Ser Asp
            115                120                125

Ser Gly Gln Ala Phe Glu Leu His Tyr Cys Ala Arg Ser Ser Glu Arg
            130                135                140

Ala Ala Phe Val Glu Arg Ile Arg Ser Ala Pro Phe Ala Asp Arg Leu
145                150                155                160

Phe Val His Phe Asp Glu Gln Pro Glu Thr Ala Leu Asp Ile Ala Gln
            165                170                175

Val Leu Gly Asn Pro Gln Asp Val His Leu Tyr Val Cys Gly Pro
            180                185                190

Gly Gly Phe Met Gln His Val Leu Asp Ser Ala Lys Gly Leu Gly Trp
            195                200                205

Gln Glu Ala Asn Leu His Arg Glu Tyr Phe Ala Ala Pro Val Asp
            210                215                220

Ala Ser Asn Asp Gly Ser Phe Ala Val Gln Val Gly Ser Thr Gly Gln
225                230                235                240

Val Phe Glu Val Pro Ala Asp Arg Thr Val Gln Val Leu Glu Glu
            245                250                255

Asn Gly Ile Glu Ile Ala Met Ser Cys Glu Gln Gly Ile Cys Gly Thr
            260                265                270

Cys Leu Thr Arg Val Leu Gln Gly Thr Pro Asp His Arg Asp Leu Phe
            275                280                285

Leu Thr Glu Glu Glu Gln Ala Leu Asn Asp Gln Phe Thr Pro Cys Cys
            290                295                300

Ser Arg Ser Lys Thr Pro Leu Leu Val Leu Asp Ile
305                310                315

<210> SEQ ID NO 37
<211> LENGTH: 720
<212> TYPE: DNA
<213> ORGANISM: Pseudomonas putida

<400> SEQUENCE: 37
atgcccgccc aggacaacag ccgcttcgtg atccgtgatc gcaactggca ccctaaagcc      60
cttacgcctg actacaagac ctccgttgcc cgctcgccgc gccaggcact ggtcagcatt     120
ccgcagtcga tcagcgaaac cactggtccg acttttccc atctgggctt cggcgcccac     180
gaccatgacc tgctgctgaa cttcaataac ggtggcctgc ccattggcga cgcatcatc     240 gtcgccggcc gtgtcgtcga ccagtacggc aagcctgtgc cgaacacttt ggtggagatg     300
tggcaagcca acgccggcgg ccgctatcgc cacaagaacg atcgctacct ggcgcccctg     360
```

```
gacccgaact tcggtggtgt tgggcggtgt ctgaccgacc gtgacggcta ttacagcttc    420
cgcaccatca agccgggccc gtacccatgg cgcaacggcc cgaacgactg gcgcccggcg    480
catatccact tcgccatcag cggcccatcg atcgccacca agctgatcac ccagttgtac    540
ttcgaaggtg acccgctgat cccgatgtgc ccgatcgtca agtcgatcgc caacccgcaa    600
gccgtgcagc agttgatcgc caagctcgac atgagcaacg ccaacccgat ggactgcctg    660
gcctaccgct ttgacatcgt gctgcgcggc cagcgcaaga cccacttcga aaactgctga    720

<210> SEQ ID NO 38
<211> LENGTH: 606
<212> TYPE: DNA
<213> ORGANISM: Pseudomonas putida

<400> SEQUENCE: 38
atgccaatcg aactgctgcc ggaaacccct tcgcagactg ccggccccta cgtgcacatc     60
ggcctggccc tggaagccgc cggcaacccg accgcgacc aggaaatctg gaactgcctg    120
gccaagccag acgccccggg cgagcacatt ctgctgatcg ccacgtata tgacggaaac    180 ggccacctgg tgcgcgactc gttcctggaa gtgtggcagg ccgacgccaa cggtgagtac    240
caggatgcct acaacctgga aaacgccttc aacagctttg ccgcacggc taccaccttc    300 gatgccggtg agtggacgct gcaaacggtc aagccgggtg tggtgaacaa cgctgctggc    360
gtgccgatgg cgccgcacat caacatcagc ctgtttgccc gtggcatcaa catccacctg    420
cacacgcgcc tgtatttcga tgatgaggcc caggccaatg ccaagtgccc ggtgctcaac    480
ctgatcgagc agccgcagcg gcgtgaaacc ttgattgcca agcgttgcga agtggatggg    540
aagacggcgt accgctttga tatccgcatt cagggggaag gggagaccgt cttcttcgac    600
ttctga                                                               606

<210> SEQ ID NO 39
<211> LENGTH: 936
<212> TYPE: DNA
<213> ORGANISM: Pseudomonas putida

<400> SEQUENCE: 39
atgaccgtga aaatttccca cactgccgac attcaagcct tcttcaaccg ggtagctggc     60
ctggaccatg ccgaaggaaa cccgcgcttc aagcagatca ttctgcgcgt gctgcaagac    120
accgcccgcc tgatcgaaga cctggagatt accgaggacg agttctggca cgccgtcgac    180
tacctcaacc gcctgggcgg ccgtaacgag gcaggcctgc tggctgctgg cctgggtatc    240
gagcacttcc tcgacctgct gcaggatgcc aaggatgccg aagccggcct tggcggcggc    300
accccgcgca ccatcgaagg cccgttgtac gttgccgggg cgccgctggc ccagggcgaa    360
gcgcgcatgg acgacggcac tgacccaggc gtggtgatgt tccttcaggg ccaggtgttc    420
gatgccgacg gcaagccgtt ggccggtgcc accgtcgacc tgtggcacgc caatacccag    480 ggcaccatt cgtacttcga ttcgacccag tccgagttca acctgcgtcg gcgtatcatc    540
accgatgccg agggccgcta ccgcgcgcgc tcgatcgtgc cgtccgggta tggctgcgac    600
ccgcagggcc caaccagga atgcctggac ctgctcggcc gccacggcca gcgcccggcg    660
cacgtgcact tcttcatctc ggcaccgggg caccgccacc tgaccacgca gatcaacttt    720
gctggcgaca gtacctgtg ggacgacttt gcctatgcca cccgcgacgg gctgatcggc    780
gaactgcgtt ttgtcgagga tgcggcggcg gcgcgcgacc gcggtgtgca aggcgagcgc    840
tttgccgagc tgtcattcga cttccgcttg cagggtgcca agtcgcctga cgccgaggcg    900
```

```
                cgaagccatc ggccgcgggc gttgcaggag ggctga              936
```

<210> SEQ ID NO 40
<211> LENGTH: 1122
<212> TYPE: DNA
<213> ORGANISM: Pseudomonas putida

<400> SEQUENCE: 40

```
atgacaagcg tgctgattga acacatagat gcaattatcg tcgatctccc gaccattcgc     60
ccgcacaagc tggcgatgca caccatgcag cagcagaccc tggtggtatt gcgactgcgc    120
tgcagcgatg gcgtggaagg catcggtgaa gccaccacca tcggtggcct ggcgtatggc    180
tacgaaagcc ccgaagggat caaggccaac atcgacgcgt acctcgcccc agcgttgatt    240
ggcctgccgg cagacaacat caatgccgcc atgctcaagc tggacaagct ggccaagggc    300
aacaccttcg ccaagtccgg catcgaaagc gccttgctcg acgcccaggg caaacgcctg    360
ggcctgccgg tcagcgaact gctggtggcg cgcgtgcgtg acagcctgga agtggcctgg    420
accctggcca gcggcgacac cgccgcgac atcgccgaag cacagcacat gctggacatt     480
cgccggcacc gcgtgttcaa gctgaaaatc ggcgccaacc cggtggcgca ggacctcaag    540
cacgtggtcg cgatcaagcg cgagctgggt gacagcgcca gcgtgcgggt cgacgtcaac    600
cagtactggg acgagtccca ggccatccgc gcctgccagg tattgggcga caacggcatc    660
gacctgatcg agcagccgat ttcgcgcatc aaccgcgctg gccaggtgcg cctgaaccag    720
cgcagtccgg ctccgatcat ggccgatgag tcgatcgaaa cgtcgaggga cgccttcagc    780
ctggccgccg acggcgccgc cagcatcttc gccctgaaaa tcgccaagaa tggtggcccg    840
cgcgcggttc tgcgcactgc acagatcgcc gaggccgctg catcgccctt gtacggcggc    900
accatgctcg aaggttcgat cggcaccctg gcttcggctc atgcattcct cacccctgcgc   960
cagctcacct ggggtacaga gctgttcggg ccgctgctgc tgaccgagga gatcgtcaac   1020
gagccgccgc aataccgcga cttccagctg cacatccccc acaccccagg cctgggcctg   1080
acgttggacg aacagcgcct ggcgcgcttc gcccgtcgct ga                      1122
```

<210> SEQ ID NO 41
<211> LENGTH: 1509
<212> TYPE: DNA
<213> ORGANISM: Klebsiella pneumoniae subsp. pneumoniae

<400> SEQUENCE: 41

```
atgaccgcac cgattcagga tctgcgcgac gccatcgcgc tgctgcaaca gcatgacaat     60
cagtatctcg aaaccgatca tccggttgac cctaacgccg agctggccgg tgtttatcgc    120
catatcggcg cgggcggcac cgtgaagcgc cccacccgca tcgggccggc gatgatgttt    180
aacaatatta agggttatcc acactcgcgc attctggtgg gtatgcacgc cagccgccag    240
cgggccgcgc tgctgctggg ctgcgaagcc tcgcagctgg cccttgaagt gggtaaggcg    300
gtgaaaaaac cggtcgcgcc ggtggtcgtc ccggccagca gcgcccctg ccaggaacag    360
atctttctgg ccgacgatcc ggatttgat ttgcgcaccc tgcttccggc gcccaccaac    420
accctatcg acgccggccc cttcttctgc ctgggcctgg cgctgccag cgatcccgtc    480
gacgcctcgc tgaccgacgt caccatccac cgcttgtgcg tccagggccg ggatgagctg    540
tcgatgttcc ttgccgccgg ccgccatatc gaagtgtttc gccaaaaggc cgaggccgcc    600
ggcaaaccgc tgccgataac catcaatatg ggtctcgatc cggccatcta tattggcgcc    660
```

```
tgcttcgaag cccctaccac gccgttcggc tataatgagc tgggcgtcgc cggcgcgctg    720
cgtcaacgtc cggtggagct ggttcagggc gtcagcgtcc ggagaaagc catcgcccgc     780 gccgagatcg ttatcgaagg tgagctgttg cctggcgtgc gcgtcagaga ggatcagcac    840
accaatagcg gccacgcgat gccggaattt cctggctact cggcggcgc taatccgtcg     900 ctgccggtaa tcaaagtcaa agcagtgacc atgcgaaaca atgcgattct gcagaccctg    960
gtgggaccgg gggaagagca taccaccctc gccggcctgc caacgaaagc cagtatctgg   1020
aatgccgtcg aggccgccat tccgggcttt ttacaaaatg tctacgccca caccgcgggt   1080
ggcggtaagt tcctcgggat cctgcaggtg aaaaaacgtc aacccgccga tgaaggccgg   1140
caggggcagg ccgcgctgct ggcgctggcg acctattccg agctaaaaaa tattattctg   1200
gttgatgaag atgtcgacat ctttgacagc gacgatatcc tgtgggcgat gaccaccgc    1260 atgcagggg acgtcagcat tacgacaatc cccggcattc gcggtcacca gctggatccg    1320
tcccagacgc cggaatacag cccgtcgatc cgtggaaatg gcatcagctg caagaccatt   1380
tttgactgca cggtccctg ggcgctgaaa tcgcactttg agcgcgcgcc gttgccgac     1440 gtcgatccgc gtccgtttgc accggagtat ttcgcccggc tggaaaaaaa ccagggtagc   1500
gcaaaataa                                                           1509

<210> SEQ ID NO 42
<211> LENGTH: 594
<212> TYPE: DNA
<213> ORGANISM: Klebsiella pneumoniae subsp. pneumoniae

<400> SEQUENCE: 42
atgaaactga ttattgggat gacgggggcc accggggcac cgcttggggt ggcattgctg     60
caggcgctgc gcgatatgcc ggaggtggaa acccatctgg tgatgtcgaa atgggccaaa    120
accaccatcg agctggaaac gccctggacg gcgcgcgaag tggccgcgct ggcggacttt    180
tcccacagcc cggcagacca ggccgccacc atctcatccg gttcatttcg taccgacggc    240
atgatcgtta ttccctgcag tatgaaaacg cttgcaggca ttcgcgcggg ttatgccgaa    300
ggactggtgg gccgcgcggc ggacgtggtg ctcaaagagg ggcgcaagct ggtgttggtc    360
ccgcgggaaa tgccgctcag cacgatccat ctggagaaca tgctggcgct gtcccgcatg    420
ggcgtggcga tggtccccgcc gatgtcagct tactacaacc accgagac ggttgacgat     480 atcaccaatc atatcgtcac ccgggtgctg gatcagtttg gcctcgacta tcacaaagcg    540
cgccgctgga acggcttgcg cacggcagaa caatttgcac aggagatcga ataa          594

<210> SEQ ID NO 43
<211> LENGTH: 1188
<212> TYPE: DNA
<213> ORGANISM: Pseudomonas putida

<400> SEQUENCE: 43
atgaaaactc aggttgcaat tattggtgca ggtccgtctg gcctgctgct gggccagctg     60
ctgcacaagg ccggtatcga taacatcatc gtcgaacgcc agactgccga gtacgtacta    120
ggccgcatcc gcgccggggt gctagagcaa ggcacggtcg acctgctgcg cgaggctggc    180
gtggccgagc gcatggaccg tgaaggcctg gtgcacgagg gggttgaact gctggttggc    240
gggcgccgcc agcgtctgga tctcaaagcc ctgaccggcg gcaagacggt gatggtctac    300
ggccagacca aagtcacccg tgacctgatg caggcccgcg aagccagtgg tgcgccgatc    360
atttattcag ccgccaacgt tcagccgcat gaattgaaag gcgagaagcc ctacctgacg    420
```

```
ttcgaaaagg atggccgggt gcagcggatt gactgcgact atatcgccgg ctgcgacggc      480
ttccacggta tctcgcggca gagcatcccg gagggcgtgc tgaaacagta tgagcgggtt      540
tacccgtttg gctggctggg cctgctgtcg gacacaccgc cagtcaatca cgagttgatc      600
tacgcccacc atgagcgcgg tttcgcgttg tgtagccaac gctcgcaaac acgcagccgc      660
tactacctgc aggtaccttt gcaggatcgg gtcgaggagt ggtctgacga gcgtttctgg      720
gacgaactga aagcccgtct gcccgccgag gtggcggcgg acctggtcac aggccccgcg      780
ttggaaaaaa gtattgcgcc gctgcgtagc ctggtggtcg aacccatgca gtatggtcac      840
ctgttcctgg tggggacgc ggcgcacatc gtccccccta cgggtgccaa aggccttaac       900
ctggcggcct ccgacgtcaa ctacctgtac cgcattctgg tcaaggtgta ccacgaaggg      960
cgcgtcgacc tgcttgcgca atactcgccg ctggcactgc cgcgcgtgtg aagggcgag     1020 cgcttcagct ggttcatgac ccaactgctg catgacttcg gtagccacaa ggacgcctgg    1080
gaccagaaga tgcaggaagc tgaccgcgag tacttcctga cctcgccggc gggcctggtg    1140
aacattgccg agaactatgt ggggctgccg ttcgaggaag ttgcctga                 1188
```

<210> SEQ ID NO 44
<211> LENGTH: 1068
<212> TYPE: DNA
<213> ORGANISM: Pseudomonas putida

<400> SEQUENCE: 44

```
atgtacccca aaacacctg gtacgtcgcc tgcaccccg atgagatcgc caccaaaccc        60
ctgggccggc agatctgcgg ggaaaaaatc gtgttctacc gcgcccgcga gaaccaagta     120
gccgccgtcg aggacttctg cccgcaccgc ggcgcaccgt tgtcgttggg ctatgtcgag     180
gacggcaacc tggtgtgcgg ctaccacggc ctggtgatgg gttgcgacgg caagaccgtg     240
tcgatgccgg ccaacggggt gcgtggcttc ccctgcaaca agacctttgc ggccgtcgag     300
cgctatggct tcatctgggt ctggcccggt gaccaggcgc aggccgaccc ggcgctgatt     360
ccgcatctgg aatgggcggt gagtgatgag tgggcctacg gcggcgggct gttccacatc     420
ggttgcgact accgcctgat gatcgacaac ctcatggacc tcacccatga aacctatgtg     480
cacgcctcca gcatcggcca gaaggagatc gacgaggcac cgccggtcac caccgtcacc     540
ggcgacgaag tggtcaccgc ccggcacatg gaaaacatca tggcgccacc gttctggcgc     600
atggccttgc gtggcaatgg cctggccgac gatgtaccag tggaccgctg gcagatctgc     660
cgtttcaccc cacctagcca tgtgctgatc gaagtgggtg tagcgcatgc cggcaagggc     720
ggctaccacg ccgaggcaca gcataaggcg tcgagcatcg tggtcgactt catcaccct      780 gagagcgata cctctatctg gtacttctgg ggcatggcgc gcaacttcgc tgcgcacgac     840
cagaccctga ccgacaacat cgtgagggc caggcaaga tttcagcga agacctggaa        900 atgctcgaac gccagcagca gaacctgctg gcccaccccg agcgcaactt gctgaagctg     960
aatatcgacg ccggcggcgt gcagtcacgc aaagtgctgg agcggatcat cgcccaagag    1020
cgtgcgccgc agccgcaact gatcgccacc agcgccaacc ctgcctga                 1068
```

<210> SEQ ID NO 45
<211> LENGTH: 951
<212> TYPE: DNA
<213> ORGANISM: Pseudomonas putida

<400> SEQUENCE: 45

-continued

```
atgatcgatg ccgtagtggt atcccgtaac gatgaagcgc agggtatctg cagcttcgag    60
ctggccgcgg cagatggcag cctgctgccg gcgttcagcg ccggcgccca tatcgacgtg   120
cacctgcccg acgggctggt gcgccagtat tcgctgtgca accaccccga agaacgccat   180
cgctatctga ttggcgtact caacgacccg gcttcgcggg gcggttctcg tagcctgcac   240
gaacaggtgc aagccggtgc ccggctgcgt atcagtgcgc cgcgcaacct gttcccgctg   300
gccgagggtg cgcagcgcag tttgctgttt gctggcggta tcggcattac cccaatcctg   360
tgcatggccg agcagctgtc cgacagcggc caggccttcg agctgcacta ctgtgcccgc   420
tccagcgagc gtgcggcgtt tgtcgagcgg atccgcagcg cgccgttcgc tgatcggctg   480
ttcgtgcatt ttgacgagca gccggaaacg gcgctggaca tcgcccaggt gctgggcaac   540
ccgcaagatg atgtgcacct gtatgtatgc gggcccggcg ggttcatgca gcatgtgctg   600
gacagcgcga aggggctggg ctggcaggag gccaacctgc accgcgagta cttcgccgca   660
gcaccggtgg atgccagcaa cgatggcagt ttcgcggtgc aggtgggcag cacgggacag   720
gtgttcgagg tgccagccga ccggaccgtg gtgcaggtgc tggaagagaa tggtatcgag   780
atcgccatgt cgtgcgagca gggtatttgc ggcacctgcc tgacacgcgt gctgcagggc   840
acaccggacc atcgcgatct gtttctcacc gaagaggaac aggccctgaa cgatcagttc   900
acgccctgct gctcgcgctc gaagacgccg ctgctggtgc tggacatctg a            951
```

<210> SEQ ID NO 46
<211> LENGTH: 239
<212> TYPE: PRT
<213> ORGANISM: Pseudomonas putida

<400> SEQUENCE: 46

Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
            20                  25                  30

Pro Arg Gln Ala Leu Val Ser Ile Pro Gln Ser Ile Ser Glu Thr Thr
        35                  40                  45

Gly Pro Asp Phe Ser His Leu Gly Phe Gly Ala His Asp His Asp Leu
    50                  55                  60

Leu Leu Asn Phe Asn Asn Gly Gly Leu Pro Ile Gly Glu Arg Ile Ile
65                  70                  75                  80

Val Ala Gly Arg Val Val Asp Gln Tyr Gly Lys Pro Val Pro Asn Thr
                85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
        195                 200                 205

Leu Asp Met Ser Asn Ala Asn Pro Met Asp Cys Leu Ala Tyr Arg Phe
210                 215                 220

Asp Ile Val Leu Arg Gly Gln Arg Lys Thr His Phe Glu Asn Cys
225                 230                 235

<210> SEQ ID NO 47
<211> LENGTH: 201
<212> TYPE: PRT
<213> ORGANISM: Pseudomonas putida

<400> SEQUENCE: 47

Met Pro Ile Glu Leu Leu Pro Glu Thr Pro Ser Gln Thr Ala Gly Pro
1               5                   10                  15

Tyr Val His Ile Gly Leu Ala Leu Glu Ala Ala Gly Asn Pro Thr Arg
                20                  25                  30

Asp Gln Glu Ile Trp Asn Cys Leu Ala Lys Pro Asp Ala Pro Gly Glu
            35                  40                  45

His Ile Leu Leu Ile Gly His Val Tyr Asp Gly Asn Gly His Leu Val
        50                  55                  60

Arg Asp Ser Phe Leu Glu Val Trp Gln Ala Asp Ala Asn Gly Glu Tyr
65                  70                  75                  80

Gln Asp Ala Tyr Asn Leu Glu Asn Ala Phe Asn Ser Phe Gly Arg Thr
                85                  90                  95

Ala Thr Thr Phe Asp Ala Gly Glu Trp Thr Leu Gln Thr Val Lys Pro
            100                 105                 110

Gly Val Val Asn Asn Ala Ala Gly Val Pro Met Ala Pro His Ile Asn
        115                 120                 125

Ile Ser Leu Phe Ala Arg Gly Ile Asn Ile His Leu His Thr Arg Leu
    130                 135                 140

Tyr Phe Asp Asp Glu Ala Gln Ala Asn Ala Lys Cys Pro Val Leu Asn
145                 150                 155                 160

Leu Ile Glu Gln Pro Gln Arg Arg Glu Thr Leu Ile Ala Lys Arg Cys
                165                 170                 175

Glu Val Asp Gly Lys Thr Ala Tyr Arg Phe Asp Ile Arg Ile Gln Gly
            180                 185                 190

Glu Gly Glu Thr Val Phe Phe Asp Phe
        195                 200

<210> SEQ ID NO 48
<211> LENGTH: 311
<212> TYPE: PRT
<213> ORGANISM: Pseudomonas putida

<400> SEQUENCE: 48

Met Thr Val Lys Ile Ser His Thr Ala Asp Ile Gln Ala Phe Phe Asn
1               5                   10                  15

Arg Val Ala Gly Leu Asp His Ala Glu Gly Asn Pro Arg Phe Lys Gln
                20                  25                  30

Ile Ile Leu Arg Val Leu Gln Asp Thr Ala Arg Leu Ile Glu Asp Leu
            35                  40                  45

Glu Ile Thr Glu Asp Glu Phe Trp His Ala Val Asp Tyr Leu Asn Arg
        50                  55                  60

Leu Gly Gly Arg Asn Glu Ala Gly Leu Leu Ala Ala Gly Leu Gly Ile
65                  70                  75                  80

Glu His Phe Leu Asp Leu Leu Gln Asp Ala Lys Asp Ala Glu Ala Gly
                85                  90                  95

Leu Gly Gly Gly Thr Pro Arg Thr Ile Glu Gly Pro Leu Tyr Val Ala
            100                 105                 110

Gly Ala Pro Leu Ala Gln Gly Glu Ala Arg Met Asp Asp Gly Thr Asp
        115                 120                 125

Pro Gly Val Val Met Phe Leu Gln Gly Gln Val Phe Asp Ala Asp Gly
    130                 135                 140

Lys Pro Leu Ala Gly Ala Thr Val Asp Leu Trp His Ala Asn Thr Gln
145                 150                 155                 160

Gly Thr Tyr Ser Tyr Phe Asp Ser Thr Gln Ser Glu Phe Asn Leu Arg
            165                 170                 175

Arg Arg Ile Ile Thr Asp Ala Glu Gly Arg Tyr Arg Ala Arg Ser Ile
        180                 185                 190

Val Pro Ser Gly Tyr Gly Cys Asp Pro Gln Gly Pro Thr Gln Glu Cys
    195                 200                 205

Leu Asp Leu Leu Gly Arg His Gly Gln Arg Pro Ala His Val His Phe
210                 215                 220

Phe Ile Ser Ala Pro Gly His Arg His Leu Thr Thr Gln Ile Asn Phe
225                 230                 235                 240

Ala Gly Asp Lys Tyr Leu Trp Asp Asp Phe Ala Tyr Ala Thr Arg Asp
            245                 250                 255

Gly Leu Ile Gly Glu Leu Arg Phe Val Glu Asp Ala Ala Ala Ala Arg
        260                 265                 270

Asp Arg Gly Val Gln Gly Arg Phe Ala Glu Leu Ser Phe Asp Phe
    275                 280                 285

Arg Leu Gln Gly Ala Lys Ser Pro Asp Ala Glu Ala Arg Ser His Arg
290                 295                 300

Pro Arg Ala Leu Gln Glu Gly
305                 310

<210> SEQ ID NO 49
<211> LENGTH: 373
<212> TYPE: PRT
<213> ORGANISM: Pseudomonas putida

<400> SEQUENCE: 49

Met Thr Ser Val Leu Ile Glu His Ile Asp Ala Ile Val Asp Leu
1               5                   10                  15

Pro Thr Ile Arg Pro His Lys Leu Ala Met His Thr Met Gln Gln Gln
            20                  25                  30

Thr Leu Val Val Leu Arg Leu Arg Cys Ser Asp Gly Val Glu Gly Ile
        35                  40                  45

Gly Glu Ala Thr Thr Ile Gly Gly Leu Ala Tyr Gly Tyr Glu Ser Pro
    50                  55                  60

Glu Gly Ile Lys Ala Asn Ile Asp Ala Tyr Leu Ala Pro Ala Leu Ile
65                  70                  75                  80

Gly Leu Pro Ala Asp Asn Ile Asn Ala Ala Met Leu Lys Leu Asp Lys
            85                  90                  95

Leu Ala Lys Gly Asn Thr Phe Ala Lys Ser Gly Ile Glu Ser Ala Leu
        100                 105                 110

Leu Asp Ala Gln Gly Lys Arg Leu Gly Leu Pro Val Ser Glu Leu Leu
    115                 120                 125

Gly Gly Arg Val Arg Asp Ser Leu Glu Val Ala Trp Thr Leu Ala Ser
130                 135                 140

Gly Asp Thr Ala Arg Asp Ile Ala Glu Ala Gln His Met Leu Asp Ile
145                 150                 155                 160

```
Arg Arg His Arg Val Phe Lys Leu Lys Ile Gly Ala Asn Pro Val Ala
            165                 170                 175

Gln Asp Leu Lys His Val Val Ala Ile Lys Arg Glu Leu Gly Asp Ser
        180                 185                 190

Ala Ser Val Arg Val Asp Val Asn Gln Tyr Trp Asp Glu Ser Gln Ala
    195                 200                 205

Ile Arg Ala Cys Gln Val Leu Gly Asp Asn Gly Ile Asp Leu Ile Glu
210                 215                 220

Gln Pro Ile Ser Arg Ile Asn Arg Ala Gly Gln Val Arg Leu Asn Gln
225                 230                 235                 240

Arg Ser Pro Ala Pro Ile Met Ala Asp Glu Ser Ile Glu Ser Val Glu
                245                 250                 255

Asp Ala Phe Ser Leu Ala Ala Asp Gly Ala Ala Ser Ile Phe Ala Leu
            260                 265                 270

Lys Ile Ala Lys Asn Gly Gly Pro Arg Ala Val Leu Arg Thr Ala Gln
        275                 280                 285

Ile Ala Glu Ala Ala Gly Ile Ala Leu Tyr Gly Gly Thr Met Leu Glu
    290                 295                 300

Gly Ser Ile Gly Thr Leu Ala Ser Ala His Ala Phe Leu Thr Leu Arg
305                 310                 315                 320

Gln Leu Thr Trp Gly Thr Glu Leu Phe Gly Pro Leu Leu Thr Glu
                325                 330                 335

Glu Ile Val Asn Glu Pro Pro Gln Tyr Arg Asp Phe Gln Leu His Ile
            340                 345                 350

Pro His Thr Pro Gly Leu Gly Leu Thr Leu Asp Glu Gln Arg Leu Ala
        355                 360                 365

Arg Phe Ala Arg Arg
    370

<210> SEQ ID NO 50
<211> LENGTH: 502
<212> TYPE: PRT
<213> ORGANISM: Klebsiella pneumoniae subsp. pneumoniae

<400> SEQUENCE: 50

Met Thr Ala Pro Ile Gln Asp Leu Arg Asp Ala Ile Ala Leu Leu Gln
1               5                   10                  15

Gln His Asp Asn Gln Tyr Leu Glu Thr Asp His Pro Val Asp Pro Asn
            20                  25                  30

Ala Glu Leu Ala Gly Val Tyr Arg His Ile Gly Ala Gly Gly Thr Val
        35                  40                  45

Lys Arg Pro Thr Arg Ile Gly Pro Ala Met Met Phe Asn Asn Ile Lys
    50                  55                  60

Gly Tyr Pro His Ser Arg Ile Leu Val Gly Met His Ala Ser Arg Gln
65                  70                  75                  80

Arg Ala Ala Leu Leu Leu Gly Cys Glu Ala Ser Gln Leu Ala Leu Glu
                85                  90                  95

Val Gly Lys Ala Val Lys Lys Pro Val Ala Pro Val Val Pro Ala
            100                 105                 110

Ser Ser Ala Pro Cys Gln Glu Gln Ile Phe Leu Ala Asp Asp Pro Asp
        115                 120                 125

Phe Asp Leu Arg Thr Leu Leu Pro Ala Pro Thr Asn Thr Pro Ile Asp
    130                 135                 140

Ala Gly Pro Phe Phe Cys Leu Gly Leu Ala Leu Ala Ser Asp Pro Val
```

```
                145                 150                 155                 160
Asp Ala Ser Leu Thr Asp Val Thr Ile His Arg Leu Cys Val Gln Gly
                165                 170                 175

Arg Asp Glu Leu Ser Met Phe Leu Ala Ala Gly Arg His Ile Glu Val
                180                 185                 190

Phe Arg Gln Lys Ala Glu Ala Ala Gly Lys Pro Leu Pro Ile Thr Ile
                195                 200                 205

Asn Met Gly Leu Asp Pro Ala Ile Tyr Ile Gly Ala Cys Phe Glu Ala
210                 215                 220

Pro Thr Thr Pro Phe Gly Tyr Asn Glu Leu Gly Val Ala Gly Ala Leu
225                 230                 235                 240

Arg Gln Arg Pro Val Glu Leu Val Gln Gly Val Ser Val Pro Glu Lys
                245                 250                 255

Ala Ile Ala Arg Ala Glu Ile Val Ile Glu Gly Glu Leu Leu Pro Gly
                260                 265                 270

Val Arg Val Arg Glu Asp Gln His Thr Asn Ser Gly His Ala Met Pro
                275                 280                 285

Glu Phe Pro Gly Tyr Cys Gly Gly Ala Asn Pro Ser Leu Pro Val Ile
                290                 295                 300

Lys Val Lys Ala Val Thr Met Arg Asn Asn Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Trp Asn Ala Val Glu Ala Ala Ile Pro Gly Phe Leu Gln
                340                 345                 350

Asn Val Tyr Ala His Thr Ala Gly Gly Gly Lys Phe Leu Gly Ile Leu
                355                 360                 365

Gln Val Lys Lys Arg Gln Pro Ala Asp Glu Gly Arg Gln Gly Gln Ala
                370                 375                 380

Ala Leu Leu Ala Leu Ala Thr Tyr Ser Glu Leu Lys Asn Ile Ile Leu
385                 390                 395                 400

Val Asp Glu Asp Val Asp Ile Phe Asp Ser Asp Ile Leu Trp Ala
                405                 410                 415

Met Thr Thr Arg Met Gln Gly Asp Val Ser Ile Thr Thr Ile Pro Gly
                420                 425                 430

Ile Arg Gly His Gln Leu Asp Pro Ser Gln Thr Pro Glu Tyr Ser Pro
                435                 440                 445

Ser Ile Arg Gly Asn Gly Ile Ser Cys Lys Thr Ile Phe Asp Cys Thr
450                 455                 460

Val Pro Trp Ala Leu Lys Ser His Phe Glu Arg Ala Pro Phe Ala Asp
465                 470                 475                 480

Val Asp Pro Arg Pro Phe Ala Pro Glu Tyr Phe Ala Arg Leu Glu Lys
                485                 490                 495

Asn Gln Gly Ser Ala Lys
                500

<210> SEQ ID NO 51
<211> LENGTH: 1449
<212> TYPE: DNA
<213> ORGANISM: Pseudomonas putida

<400> SEQUENCE: 51
atgttgcagg tgcctttgct gattggcggg cagtcgcgcc ccgccagcga tggacgaacc     60
ttcgagcgct gtaacccggt gactggcgag gtggtgtcgc aggctgccgc cgccacactg    120
```

```
gccgatgccg atgccgcggt ggctgctgcc agcgcggcgt ttccggcctg gccgcccctg      180
gcaccgggcg agcggcgcag ccgcttgctg gcaggcgctg atctgttgca ggcgagggcc      240
gccgagttca tcgccgccgc cggtgaaacc ggggccatgg ccaactggta tggcttcaac      300
gtgaagttgg ccgccaacat gctgcgcgag gctgcagcca tgaccacgca gatcaccggt      360
gaagtgatcc cctcggacgt tcccggcagc ttcgcaatgg ccctgcgcgc gccctgcggc      420
gtggtgttgg gcatcgcacc gtggaacgcc cggtgatac tggccacgcg tgccattgcc        480
atgccgctgg cctgcggcaa caccgtggtg ctcaaggcct cggagctgag cccggcggtc      540
catcggctga tcggccaggt gctgcacgat gcaggcatcg gcgacggcgt ggtcaatgtc      600
atcagcaatg cgccgcagga tgccccgcc atcgtcgagc ggctgatcgc caaccctgcg        660
gtacgccggg tcaacttcac cggttcgacg cacgtcgggc gcatcgtcgg cgaactggcg      720
gcccgccatc tcaagccggc cctgctcgaa ctgggcggca aggcacctt gctggtgctc        780 gacgatgccg acctggacgc cacggtcgaa gcggcggcct cggtgcctca cttcaaccag      840
gggcagatct gcatgtccac cgagcgcctt gtggtggaca gctgtattgc cgacgctttc      900
gtcgacaagc tggcggtgaa gatcgcccgg gctgcgtgcag gtgatccgca agccagcacc    960
tcggtgctcg gctcgctggt cagcgcagcg gccggcgagc gcatcaaggc actgatcgac      1020
gatgccgtgg ccaagggcgc gcgcctggtc agcggcggcc agctggaagg cagcatcctg      1080
caaccgacct tgctcgacaa cgtcgatgcc agcatgcgcc tgtaccgcga ggagtccttc      1140
ggcccggtgg cggtggtact gcgcgccgaa ggcgacgaag ccttgctgca gctggccaac      1200
gactcggagt tcggtctgtc atcggccatt ttcagccgcg acaccagccg cgccctggcc      1260
ttggcccaac gggtggagtc gggtatctgc catatcaacg gcccgaccgt tcacgatgaa      1320
gcgcagatgc cgtttggcgg ggtcaagtcc agcggctatg gcagcttcgg cagccgcacg      1380
gccatcgatc agttcaccca gttgcgctgg gtcaccctcc agcacggccc gcgtcactat      1440
cccatctag                                                              1449

<210> SEQ ID NO 52
<211> LENGTH: 1479
<212> TYPE: DNA
<213> ORGANISM: Pseudomonas putida

<400> SEQUENCE: 52
atggcggtat ttgccagtga ctctttggc cagctgaaag tggagaaaat tatgactgcc        60
cagtggaacc actacattaa cggggaatac gtatcacccg aatctgaaga gtatatccac      120
gagttcatcc caaccacggc tttgccgggt gactcaatcg caaggggctc ggcagctgac      180
gttgataagg ctgttcgtgc cgcggcagcg gctcagcctg cctggaatgc acgcaagcca      240
attgagcggg gtcgtatcct tctcgccata gctcgtttgg ttcgcgccaa cgcagcggct      300
ttctgcgcca agaagcgga agaaactggc aagcctctga gatgccgcg cttttgagatc       360 gaggcatgtg ctcagtactt tgagtattac ggcggtttgg cgacagccat ccagggcgaa      420
accatcaacc tcggcccag ctaccacgcc tataccaccc gagagccatt tggagtggtg       480
ggggtcatcc tgccgtggaa ttcgccactg aaccaagctg ggcgagccat tgccccggca     540
ttggttagcg ggaacaccgt ggtggtcaaa ccttcagagt tcacctcggt gacgatgctc      600
cagttcgcgg aactggttgt gaaagaggca gggttgccac caggcgtatt gaacgtggtt      660
accggcaccg gtaaggaaac cggtgagcct ctggttaaac ccctctgat ccgaaaggtt       720
```

| | |
|---|---|
| gctttcaccg gttctgtccg tgccggacgg gagatcggca agctcgccgc agatcgcatc | 780 |
| attccgctgt cgctcgaatt gggcggcaaa tccccgaaca ttgtcttcga agacgcagat | 840 |
| ctggatcgag ctgtcgcggg tagcgtcttt gccttcaccg tcaacactgg tcaagtctgt | 900 |
| ctcgccggga cccgttgcct ggtgcatgag tcgattttg aaaaattctc caagaagctt | 960 |
| gccggtgctg tagaggcgct tcagttcagc gacggcgaaa gcttcggtct cggccccta | 1020 |
| acgaccaagg ctcagtttga gcaggttcat cgttacaacg agctggccat ccaggagggg | 1080 |
| gctcattgct tggtcggtgg ggaagctcca agtgacaaaa ccggctggta cgtacgaccc | 1140 |
| accgtctaca ccaacgtcaa caactcgatg cggattgctc gggaagaaat tttcggaccc | 1200 |
| gttctggtac tgattccgtt caaggacgaa aacgaggcgg tggccatcgc gaatgactcg | 1260 |
| gactacgggc tcgcgctgg cgtatggacc accgatctgg ctcgcgcgca ccgcgtatcc | 1320 |
| gctcaaatcg aagcgggcca ggtgtacgtc aacgaatatc catcaggtgg cgttgagact | 1380 |
| ccattcggcg gtttcaagca aagcggccat gggcgcgaga agggcattga agcactccac | 1440 |
| cattacaccc aaacaaagac gaccatcatc cgcatttga | 1479 |

<210> SEQ ID NO 53
<211> LENGTH: 1443
<212> TYPE: DNA
<213> ORGANISM: Sphingobium sp. SYK-6

<400> SEQUENCE: 53

| | |
|---|---|
| atggactcag cgcggatcgc gccagaccag gagagagaca gaatggaatt tacccggctt | 60 |
| aaccccatga ccggcgaagt cgcttcgtcg gcgcccgcgc tcaaggcggg tgacattccc | 120 |
| gcgatcgccc gcaaggcccg cgaaggcttc accgcctggt cggtgatggg ccccaatgcg | 180 |
| cgccgcgccg tgctgatgaa agccgcgacg gcgctggaag cccgcgcgga cgcgttcgtc | 240 |
| gatgcgatga tgggagagat cggcgccacc aagggctggg ctctgttcaa tctcggactg | 300 |
| gcggccagca tggtgcgcga ggcagcggcc ctgacgacgc agatcaatgg cgaagtcatc | 360 |
| ccctccgaca agcccggctg cctcgccatg cgctgcgcg aaccggtggg cgtcattctc | 420 |
| ggcatcgcgc cctggaatgc gccgatcatc ctcggcgtgc gcgccatcgc cgtgccgctg | 480 |
| gcttgcggca acagcgtgat cctgaaggcg agcgagacct gcccgcgcac ccatgccctc | 540 |
| atcatcgagg cattcgcaga tgcggggttc cccgagggag tcgtcaacgt cgtcaccaat | 600 |
| gcgccagccg atgcgggcga agtggtcggc gcgctgatcg acgcgccgga agtcaagcgg | 660 |
| atcaatttca ccggctccac cggggtcggc aagatcatcg ccaagcgtgc cgccgagcat | 720 |
| ctcaagcccg tgctgctgga gctgggtggc aaagccccgc tcattgtcct ggaggacgcc | 780 |
| gatctggatg aagccgtcaa gcggccgcc ttcggcgctt tcatgaacca ggggcagatc | 840 |
| tgcatgtcca cggagcggat catcgtggtg gatgcggtgg ccgacgaatt cgccgcccgg | 900 |
| ttcaaggcaa aggtttcggc catgcctgtt ggcgatcccc ggcagggaag cacgccgctg | 960 |
| ggagcggtcg tcgacaccaa gactgtcgcg cattgcctgt ccttgatcga ggatgcgctt | 1020 |
| ggaaagggcg cggagcagct gacgggcggc gagacgacgc agaatgtgct gatgccggcg | 1080 |
| catgtgatcg accgcgtcac gcccgacatg aagctcttcc gggacgagag cttcggtcct | 1140 |
| gtcgtgggga tcatccgcgc acgcgacgcc gagcatgcga tcgaactggc caacgacacc | 1200 |
| gaatatggtc tctcggcctc ggtcttcacg cgcgacacgg ccaagggcct cagcgtcgcc | 1260 |
| cggcggatcg aatccgggat ctgccatgtc aacgggccga cggtccatga cgaggcgcag | 1320 |
| atgcccttcg gcggcgtgaa ggcttcgggc tatggtcgtt tcggcggcaa ggccggcatc | 1380 |

```
gacagcttca cggagctgcg ctggatcacc atcgagaccc agccgggaca tttcccgatc   1440
tga                                                                1443

<210> SEQ ID NO 54
<211> LENGTH: 1389
<212> TYPE: DNA
<213> ORGANISM: Sphingobium sp. SYK-6

<400> SEQUENCE: 54
atggcgaaaa gtcttcaaga tgtgctggac aatgccggaa atgcagtcga tttcctgcgc     60
aaccagcaga ccggcccgaa cgtctatccc ggcgtcccgg cggaatattc caactggcgc    120
aacgagcagc gcgcatgggc caagaccgcc gtgctcttca accagagcta ccacatggtc    180
gagctgatgg tcgaaggccc cgacgccttc gccttcctca actatctcgg catcaacagc    240
ttcaagaact cgcgcccgg caaggccaag cagtgggttc cggtgacggc cgagggctat    300
gtcatcggcg acgtgatcct gttctatctc gccgagaacc agttcaacct cgtcggccgc    360
gcgccggcca tcgagtgggc cgagttccat gccgccaccg gcaagtggaa cgtgacgctc    420
acccgtgacg agcgcaccgc gctgcgcacc gacggcgtgc gtcgccacta tcgcttccag    480
ctgcagggcc ccaacgccat ggcgatccta acggacgcga tgggccagac cccgccggac    540
ctcaaattct tcaacatggc ggacatccag atcgccggga agaccgtcgg cgcgctgcgt    600
cacggcatgg ccggtcagcc gggctatgag ctctatggtc cctggcgga ttatgaggcg    660 gttcattcgg cgctggtcgc ggccggcaag aaccatgggc tggcgctcgt cggcggccgt    720
gcctattcgt ccaacacgct ggaatccggc tgggtgccct cgccgttccc gggctatctc    780
ttcggcgaag gctcggccga cttccgcaag tgggccggcg agaacagcta tggcgccaag    840
tgctccatcg gcggttccta tgtgcccgag agcctggaag gctatggcct gacgccctgg    900
gacatcggct atggcatcat cgtcaagttc gaccatgact tcatcggcaa ggaagcgctg    960
gagaagatgg cgaacgagcc gcacctcgag aaggtgacgc tggcgctgga cgacgaggac   1020
atgctgcgcg tgatgagcag ctatttctcg gactccggtc gtgcgaaata tttcgagttc   1080
ccgagcgcgg tctactcgat gcaccccat gactcggtgc tggtcgacgg caagcatgtc   1140
ggcgtctcga cctgggtcgg ctactcgtcg aacgagggca agatgctcac gctcgcgatg   1200
atcgatccca aatatgccaa gcccggcacg gaagtctcgc tgctctgggg cgagcccaat   1260
ggcggcacct ccaagccgac cgtcgagccg cacgagcaga cggagatcaa ggcggtcgtg   1320
gcgccggtgc cgtactcggc cgtggcgcgc acgggctatg ccgacagctg gcgcaccaag   1380
aaggcctga                                                          1389

<210> SEQ ID NO 55
<211> LENGTH: 1416
<212> TYPE: DNA
<213> ORGANISM: Sphingobium sp. SYK-6

<400> SEQUENCE: 55
atgtcggcac ctaccaatct tgaacaagtg cttgccgccg gcggcaacac cgtcgaaatg     60
ctgcgcaaca gccagatcgg tgcctatgtg tatccggtgg tggcgccgga attctccaac    120
tggcgcaccg agcagtgggc atggcgcaat cggcagtgc tcttcgacca gacccaccac    180
atggtcgacc tctacatccg tgcaaggac gcgctgaagc tgctctccga cacgatgatc    240
aactcgccca agggctggga gcccaacaag gcgaagcagt acgtgcccgt gacgcccttat    300
```

```
ggccatgtca tcggcgacgg catcatcttc tacctcgccg aggaagagtt cgtgtatgtc    360
ggccgcgcgc cggccgccaa ctggctgatg tatcatgcgc agaccggcgg ttataacgtc    420
gacatcgtgc atgacgaccg ctcgccgagc cgcccgatgg gcaagccggt gcagcgcatc    480
tcctggcgct tccagatcca gggcccgaag gcctgggacg tgatcgagaa gctgcacggc    540
ggcacgctcg agaagctcaa attcttcaac atggccgaga tgaacatcgc cggtatgaag    600
atccgcaccc tgcgtcacgg catggccggc gcgccgggtc tcgagatctg gggtccctac    660
gaaacccagg agaaggcccg caacgcgatc ctcgaggcag gcaaggaatt cggcctcatc    720
ccggtcggtt cgcgcgccta tccgtccaac acgctggaat ccggctggat cccgagcccg    780
ctgccggcca tctacaccgg cgacaagctc aaggcctatc gcgagtggct gccggccaac    840
agctatgagg cgagcggcgc catcggcggt tcgttcgtgt ccagcaacat cgaggactat    900
tacgtcaatc cctacgagat cggctatggt cccttcgtga agttcgacca cgacttcatc    960
ggccgcgacg ctctcgaggc gatcgacccg gccacgcagc gcaagaaggt cacgctggcc   1020
tggaacggcg acgacatggc gaagatctac gcttcgctgt tcgacaccga ggccgacgcg   1080
cactacaagt tcttcgacct gccgctggcc aattatgcca acaccaacgc cgacgccgtg   1140
ctcgacgcgg ccggcaacgt ggtcggcatg tcgatgttca ccggctattc ctacaacgag   1200
aagcgcgcgc tttcgctcgc gacgatcgac cacgagatcc ccgtcggcac cgagctgacg   1260
gtcctgtggg gcgaggaaaa tggcggtacg cgcaagacca cggtcgagcc gcacaagcag   1320
atggccgtgc gcgccgtcgt gagcccggtc ccctattcgg tgaccgcgcg cgagacgtac   1380
gaaggcggct ggcgcaaggc tgccgtcacg gcctga                             1416
```